(12) United States Patent  (10) Patent No.: US 9,034,629 B2
Skraly et al.  (45) Date of Patent: May 19, 2015

(54) RECOMBINANT SYNTHESIS OF MEDIUM CHAIN-LENGTH ALKANES

(71) Applicant: Joule Unlimited Technologies, Inc., Bedford, MA (US)

(72) Inventors: Frank Anthony Skraly, Watertown, MA (US); Ning Li, Bedford, MA (US)

(73) Assignee: Joule Unlimited Technologies, Inc., Bedford, MA (US)

(*) Notice: Subject to any disclaimer, the term of this patent is extended or adjusted under 35 U.S.C. 154(b) by 0 days.

(21) Appl. No.: 14/165,214

(22) Filed: Jan. 27, 2014

(65) Prior Publication Data

US 2014/0213826 A1  Jul. 31, 2014

Related U.S. Application Data

(60) Provisional application No. 61/756,973, filed on Jan. 25, 2013.

(51) Int. Cl.
| | |
|---|---|
| *C12N 1/20* | (2006.01) |
| *C12N 15/00* | (2006.01) |
| *C12N 9/06* | (2006.01) |
| *C12N 9/88* | (2006.01) |
| *C12P 5/00* | (2006.01) |
| *C07H 21/04* | (2006.01) |
| *C12P 5/02* | (2006.01) |
| *C12N 15/63* | (2006.01) |
| *C12N 15/74* | (2006.01) |
| *C12N 9/02* | (2006.01) |
| *C12N 9/16* | (2006.01) |

(52) U.S. Cl.
CPC . *C12P 5/02* (2013.01); *C12N 15/63* (2013.01); *C12N 15/74* (2013.01); *C12Y 401/99005* (2013.01); *C12N 9/0008* (2013.01); *C12N 9/16* (2013.01); *C12N 9/88* (2013.01); *C12Y 301/02014* (2013.01); *C12Y 102/99006* (2013.01)

(58) Field of Classification Search
CPC .............. C12Y 301/02014; C12Y 102/99006; C12Y 401/99005; C12N 9/16; C12N 9/88; C12N 9/0008; C12N 15/74; C12P 5/02
See application file for complete search history.

(56) References Cited

U.S. PATENT DOCUMENTS

| | | |
|---|---|---|
| 7,794,969 B1 | 9/2010 | Reppas et al. |
| 7,955,820 B1 | 6/2011 | Reppas et al. |
| 8,043,840 B2 | 10/2011 | Reppas et al. |
| 8,183,027 B2 | 5/2012 | Reppas et al. |
| 8,323,924 B2 | 12/2012 | Schirmer et al. |
| 8,633,002 B2 * | 1/2014 | Roessler et al. .............. 435/155 |
| 2007/0092957 A1 | 4/2007 | Donaldson et al. |
| 2011/0195469 A1 * | 8/2011 | Roessler et al. .............. 435/155 |
| 2011/0245091 A1 | 10/2011 | Golovlev |
| 2011/0250663 A1 * | 10/2011 | Schirmer et al. .............. 435/157 |
| 2012/0009656 A1 * | 1/2012 | Reppas et al. .............. 435/257.2 |
| 2012/0021478 A1 | 1/2012 | Osterhout et al. |
| 2012/0157717 A1 | 6/2012 | Rude et al. |
| 2012/0244589 A1 | 9/2012 | Robertson et al. |
| 2012/0276637 A1 | 11/2012 | Zhou et al. |
| 2013/0111806 A1 | 5/2013 | Reppas et al. |

FOREIGN PATENT DOCUMENTS

| | | |
|---|---|---|
| WO | WO 2009/111513 A1 | 9/2009 |
| WO | WO 2010/044960 A1 | 4/2010 |
| WO | WO 2011/006137 A2 | 1/2011 |
| WO | WO 2011/019858 * | 2/2011 |
| WO | WO 2012/154329 A1 | 11/2012 |

OTHER PUBLICATIONS

Akhtar, M.K. et al., "Carboxylic Acid Reductase is a Versatile Enzyme for the Conversion of Fatty Acids Into Fuels and Chemical Commodities," PNAS, Jan. 2, 2013, pp. 87-92, vol. 110, No. 1.
PCT International Search Report and Written Opinion, PCT Application No. PCT/US2014/013189, Jul. 10, 2014, 21 pages.
GenBank Accession No. YP_001802195 (Aug. 26, 2013), NCBI Sequence Viewer v2.0, 2 pages, [online] [Retrieved on Aug. 7, 2014] Retrieved from the Internet at <URL:http://www.ncbi.nlm.nih.gov/protein/YP_001802195>.
GenBank Accession No. YP_001865325 (Jun. 10, 2013), NCBI Sequence Viewer v2.0, 2 pages, [online] [Retrieved on Aug. 7, 2014] Retrieved from the Internet at <URL:http://www.ncbi.nlm.nih.gov/protein/YP_001865325>.
GenBank Accession No. YP_397029 (Jun. 10, 2013), NCBI Sequence Viewer v2.0, 2 pages, [online] [Retrieved on Aug. 7, 2014] Retrieved from the Internet at <URL:http://www.ncbi.nlm.nih.gov/protein/YP_397029>.
GenBank Accession No. NP_682103 (May 16, 2014), NCBI Sequence Viewer v2.0, 2 pages, [online] [Retrieved on Aug. 7, 2014] Retrieved from the Internet at <URL:http://www.ncbi.nlm.nih.gov/protein/NP_682103>.
GenBank Accession No. YP_889972 (May 16, 2014), NCBI Sequence Viewer v2.0, 3 pages, [online] [Retrieved on Aug. 7, 2014] Retrieved from the Internet at <URL:http://www.ncbi.nlm.nih.gov/protein/YP_889972>.
GenBank Accession No. AAR91681 (Mar. 9, 2004), NCBI Sequence Viewer v2.0, 2 pages, [online] [Retrieved on Aug. 7, 2014] Retrieved from the Internet at <URL:http://www.ncbi.nlm.nih.gov/protein/AAR91681>.
GenBank Accession No. YP_001850422 (Jun. 10, 2013), NCBI Sequence Viewer v2.0, 3 pages, [online] [Retrieved on Aug. 7, 2014] Retrieved from the Internet at <URL:http://www.ncbi.nlm.nih.gov/protein/YP_001850422>.

(Continued)

*Primary Examiner* — Yong Pak
(74) *Attorney, Agent, or Firm* — Fenwick & West LLP; Chang B. Hong

(57) ABSTRACT

The present disclosure identifies methods and compositions for modifying photoautotrophic organisms as hosts, such that the organisms efficiently produce alkanes, and in particular the use of such organisms for the commercial production of alkanes and related molecules. Other materials, methods, and compositions are also described.

16 Claims, 6 Drawing Sheets

(56) References Cited

OTHER PUBLICATIONS

GenBank Accession No. NP_415115 (May 15, 2014), NCBI Sequence Viewer v2.0, 3 pages, [online] [Retrieved on Aug. 7, 2014] Retrieved from the Internet at <URL:http://www.ncbi.nlm.nih.gov/protein/NP_415115>.

GenBank Accession No. ZP_12673024 (Nov. 15, 2012), NCBI Sequence Viewer v2.0, 2 pages, [online] [Retrieved on Aug. 7, 2014] Retrieved from the Internet at <URL:http://www.ncbi.nlm.nih.gov/protein/ZP_12673024.1?report=genpept>.

GenBank Accession No. AAC49269 (Apr. 30, 1996), NCBI Sequence Viewer v2.0, 2 pages, [online] [Retrieved on Aug. 7, 2014] Retrieved from the Internet at <URL:http://www.ncbi.nlm.nih.gov/protein/AAC49269>.

GenBank Accession No. NP_415027 (May 15, 2014), NCBI Sequence Viewer v2.0, 3 pages, [online] [Retrieved on Aug. 7, 2014] Retrieved from the Internet at <URL: http://www.ncbi.nlm.nih.gov/protein/NP_415027>.

GenBank Accession No. AEM72521 (Aug. 27, 2011), NCBI Sequence Viewer v2.0, 2 pages, [online] [Retrieved on Aug. 7, 2014] Retrieved from the Internet at <URL:http://www.ncbi.nlm.nih.gov/protein/AEM72521>.

GenBank Accession No. AAB71731 (Oct. 2, 1997), NCBI Sequence Viewer v2.0, 2 pages, [online] [Retrieved on Aug. 7, 2014] Retrieved from the Internet at <URL:http://www.ncbi.nlm.nih.gov/protein/AAB71731>.

GenBank Accession No. BAB85476 (Mar. 18, 2005), NCBI Sequence Viewer v2.0, 2 pages, [online] [Retrieved on Aug. 7, 2014] Retrieved from the Internet at <URL:http://www.ncbi.nlm.nih.gov/protein/BAB85476>.

GenBank Accession No. NP_416921 (May 15, 2014), NCBI Sequence Viewer v2.0, 3 pages, [online] [Retrieved on Aug. 7, 2014] Retrieved from the Internet at <URL:http://www.ncbi.nlm.nih.gov/protein/NP_416921>.

GenBank Accession No. NP_415026 (May 15, 2014), NCBI Sequence Viewer v2.0, 3 pages, [online] [Retrieved on Aug. 7, 2014] Retrieved from the Internet at <URL:http://www.ncbi.nlm.nih.gov/protein/NP_415026>.

GenBank Accession No. NP_929340 (May 24, 2013), NCBI Sequence Viewer v2.0, 2 pages, [online] [Retrieved on Aug. 7, 2014] Retrieved from the Internet at <URL:http://www.ncbi.nlm.nih.gov/protein/NP_929340>.

GenBank Accession No. YP_047869 (Jun. 10, 2013), NCBI Sequence Viewer v2.0, 2 pages, [online] [Retrieved on Aug. 7, 2014] Retrieved from the Internet at <URL:http://www.ncbi.nlm.nih.gov/protein/YP_047869>.

GenBank Accession No. NP_416319 (May 15, 2014), NCBI Sequence Viewer v2.0, 3 pages, [online] [Retrieved on Aug. 7, 2014] Retrieved from the Internet at <URL:http://www.ncbi.nlm.nih.gov/protein/NP_416319>.

GenBank Accession No. YP_001733936 (Jun. 10, 2013), NCBI Sequence Viewer v2.0, 2 pages, [online] [Retrieved on Aug. 7, 2014] Retrieved from the Internet at <URL:http://www.ncbi.nlm.nih.gov/protein/YP_001733936>.

GenBank Accession No. YP_004054 (Jun. 27, 2013), NCBI Sequence Viewer v2.0, 2 pages, [online] [Retrieved on Aug. 7, 2014] Retrieved from the Internet at <URL:http://www.ncbi.nlm.nih.gov/protein/YP_004054>.

* cited by examiner

RECOMBINANT SYNTHESIS OF MEDIUM CHAIN-LENGTH ALKANES

CROSS-REFERENCE TO RELATED APPLICATIONS

This application is related to U.S. Provisional Application No. 61/756,973, filed Jan. 25,2013, the entire disclosure of which is hereby incorporated by reference in its entirety for all purposes.

SEQUENCE LISTING

The instant application contains a Sequence Listing which has been submitted via EFS-Web and is hereby incorporated by reference in its entirety. Said ASCII copy, created on Jan. 31,2014, is named 25951US_sequencelisting.txt, and is 90,236 bytes in size.

BACKGROUND

Many existing photoautotrophic organisms (i.e., plants, algae, and photosynthetic bacteria) are poorly suited for industrial bioprocessing and have therefore not demonstrated commercial viability. Recombinant photosynthetic microorganisms have been engineered to produce hydrocarbons and alcohols in amounts that exceed the levels produced naturally by the organism.

SUMMARY

Described herein is an engineered microorganism, wherein said engineered microorganism comprises one or more recombinant genes encoding one or more enzymes having enzyme activities which catalyze the production of medium chain-length alkanes, wherein the enzyme activities comprise: an alkane deformylative monooxygenase activity, a thioesterase activity, a carboxylic acid reductase activity, and a phosphopantetheinyl transferase activity; and/or an alkane deformylative monooxygenase activity, a thioesterase activity, a long-chain fatty acid CoA-ligase activity, and a long-chain acyl-CoA reductase activity.

In some aspects, the enzymes comprise an alkane deformylative monooxygenase, a thioesterase, a carboxylic acid reductase, and a phosphopantetheinyl transferase. In some aspects, the alkane deformylative monooxygenase has EC number 4.1.99.5, the thioesterase has EC number 3.1.2.14, the carboxylic acid reductase has EC number 1.2.99.6, and the phosphopantetheinyl transferase has EC number 2.7.8.7. In some aspects, the alkane deformylative monooxygenase is encoded by adm, the thioesterase is encoded by fatB or fatB2, the carboxylic acid reductase is encoded by carB, and the phosphopantetheinyl transferase is encoded by entD.

In some aspects, the enzyme having alkane deformylative monooxygenase activity has EC number 4.1.99.5. In some aspects, the enzyme having thioesterase activity has EC number 3.1.2.14. In some aspects, the enzyme having carboxylic acid reductase activity has EC number 1.2.99.6. In some aspects, the enzyme having phosphopantetheinyl transferase activity has EC number 2.7.8.7.

In some aspects, the enzymes comprise an alkane deformylative monooxygenase, a thioesterase, a long-chain fatty acid CoA-ligase, and a long-chain acyl-CoA reductase. In some aspects, the alkane deformylative monooxygenase has EC number 4.1.99.5, the thioesterase has EC number 3.1.2.14, the long-chain fatty acid CoA-ligase has EC number 6.2.1.3, and the long-chain acyl-CoA reductase has EC number 1.2.1.50. In some aspects, the alkane deformylative monooxygenase is encoded by adm, the thioesterase is encoded by fatB or fatB2, the long-chain fatty acid CoA-ligase is encoded by fadD, and the long-chain acyl-CoA reductase is encoded by acrM.

In some aspects, the enzyme having alkane deformylative monooxygenase activity has EC number 4.1.99.5. In some aspects, the enzyme having thioesterase activity has EC number 3.1.2.14. In some aspects, the enzyme having long-chain fatty acid CoA-ligase activity has EC number 6.2.1.3. In some aspects, the enzyme having long-chain acyl-CoA reductase activity has EC number 1.2.1.50.

In some aspects, the one or more recombinant genes comprise a recombinant gene encoding a thioesterase that catalyzes the conversion of acyl-ACP to a fatty acid. In some aspects, the one or more recombinant genes comprises a recombinant gene encoding a phosphopantetheinyl transferase that phosphopatetheinylates the ACP moiety of a protein encoded by a carboxylic acid reductase gene. In some aspects, the one or more recombinant genes comprise a recombinant gene encoding a carboxylic acid reductase that catalyzes the conversion of fatty acid to fatty aldehyde. In some aspects, the one or more recombinant genes comprise a recombinant gene encoding a alkane deformylative monooxygenase that catalyzes the conversion of fatty aldehyde to an alkane or alkene. In some aspects, the one or more recombinant genes comprise a recombinant gene encoding a fatty acid CoA-ligase that catalyzes the conversion of fatty acid to acyl-CoA. In some aspects, the one or more recombinant genes comprise a recombinant gene encoding an acyl-CoA reductase that catalyzes the conversion of acyl-CoA to fatty aldehyde.

In some aspects, said microorganism is a bacterium. In some aspects, said microorganism is a gram-negative bacterium. In some aspects, said microorganism is *E. coli*.

In some aspects, said microorganism is a photosynthetic microorganism. In some aspects, said microorganism is a cyanobacterium. In some aspects, said microorganism is a thermotolerant cyanobacterium. In some aspects, said microorganism is a Synechococcus species.

In some aspects, expression of an operon comprising the one or more recombinant genes is controlled by a recombinant promoter, and wherein the promoter is constitutive or inducible. In some aspects, said operon is integrated into the genome of said microorganism. In some aspects, said operon is extrachromosomal.

In some aspects, said medium chain-length alkanes are less than or equal to 11 carbon atoms in length. In some aspects, said medium chain-length alkanes are 7 to 11 carbon atoms in length. In some aspects, said medium chain-length alkanes are 7, 8, 9, 10, or 11 carbon atoms in length.

In some aspects, said recombinant genes are at least 90% or at least 95% identical to a sequence shown in the Tables.

Also described herein is a cell culture comprising a culture medium and a microorganism described herein.

Also described herein is a method for producing hydrocarbons, comprising: culturing an engineered microorganism described herein in a culture medium, wherein said engineered microorganism produces increased amounts of medium chain-length alkanes relative to an otherwise identical microorganism, cultured under identical conditions, but lacking said recombinant genes. In some aspects, the method further includes allowing medium chain-length alkanes to accumulate in the culture medium or in the organism. In some aspects, the method further includes isolating at least a portion of the medium chain-length alkanes. In some aspects, the method further includes processing the isolated medium chain-length alkanes to produce a processed material.

Also described herein is a method for producing hydrocarbons, comprising: (i) culturing an engineered microorganism described herein in a culture medium; and (ii) exposing said engineered microorganism to light and inorganic carbon, wherein said exposure results in the conversion of said inorganic carbon by said microorganism into medium chain-length alkanes, wherein said medium chain-length alkanes are produced in an amount greater than that produced by an otherwise identical microorganism, cultured under identical conditions, but lacking said recombinant genes. In some aspects, the method further includes allowing medium chain-length alkanes to accumulate in the culture medium or in the organism. In some aspects, the method further includes isolating at least a portion of the medium chain-length alkanes. In some aspects, the method further includes processing the isolated medium chain-length alkanes to produce a processed material.

Also described herein is a composition comprising medium chain-length alkanes, wherein said medium chain-length alkanes are produced by a method described herein. In some aspects, the composition comprises at least 50%, at least 60%, at least 70%, at least 80%, at least 90%, at least 95%, or at least 99% medium chain-length alkanes.

DETAILED DESCRIPTION

Figure 1:
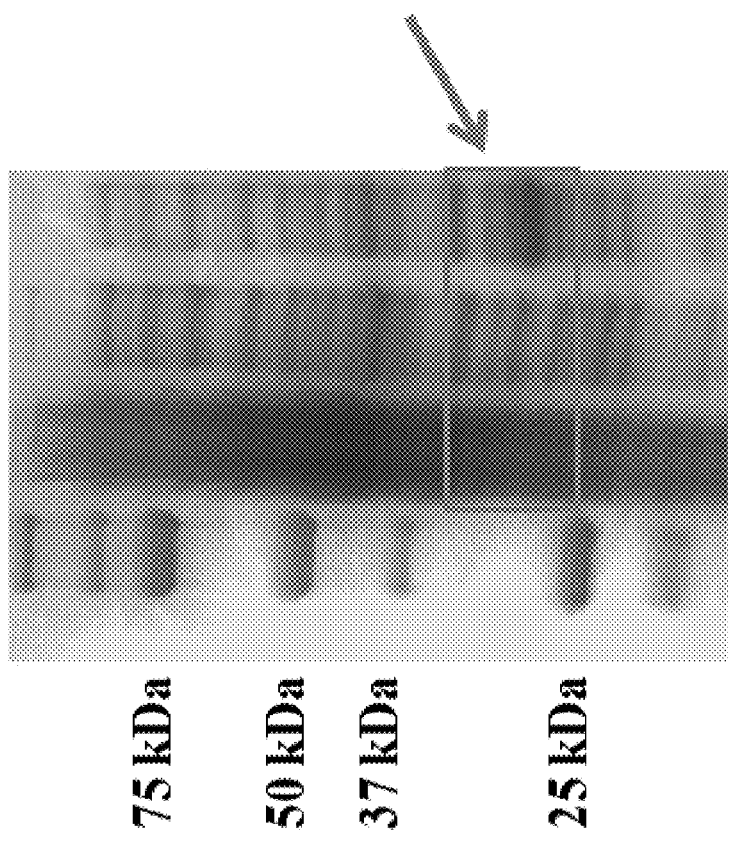
FIG. 1. SDS-PAGE gel showing the overexpression of AcrM protein in *E. coli*.

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook et al., *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); Taylor and Drickamer, *Introduction to Glycobiology*, Oxford Univ. Press (2003); *Worthington Enzyme Manual*, Worthington Biochemical Corp., Freehold, N.J.; *Handbook of Biochemistry: Section A Proteins*, Vol I, CRC Press (1976); Handbook of Biochemistry: Section A Proteins, Vol II, CRC Press (1976); *Essentials of Glycobiology*, Cold Spring Harbor Laboratory Press (1999).

All publications, patents and other references mentioned herein are hereby incorporated by reference in their entireties.

The following terms, unless otherwise indicated, shall be understood to have the following meanings:

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

Unless otherwise indicated, and as an example for all sequences described herein under the general format "SEQ ID NO:", "nucleic acid comprising SEQ ID NO:1" refers to a nucleic acid, at least a portion of which has either (i) the sequence of SEQ ID NO:1, or (ii) a sequence complementary to SEQ ID NO:1. The choice between the two is dictated by the context. For instance, if the nucleic acid is used as a probe, the choice between the two is dictated by the requirement that the probe be complementary to the desired target.

An "isolated" RNA, DNA or a mixed polymer is one which is substantially separated from other cellular components that naturally accompany the native polynucleotide in its natural host cell, e.g., ribosomes, polymerases and genomic sequences with which it is naturally associated.

As used herein, an "isolated" organic molecule (e.g., an alkane) is one which is substantially separated from the cellular components (membrane lipids, chromosomes, proteins) of the host cell from which it originated, or from the medium in which the host cell was cultured. The term does not require that the biomolecule has been separated from all other chemicals, although certain isolated biomolecules may be purified to near homogeneity.

The term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., Molecular Cloning: A Laboratory Manual, 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this present invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., Technique, 1:11-15 (1989) and Caldwell and Joyce, PCR Methods Applic. 2:28-33 (1992)); and "oligonucleotide-directed mutagenesis" (a process which enables the generation of site-specific mutations in any cloned DNA segment of interest; see, e.g., Reidhaar-Olson and Sauer, Science 241:53-57 (1988)).

The term "attenuate" as used herein generally refers to a functional deletion, including a mutation, partial or complete deletion, insertion, or other variation made to a gene sequence or a sequence controlling the transcription of a gene sequence, which reduces or inhibits production of the gene product, or renders the gene product non-functional. In some instances a functional deletion is described as a knockout mutation. Attenuation also includes amino acid sequence changes by altering the nucleic acid sequence, placing the gene under the control of a less active promoter, down-regulation, expressing interfering RNA, ribozymes or antisense sequences that target the gene of interest, or through any other technique known in the art. In one example, the sensitivity of a particular enzyme to feedback inhibition or inhibition caused by a composition that is not a product or a reactant (non-pathway specific feedback) is lessened such that the enzyme activity is not impacted by the presence of a compound. In other instances, an enzyme that has been altered to be less active can be referred to as attenuated.

Deletion: The removal of one or more nucleotides from a nucleic acid molecule or one or more amino acids from a protein, the regions on either side being joined together.

Knock-out: A gene whose level of expression or activity has been reduced to zero. In some examples, a gene is knocked-out via deletion of some or all of its coding sequence. In other examples, a gene is knocked-out via introduction of one or more nucleotides into its open reading frame, which results in translation of a non-sense or otherwise non-functional protein product.

The term "vector" as used herein is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply "expression vectors").

"Operatively linked" or "operably linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{125}$I, $^{32}$P, $^{35}$S, and $^{3}$H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., *Current Protocols in Molecular Biology*, Greene Publishing Associates (1992, and Supplements to 2002) (hereby incorporated by reference).

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusions that include the entirety of the proteins of the present invention have particular utility. The heterologous polypeptide included within the fusion protein of the present invention is at least 6 amino acids in length, often at least 8 amino acids in length, and usefully at least 15, 20, and 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

The term "non-peptide analog" refers to a compound with properties that are analogous to those of a reference polypeptide. A non-peptide compound may also be termed a "peptide mimetic" or a "peptidomimetic." See, e.g., Jones, Amino Acid and Peptide Synthesis, Oxford University Press (1992); Jung, *Combinatorial Peptide and Nonpeptide Libraries: A Handbook*, John Wiley (1997); Bodanszky et al., *Peptide Chemistry—A Practical Textbook*, Springer Verlag (1993); *Synthetic Peptides: A Users Guide*, (Grant, ed., W. H. Freeman and Co., 1992); Evans et al., *J. Med. Chem.* 30:1229 (1987); Fauchere, J. *Adv. Drug Res.* 15:29 (1986); Veber and Freidinger, *Trends Neurosci.*, 8:392-396 (1985); and references sited in each of the above, which are incorporated herein by reference. Such compounds are often developed with the aid of computerized molecular modeling. Peptide mimetics that are structurally similar to useful peptides of the present invention may be used to produce an equivalent effect and are therefore envisioned to be part of the present invention.

A "polypeptide mutant" or "mutein" refers to a polypeptide whose sequence contains an insertion, duplication, deletion, rearrangement or substitution of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein.

A mutein has at least 85% overall sequence homology to its wild-type counterpart. Even more preferred are muteins having at least 90% overall sequence homology to the wild-type protein.

In an even more preferred embodiment, a mutein exhibits at least 95% sequence identity, even more preferably 98%, even more preferably 99% and even more preferably 99.9% overall sequence identity.

Sequence homology may be measured by any common sequence analysis algorithm, such as Gap or Bestfit.

Amino acid substitutions can include those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* (Golub and Gren eds., Sinauer Associates, Sunderland, Mass., $2^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-31 and 25:365-89 (herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A preferred algorithm when comparing a particular polypeptide sequence to a database containing a large number of sequences from different organisms is the computer program BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, *Methods Enzymol.* 183:63-98 (1990) (incorporated by reference herein). For example, percent sequence identity between amino acid sequences can be determined using FASTA with its default parameters (a word size of 2 and the PAM250 scoring matrix), as provided in GCG Version 6.1, herein incorporated by reference.

"Specific binding" refers to the ability of two molecules to bind to each other in preference to binding to other molecules in the environment. Typically, "specific binding" discriminates over adventitious binding in a reaction by at least two-fold, more typically by at least 10-fold, often at least 100-fold. Typically, the affinity or avidity of a specific binding reaction, as quantified by a dissociation constant, is about $10^{-7}$ M or stronger (e.g., about $10^{-8}$ M, $10^{-9}$ M or even stronger).

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

"Carbon-based Products of Interest" include alcohols such as ethanol, propanol, isopropanol, butanol, fatty alcohols, fatty acid esters, wax esters; hydrocarbons and alkanes such as propane, octane, diesel, Jet Propellant 8 (JP8); polymers such as terephthalate, 1,3-propanediol, 1,4-butanediol, polyols, Polyhydroxyalkanoates (PHA), poly-beta-hydroxybutyrate (PHB), acrylate, adipic acid, ε-caprolactone, isoprene, caprolactam, rubber; commodity chemicals such as lactate, Docosahexaenoic acid (DHA), 3-hydroxypropionate, γ-valerolactone, lysine, serine, aspartate, aspartic acid, sorbitol, ascorbate, ascorbic acid, isopentenol, lanosterol, omega-3 DHA, lycopene, itaconate, 1,3-butadiene, ethylene, propylene, succinate, citrate, citric acid, glutamate, malate, 3-hydroxypropionic acid (HPA), lactic acid, THF, gamma butyrolactone, pyrrolidones, hydroxybutyrate, glutamic acid, levulinic acid, acrylic acid, malonic acid; specialty chemicals such as carotenoids, isoprenoids, itaconic acid; pharmaceuticals and pharmaceutical intermediates such as 7-aminodeacetoxycephalosporanic acid (7-ADCA)/cephalosporin, erythromycin, polyketides, statins, paclitaxel, docetaxel, terpenes, peptides, steroids, omega fatty acids and other such suitable products of interest. Such products are useful in the context of biofuels, industrial and specialty chemicals, as intermediates used to make additional products, such as nutritional supplements, neutraceuticals, polymers, paraffin replacements, personal care products and pharmaceuticals.

Biofuel: A biofuel refers to any fuel that derives from a biological source. Biofuel can refer to one or more hydrocarbons, one or more alcohols (such as ethanol), one or more fatty esters, or a mixture thereof.

Hydrocarbon: The term generally refers to a chemical compound that consists of the elements carbon (C), hydrogen (H) and optionally oxygen (O). There are essentially three types of hydrocarbons, e.g., aromatic hydrocarbons, saturated hydrocarbons and unsaturated hydrocarbons such as alkenes, alkynes, and dienes. The term also includes fuels, biofuels, plastics, waxes, solvents and oils. Hydrocarbons encompass biofuels, as well as plastics, waxes, solvents and oils.

Unless otherwise defined, all technical and scientific terms used herein have the same meaning as commonly understood by one of ordinary skill in the art to which this present invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and claims, the word "comprise" or variations such as "comprises" or "comprising", will be understood to imply the inclusion of a stated integer or group of integers but not the exclusion of any other integer or group of integers.

Nucleic Acid Sequences

The present invention provides isolated nucleic acid molecules for genes encoding enzymes, and variants thereof. Exemplary full-length nucleic acid sequences for genes encoding enzymes and the corresponding amino acid sequences are presented in Tables 1 and 2.

In one embodiment, the present invention provides an isolated nucleic acid molecule having a nucleic acid sequence comprising or consisting of a gene coding for an alkane deformylative monooxygenase, a thioesterase, a carboxylic acid reductase, a phosphopanthetheinyl transferase, a long-chain fatty acid CoA-ligase, and/or a long-chain acyl-CoA reductase and homologs, variants and derivatives thereof expressed in a host cell of interest. The present invention also provides a nucleic acid molecule comprising or consisting of a sequence which is a codon-optimized version of the alkane deformylative monooxygenase, a thioesterase, a carboxylic acid reductase, a phosphopanthetheinyl transferase, a long-chain fatty acid CoA-ligase, and/or a long-chain acyl-CoA reductase genes described herein. In a further embodiment, the present invention provides a nucleic acid molecule and homologs, variants and derivatives of the molecule comprising or consisting of a sequence which is a variant of the alkane deformylative monooxygenase, a thioesterase, a carboxylic acid reductase, a phosphopanthetheinyl transferase, a long-chain fatty acid CoA-ligase, and/or a long-chain acyl-CoA reductase gene having at least 80% identity to the wild-type gene. The nucleic acid sequence can be preferably greater than 80%, 85%, 90%, 95%, 98%, 99%, 99.9% or even higher identity to the wild-type gene.

In another embodiment, the nucleic acid molecule of the present invention encodes a polypeptide having an amino acid sequence disclosed in Tables 1 and 2. Preferably, the nucleic acid molecule of the present invention encodes a polypeptide sequence of at least 50%, 60, 70%, 80%, 85%, 90% or 95% identity to the amino acid sequences shown in Tables 1 and 2 and the identity can even more preferably be 96%, 97%, 98%, 99%, 99.9% or even higher.

The present invention also provides nucleic acid molecules that hybridize under stringent conditions to the above-described nucleic acid molecules. As defined above, and as is well known in the art, stringent hybridizations are performed at about 25° C. below the thermal melting point ($T_m$) for the specific DNA hybrid under a particular set of conditions, where the $T_m$ is the temperature at which 50% of the target sequence hybridizes to a perfectly matched probe. Stringent washing is performed at temperatures about 5° C. lower than the $T_m$ for the specific DNA hybrid under a particular set of conditions.

Nucleic acid molecules comprising a fragment of any one of the above-described nucleic acid sequences are also provided. These fragments preferably contain at least 20 contiguous nucleotides. More preferably the fragments of the nucleic acid sequences contain at least 25, 30, 35, 40, 45, 50, 60, 70, 80, 90, 100 or even more contiguous nucleotides.

The nucleic acid sequence fragments of the present invention display utility in a variety of systems and methods. For example, the fragments may be used as probes in various hybridization techniques. Depending on the method, the target nucleic acid sequences may be either DNA or RNA. The target nucleic acid sequences may be fractionated (e.g., by gel electrophoresis) prior to the hybridization, or the hybridization may be performed on samples in situ. One of skill in the art will appreciate that nucleic acid probes of known sequence find utility in determining chromosomal structure (e.g., by Southern blotting) and in measuring gene expression (e.g., by Northern blotting). In such experiments, the sequence fragments are preferably detectably labeled, so that their specific hybridization to target sequences can be detected and optionally quantified. One of skill in the art will appreciate that the nucleic acid fragments of the present invention may be used in a wide variety of blotting techniques not specifically described herein.

It should also be appreciated that the nucleic acid sequence fragments disclosed herein also find utility as probes when immobilized on microarrays. Methods for creating microarrays by deposition and fixation of nucleic acids onto support substrates are well known in the art. Reviewed in *DNA Microarrays: A Practical Approach* (Practical Approach Series), Schena (ed.), Oxford University Press (1999) (ISBN: 0199637768); Nature Genet. 21(1)(suppl):1-60 (1999); *Microarray Biochip Tools and Technology*, Schena (ed.), Eaton Publishing Company/BioTechniques Books Division (2000) (ISBN: 1881299376), the disclosures of which are incorporated herein by reference in their entireties. Analysis of, for example, gene expression using microarrays comprising nucleic acid sequence fragments, such as the nucleic acid sequence fragments disclosed herein, is a well-established utility for sequence fragments in the field of cell and molecular biology. Other uses for sequence fragments immobilized on microarrays are described in Gerhold et al., *Trends Biochem. Sci.* 24:168-173 (1999) and Zweiger, *Trends Biotechnol.* 17:429-436 (1999); *DNA Microarrays: A Practical Approach* (Practical Approach Series), Schena (ed.), Oxford University Press (1999) (ISBN: 0199637768); Nature Genet.

21(1)(suppl):1-60 (1999); *Microarray Biochip: Tools and Technology*, Schena (ed.), Eaton Publishing Company/Bio-Techniques Books Division (2000) (ISBN: 1881299376), the disclosure of each of which is incorporated herein by reference in its entirety.

As is well known in the art, enzyme activities can be measured in various ways. For example, the pyrophosphorolysis of OMP may be followed spectroscopically (Grubmeyer et al., (1993) *J. Biol. Chem.* 268:20299-20304). Alternatively, the activity of the enzyme can be followed using chromatographic techniques, such as by high performance liquid chromatography (Chung and Sloan, (1986) *J. Chromatogr.* 371:71-81). As another alternative the activity can be indirectly measured by determining the levels of product made from the enzyme activity. These levels can be measured with techniques including aqueous chloroform/methanol extraction as known and described in the art (Cf. M. Kates (1986) *Techniques of Lipidology; Isolation, analysis and identification of Lipids.* Elsevier Science Publishers, New York (ISBN: 0444807322)). More modern techniques include using gas chromatography linked to mass spectrometry (Niessen, W. M. A. (2001). *Current practice of gas chromatography—mass spectrometry.* New York, N.Y.: Marcel Dekker. (ISBN: 0824704738)). Additional modern techniques for identification of recombinant protein activity and products including liquid chromatography-mass spectrometry (LCMS), high performance liquid chromatography (HPLC), capillary electrophoresis, Matrix-Assisted Laser Desorption Ionization time of flight-mass spectrometry (MALDI-TOF MS), nuclear magnetic resonance (NMR), near-infrared (NIR) spectroscopy, viscometry (Knothe, G (1997) *Am. Chem. Soc. Symp. Series,* 666: 172-208), titration for determining free fatty acids (Komers (1997) *Fett/Lipid,* 99(2): 52-54), enzymatic methods (Bailer (1991) *Fresenius J. Anal. Chem.* 340(3): 186), physical property-based methods, wet chemical methods, etc. can be used to analyze the levels and the identity of the product produced by the organisms of the present invention. Other methods and techniques may also be suitable for the measurement of enzyme activity, as would be known by one of skill in the art.

Vectors

Also provided are vectors, including expression vectors, which comprise the above nucleic acid molecules of the present invention, as described further herein. In a first embodiment, the vectors include the isolated nucleic acid molecules described above. In an alternative embodiment, the vectors of the present invention include the above-described nucleic acid molecules operably linked to one or more expression control sequences. The vectors of the instant invention may thus be used to express a polypeptide contributing to alkane producing activity by a host cell.

Vectors useful for expression of nucleic acids in prokaryotes are well known in the art.

Isolated Polypeptides

According to another aspect of the present invention, isolated polypeptides (including muteins, allelic variants, fragments, derivatives, and analogs) encoded by the nucleic acid molecules of the present invention are provided. In one embodiment, the isolated polypeptide comprises the polypeptide sequence corresponding to a polypeptide sequence shown in Table 1 or 2. In an alternative embodiment of the present invention, the isolated polypeptide comprises a polypeptide sequence at least 85% identical to a polypeptide sequence shown in Table 1 or 2. Preferably the isolated polypeptide of the present invention has at least 50%, 60, 70%, 80%, 85%, 90%, 95%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9% or even higher identity to a polypeptide sequence shown in Table 1 or 2.

According to other embodiments of the present invention, isolated polypeptides comprising a fragment of the above-described polypeptide sequences are provided. These fragments preferably include at least 20 contiguous amino acids, more preferably at least 25, 30, 35, 40, 45, 50, 60, 70, 80, 90, 100 or even more contiguous amino acids.

The polypeptides of the present invention also include fusions between the above-described polypeptide sequences and heterologous polypeptides. The heterologous sequences can, for example, include sequences designed to facilitate purification, e.g. histidine tags, and/or visualization of recombinantly-expressed proteins. Other non-limiting examples of protein fusions include those that permit display of the encoded protein on the surface of a phage or a cell, fusions to intrinsically fluorescent proteins, such as green fluorescent protein (GFP), and fusions to the IgG Fc region.

Host Cell Transformants

In another aspect of the present invention, host cells transformed with the nucleic acid molecules or vectors of the present invention, and descendants thereof, are provided. In some embodiments of the present invention, these cells carry the nucleic acid sequences of the present invention on vectors, which may but need not be freely replicating vectors. In other embodiments of the present invention, the nucleic acids have been integrated into the genome of the host cells.

In an alternative embodiment, the host cells of the present invention can be mutated by recombination with a disruption, deletion or mutation of the isolated nucleic acid of the present invention so that the activity of one or more enzyme(s) in the host cell is reduced or eliminated compared to a host cell lacking the mutation.

Selected or Engineered Microorganisms for the Production of Carbon-Based Products of Interest Microorganism: Includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

A variety of host organisms can be transformed to produce a product of interest. Photoautotrophic organisms include eukaryotic plants and algae, as well as prokaryotic cyanobacteria, green-sulfur bacteria, green non-sulfur bacteria, purple sulfur bacteria, and purple non-sulfur bacteria.

Extremophiles are also contemplated as suitable organisms. Such organisms withstand various environmental parameters such as temperature, radiation, pressure, gravity, vacuum, desiccation, salinity, pH, oxygen tension, and chemicals. They include hyperthermophiles, which grow at or above 80° C. such as *Pyrolobus fumarii*; thermophiles, which grow between 60-80° C. such as *Synechococcus lividis*; mesophiles, which grow between 15-60° C. and psychrophiles, which grow at or below 15° C. such as *Psychrobacter* and some insects. Radiation tolerant organisms include *Deinococcus radiodurans*. Pressure-tolerant organisms include piezophiles, which tolerate pressure of 130 MPa. Weight-tolerant organisms include barophiles. Hypergravity (e.g., >1 g) hypogravity (e.g., <1 g) tolerant organisms are also contemplated. Vacuum tolerant organisms include tardigrades, insects, microbes and seeds. Dessicant tolerant and anhydrobiotic organisms include xerophiles such as *Artemia salina*; nematodes, microbes, fungi and lichens. Salt-tolerant organisms include halophiles (e.g., 2-5 M NaCl) *Halobacteriacea* and *Dunaliella salina*. pH-tolerant organisms include alkaliphiles such as *Natronobacterium, Bacillus firmus* OF4, *Spirulina* spp. (e.g., pH>9) and acidophiles such as *Cyanidium caldarium, Ferroplasma* sp. (e.g., low pH). Anaerobes, which cannot tolerate $O_2$ such as *Methanococcus jannaschii*; microaerophils, which tolerate some $O_2$ such as *Clostridium* and aerobes, which require $O_2$ are also contemplated. Gas-tolerant organisms, which tolerate pure $CO_2$ include *Cyanidium caldarium* and metal tolerant organisms include metalotolerants such as *Ferroplasma acidarmanus* (e.g., Cu, As, Cd, Zn), *Ralstonia* sp. CH34 (e.g., Zn, Co, Cd, Hg, Pb). Gross, Michael. *Life on the Edge: Amazing Creatures Thriving in Extreme Environments*. New York: Plenum (1998) and Seckbach, J. "Search for Life in the Universe with Terrestrial Microbes Which Thrive Under Extreme Conditions." In Cristiano Batalli Cosmovici, Stuart Bowyer, and Dan Wertheimer, eds., *Astronomical and Biochemical Origins and the Search for Life in the Universe*, p. 511. Milan: Editrice Compositori (1997).

Plants include but are not limited to the following genera: *Arabidopsis, Beta, Glycine, Jatropha, Miscanthus, Panicum, Phalaris, Populus, Saccharum, Salix, Simmondsia* and *Zea*.

Algae and cyanobacteria include but are not limited to the following genera: *Acanthoceras, Acanthococcus, Acaryochloris, Achnanthes, Achnanthidium, Actinastrum, Actinochloris, Actinocyclus, Actinotaenium, Amphichrysis, Amphidinium, Amphikrikos, Amphipleura, Amphiprora, Amphithrix, Amphora, Anabaena, Anabaenopsis, Aneumastus, Ankistrodesmus, Ankyra, Anomoeoneis, Apatococcus, Aphanizomenon, Aphanocapsa, Aphanochaete, Aphanothece, Apiocystis, Apistonema, Arthrodesmus, Artherospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botryococcus, Botryosphaerella, Brachiomonas, Brachysira, Brachytrichia, Brebissonia, Bulbochaete, Bumilleria, Bumilleriopsis, Caloneis, Calothrix, Campylodiscus, Capsosiphon, Carteria, Catena, Cavinula, Centritractus, Centronella, Ceratium, Chaetoceros, Chaetochloris, Chaetomorpha, Chaetonella, Chaetonema, Chaetopeltis, Chaetophora, Chaetosphaeridium, Chamaesiphon, Chara, Characiochloris, Characiopsis, Characium, Charales, Chilomonas, Chlainomonas, Chlamydoblepharis, Chlamydocapsa, Chlamydomonas, Chlamydomonopsis, Chlamydomyxa, Chlamydonephris, Chlorangiella, Chlorangiopsis, Chlorella, Chlorobotrys, Chlorobrachis, Chlorochytrium, Chlorococcum, Chlorogloea, Chlorogloeopsis, Chlorogonium, Chlorolobion, Chloromonas, Chlorophysema, Chlorophyta, Chlorosaccus, Chlorosarcina, Choricystis, Chromophyton, Chromulina, Chroococcidiopsis, Chroococcus, Chroodactylon, Chroomonas, Chroothece, Chrysamoeba, Chrysapsis, Chrysidiastrum, Chrysocapsa, Chrysocapsella, Chrysochaete, Chrysochromulina, Chrysococcus, Chrysocrinus, Chrysolepidomonas, Chrysolykos, Chrysonebula, Chrysophyta, Chrysopyxis, Chrysosaccus, Chrysophaerella, Chrysostephanosphaera, Clodophora, Clastidium, Closteriopsis, Closterium, Coccomyxa, Cocconeis, Coelastrella, Coelastrum, Coelosphaerium, Coenochloris, Coenococcus, Coenocystis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanodictyon, Cyanonephron, Cyanophora, Cyanophyta, Cyanothece, Cyanothomonas, Cyclonexis, Cyclostephanos, Cyclotella, Cylindrocapsa, Cylindrocystis, Cylindrospermum, Cylindrotheca, Cymatopleura, Cymbella, Cymbellonitzschia, Cystodinium, Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatoma, Diatomella, Dicellula, Dichothrix, Dichotomococcus, Dicranochaete, Dictyochloris, Dictyococcus, Dictyosphaerium, Didymocystis, Didymogenes, Didymosphenia, Dilabifilum, Dimorphococcus, Dinobryon, Dinococcus, Diplochloris, Diploneis, Diplostauron, Distrionella, Docidium, Draparnaldia, Dunaliella, Dysmorphococcus, Ecballocystis, Elakatothrix, Ellerbeckia, Encyonema, Enteromorpha, Entocladia, Entomoneis, Entophysalis, Epichrysis, Epipyxis, Epithemia, Eremosphaera, Euastropsis, Euastrum, Eucapsis, Eucocconeis, Eudorina, Euglena, Euglenophyta, Eunotia, Eustigmatophyta, Eutreptia, Fallacia, Fischerella, Fragilaria, Fragilariforma, Franceia, Frustulia, Curcilla, Geminella, Genicularia, Glaucocystis, Glaucophyta, Glenodiniopsis, Glenodinium, Gloeocapsa, Gloeochaete, Gloeochrysis, Gloeococcus, Gloeocystis, Gloeodendron, Gloeomonas, Gloeoplax, Gloeothece, Gloeotila, Gloeotrichia, Gloiodictyon, Golenkinia, Golenkiniopsis, Gomontia, Gomphocymbella, Gomphonema, Gomphosphaeria, Gonatozygon, Gongrosia, Gongrosira, Goniochloris, Gonium, Gonyostomum, Granulochloris, Granulocystopsis, Groenbladia, Gymnodinium, Gymnozyga, Gyrosigma, Haematococcus, Hafniomonas, Hallassia, Hammatoidea, Hannaea, Hantzschia, Hapalosiphon, Haplotaenium, Haptophyta, Haslea, Hemidinium, Hemitoma, Heribaudiella, Heteromastix, Heterothrix, Hibberdia, Hildenbrandia, Hillea, Holopedium, Homoeothrix, Hormanthonema, Hormotila, Hyalobrachion, Hyalocardium, Hyalodiscus, Hyalogonium, Hyalotheca, Hydrianum, Hydrococcus, Hydrocoleum, Hydrocoryne, Hydrodictyon, Hydrosera, Hydrurus, Hyella, Hymenomonas, Isthmochloron, Johannesbaptistia, Juranyiella, Karayevia, Kathablepharis, Katodinium, Kephyrion, Keratococcus, Kirchneriella, Klebsormidium, Kolbesia, Koliella, Komarekia, Korshikoviella, Kraskella, Lagerheimia, Lagynion, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micractinium, Micrasterias, Microchaete, Microcoleus, Microcystis, Microglena, Micromonas, Microspora, Microthamnion, Mischococcus, Monochrysis, Monodus, Monomastix, Monoraphidium, Monostroma, Mougeotia, Mougeotiopsis, Myochloris, Myromecia, Myxosarcina, Naegeliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaetophora, Onychonema, Oocardium, Oocystis, Opephora, Ophiocytium, Orthoseira, Oscillatoria, Oxyneis, Pachycladella, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodermatium, Phaeophyta, Phaeosphaera, Phaeothamnion, Phormidium, Phycopeltis, Phyllariochloris, Phyllocardium, Phyllomitas, Pinnularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaetophora, Polyedriella, Polyedriopsis, Polygoniochloris, Polyepidomonas, Polytaenia, Polytoma, Polytomella, Porphyridium, Posteriochromonas, Prasinochloris, Prasin-*

*ocladus, Prasinophyta, Prasiola, Prochlorphyta, Prochlorothrix, Protoderma, Protosiphon, Provasoliella, Prymnesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocystis, Pseudostaurastrum, Pseudostaurosira, Pseudotetrastrum, Pteromonas, Punctastruata, Pyramichlamys, Pyramimonas, Pyrrophyta, Quadrichloris, Quadricoccus, Quadrigula, Radiococcus, Radiofilum, Raphidiopsis, Raphidocelis, Raphidonema, Raphidophyta, Peimeria, Rhabdoderma, Rhabdomonas, Rhizoclonium, Rhodomonas, Rhodophyta, Rhoicosphenia, Rhopalodia, Rivularia, Rosenvingiella, Rossithidium, Roya, Scenedesmus, Scherffelia, Schizochlamydella, Schizochlamys, Schizomeris, Schizothrix, Schroederia, Scolioneis, Scotiella, Scotiellopsis, Scourfieldia, Scytonema, Selenastrum, Selenochloris, Sellaphora, Semiorbis, Siderocelis, Diderocystopsis, Dimonsenia, Siphononema, Sirocladium, Sirogonium, Skeletonema, Sorastrum, Spermatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondylosium, Sporotetras, Spumella, Staurastrum, Stauerodesmus, Stauroneis, Staurosira, Staurosirella, Stenopterobia, Stephanocostis, Stephanodiscus, Stephanoporos, Stephanosphaera, Stichococcus, Stichogloea, Stigeoclonium, Stigonema, Stipitococcus, Stokesiella, Strombomonas, Stylochrysalis, Stylodinium, Styloyxis, Stylosphaeridium, Surirella, Sykidion, Symploca, Synechococcus, Synechocystis, Synedra, Synochromonas, Synura, Tabellaria, Tabularia, Teilingia, Temnogametum, Tetmemorus, Tetrachlorella, Tetracyclus, Tetradesmus, Tetraedriella, Tetraedron, Tetraselmis, Tetraspora, Tetrastrum, Thalassiosira, Thamniochaete, Thorakochloris, Thorea, Tolypella, Tolypothrix, Trachelomonas, Trachydiscus, Trebouxia, Trentepholia, Treubaria, Tribonema, Trichodesmium, Trichodiscus, Trochiscia, Tryblionella, Ulothrix, Uroglena, Uronema, Urosolenia, Urospora, Uva, Vacuolaria, Vaucheria, Volvox, Volvulina, Westella, Woloszynskia, Xanthidium, Xanthophyta, Xenococcus, Zygnema, Zygnemopsis,* and *Zygonium.* Cyanobacteria include members of the genus *Chamaesiphon, Chroococcus, Cyanobacterium, Cyanobium, Cyanothece, Dactylococcopsis, Gloeobacter, Gloeocapsa, Gloeothece, Microcystis, Prochlorococcus, Prochloron, Synechococcus, Synechocystis, Cyanocystis, Dermocarpella, Stanieria, Xenococcus, Chroococcidiopsis, Myxosarcina, Arthrospira, Borzia, Crinalium, Geitlerinemia, Leptolyngbya, Limnothrix, Lyngbya, Microcoleus, Oscillatoria, Planktothrix, Prochlorothrix, Pseudanabaena, Spirulina, Starria, Symploca, Trichodesmium, Tychonema, Anabaena, Anabaenopsis, Aphanizomenon, Cyanospira, Cylindrospermopsis, Cylindrospermum, Nodularia, Nostoc, Scylonema, Calothrix, Rivularia, Tolypothrix, Chlorogloeopsis, Fischerella, Geitieria, Iyengariella, Nostochopsis, Stigonema* and *Thermosynechococcus.*

Green non-sulfur bacteria include but are not limited to the following genera: *Chloroflexus, Chloronema, Oscillochloris, Heliothrix, Herpetosiphon, Roseiflexus,* and *Thermomicrobium.*

Green sulfur bacteria include but are not limited to the following genera: *Chlorobium, Clathrochloris,* and *Prosthecochloris.*

Purple sulfur bacteria include but are not limited to the following genera: *Allochromatium, Chromatium, Halochromatium, Isochromatium, Marichromatium, Rhodovulum, Thermochromatium, Thiocapsa, Thiorhodococcus,* and *Thiocystis,*

Purple non-sulfur bacteria include but are not limited to the following genera: *Phaeospirillum, Rhodobaca, Rhodobacter, Rhodomicrobium, Rhodopila, Rhodopseudomonas, Rhodothalassium, Rhodospirillum, Rodovibrio,* and *Roseospira.*

Aerobic chemolithotrophic bacteria include but are not limited to nitrifying bacteria such as *Nitrobacteraceae* sp., *Nitrobacter* sp., *Nitrospina* sp., *Nitrococcus* sp., *Nitrospira* sp., *Nitrosomonas* sp., *Nitrosococcus* sp., *Nitrosospira* sp., *Nitrosolobus* sp., *Nitrosovibrio* sp.; colorless sulfur bacteria such as, *Thiovulum* sp., *Thiobacillus* sp., *Thiomicrospira* sp., *Thiosphaera* sp., *Thermothrix* sp.; obligately chemolithotrophic hydrogen bacteria such as *Hydrogenobacter* sp., iron and manganese-oxidizing and/or depositing bacteria such as *Siderococcus* sp., and magnetotactic bacteria such as *Aquaspirillum* sp.

Archaeobacteria include but are not limited to methanogenic archaeobacteria such as *Methanobacterium* sp., *Methanobrevibacter* sp., *Methanothermus* sp., *Methanococcus* sp., *Methanomicrobium* sp., *Methanospirillum* sp., *Methanogenium* sp., *Methanosarcina* sp., *Methanolobus* sp., *Methanothrix* sp., *Methanococcoides* sp., *Methanoplanus* sp.; extremely thermophilic S-Metabolizers such as *Thermoproteus* sp., *Pyrodictium* sp., *Sulfolobus* sp., *Acidianus* sp. and other microorganisms such as, *Bacillus subtilis, Saccharomyces cerevisiae, Streptomyces* sp., *Ralstonia* sp., *Rhodococcus* sp., *Corynebacteria* sp., *Brevibacteria* sp., *Mycobacteria* sp., and oleaginous yeast.

Preferred organisms for the manufacture of alkanes according to the methods disclosed herein include: *Arabidopsis thaliana, Panicum virgatum, Miscanthus giganteus,* and *Zea mays* (plants); *Botryococcus braunii, Chlamydomonas reinhardtii* and *Dunaliela salina* (algae); *Synechococcus* sp PCC 7002, *Synechococcus* sp. PCC 7942, *Synechocystis* sp. PCC 6803, *Thermosynechococcus elongatus* BP-1 (cyanobacteria); *Chlorobium tepidum* (green sulfur bacteria), *Chloroflexus auranticus* (green non-sulfur bacteria); *Chromatium tepidum* and *Chromatium vinosum* (purple sulfur bacteria); *Rhodospirillum rubrum, Rhodobacter capsulatus,* and *Rhodopseudomonas palusris* (purple non-sulfur bacteria).

Yet other suitable organisms include synthetic cells or cells produced by synthetic genomes as described in Venter et al. US Pat. Pub. No. 2007/0264688, and cell-like systems or synthetic cells as described in Glass et al. US Pat. Pub. No. 2007/0269862.

Still, other suitable organisms include microorganisms that can be engineered to fix carbon dioxide bacteria such as *Escherichia coli, Acetobacter aced, Bacillus subtilis,* yeast and fungi such as *Clostridium ljungdahlii, Clostridium thermocellum, Penicillium chrysogenum, Pichia pastoris, Saccharomyces cerevisiae, Schizosaccharomyces pombe, Pseudomonas fluorescens,* or *Zymomonas mobilis.*

A suitable organism for selecting or engineering is capable of autotrophic fixation of $CO_2$ to products. This would cover photosynthesis and methanogenesis. Acetogenesis, encompassing the three types of $CO_2$ fixation; Calvin cycle, acetyl-CoA pathway and reductive TCA pathway is also covered. The capability to use carbon dioxide as the sole source of cell carbon (autotrophy) is found in almost all major groups of prokaryotes. The $CO_2$ fixation pathways differ between groups, and there is no clear distribution pattern of the four presently-known autotrophic pathways. See, e.g., Fuchs, G. 1989. *Alternative pathways of autotrophic $CO_2$ fixation,* p. 365-382. In H. G. Schlegel, and B. Bowien (ed.), *Autotrophic bacteria.* Springer-Verlag, Berlin, Germany. The reductive pentose phosphate cycle (Calvin-Bassham-Benson cycle) represents the $CO_2$ fixation pathway in almost all aerobic autotrophic bacteria, for example, the cyanobacteria.

Alkane production via engineered cyanobacteria, e.g., a *Synechococcus* or *Thermosynechococcus* species, is preferred. Other preferred organisms include *Synechocystis*, *Klebsiella oxytoca*, *Escherichia coli* or *Saccharomyces cerevisiae*. Other prokaryotic, archaea and eukaryotic host cells are also encompassed within the scope of the present invention.

In some aspects, alkane production via a photosynthetic organism can be carried out using the compositions, materials, and methods described in: PCT/US2009/035937 (filed Mar. 3, 2009); and PCT/US2009/055949 (filed Sep. 3, 2009); each of which is herein incorporated by reference in its entirety, for all purposes.

Carbon-Based Products of Interest: Hydrocarbons & Alcohols

In various embodiments of the invention, desired hydrocarbons and/or alcohols of certain chain length or a mixture thereof can be produced. In certain aspects, the host cell produces at least one of the following carbon-based products of interest: medium chain-length alkanes such as heptane, nonane, and/or undecane. In other aspects, the carbon chain length ranges from $C_2$ to $C_{20}$. Accordingly, the invention provides production of various chain lengths of alkanes suitable for use as fuels & chemicals.

In preferred aspects, the methods provide culturing host cells for direct product secretion for easy recovery without the need to extract biomass. These carbon-based products of interest are secreted directly into the medium. Since the invention enables production of various defined chain length of hydrocarbons and alcohols, the secreted products are easily recovered or separated. The products of the invention, therefore, can be used directly or used with minimal processing.

Fuel Compositions

In various embodiments, compositions produced by the methods of the invention are used as fuels. Such fuels comply with ASTM standards, for instance, standard specifications for diesel fuel oils D 975-09b, and Jet A, Jet A-1 and Jet B as specified in ASTM Specification D. 1655-68. Fuel compositions may require blending of several products to produce a uniform product. The blending process is relatively straightforward, but the determination of the amount of each component to include in a blend is much more difficult. Fuel compositions may, therefore, include aromatic and/or branched hydrocarbons, for instance, 75% saturated and 25% aromatic, wherein some of the saturated hydrocarbons are branched and some are cyclic. Preferably, the methods of the invention produce an array of hydrocarbons, such as $C_2$-$C_{17}$ or $C_{10}$-$C_{15}$ to alter cloud point. Furthermore, the compositions may comprise fuel additives, which are used to enhance the performance of a fuel or engine. For example, fuel additives can be used to alter the freezing/gelling point, cloud point, lubricity, viscosity, oxidative stability, ignition quality, octane level, and flash point. Fuels compositions may also comprise, among others, antioxidants, static dissipater, corrosion inhibitor, icing inhibitor, biocide, metal deactivator and thermal stability improver.

In addition to many environmental advantages of the invention such as $CO_2$ conversion and renewable source, other advantages of the fuel compositions disclosed herein include low sulfur content, low emissions, being free or substantially free of alcohol and having high cetane number.

Example 1

Crude Extract of *E. coli* Cells Overexpressing acrM Convert Lauroyl-CoA to Dodecanal and Decanoyl-CoA to Decanal

*Acinetobacter* sp. M-1 acyl coenzyme A reductase, acrM, was codon-optimized for *E. coli* expression and synthesized by DNA2.0 (Menlo Park, CA; SEQ ID NO. 1) with a NdeI site on the 5' end and an EcoRI site on the 3' end. The obtained gene was subcloned into a pET28a vector (Novagen) by digestion with NdeI and EcoRI and subsequent ligation. The resulting plasmid, pET28a-acrM (SEQ ID NO. 2), containing an N-terminal $His_6$-tagged acrM ("$His_6$" disclosed as SEQ ID NO: 18), was transformed into a BL21(DE3) *E. coli* strain, which was subsequently grown with shaking in Luria-Bertani medium supplemented with 100 μg/mL of kanomycin in a volume of 1 L to $OD_{600}$ =0.8 before induction with 0.25 mM IPTG for 5 hours in a 2-L shaker flask at 37° C. An SDS-PAGE gel demonstrating the overexpression of AcrM protein in pET28a-acrM containing BL21(DE3) *E. coli* cells is shown in FIG. 1.

Figure 2:
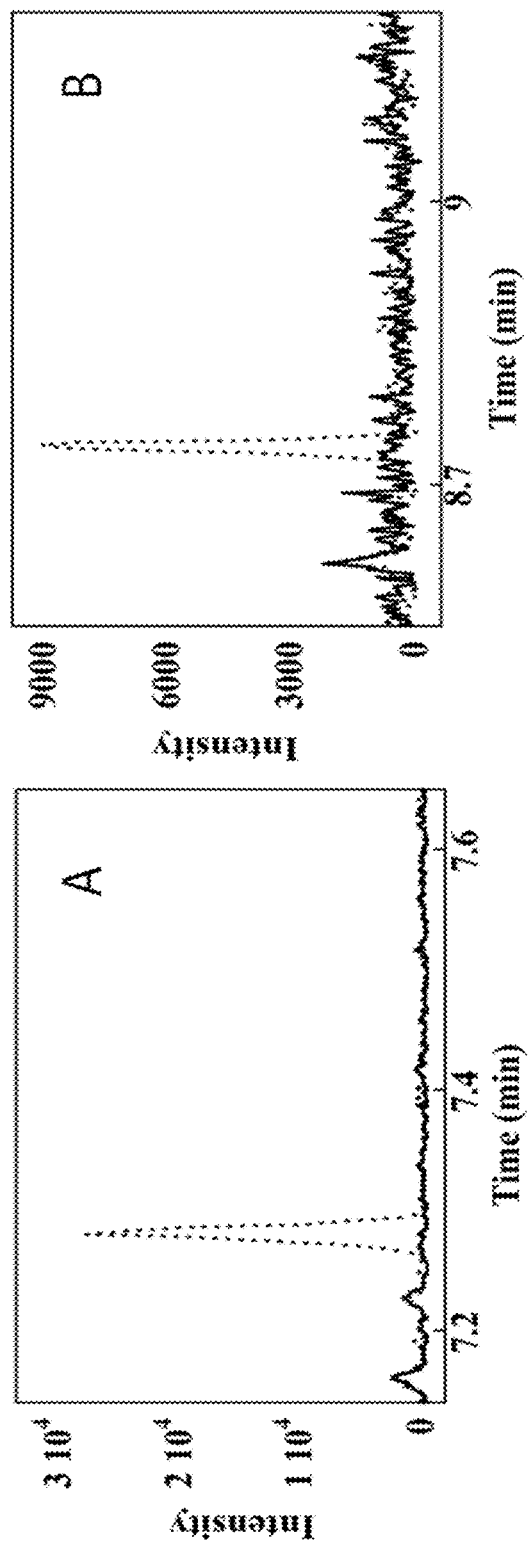
FIG. 2. TIC chromatograms of assays with (A) decanoyl-CoA, (B) lauroyl-CoA. Solid line: wild type BL21(DE3); dotted line: acrM-expressing BL21(DE3).

The *E. coli* cells containing overexpressed AcrM were collected by centrifugation, resuspended in HEPES buffer (100 mM HEPES, 10% glycerol, pH 7.5) at a 1:3 (w/v) ratio and lysed by sonication. 200 μL of buffer solution containing 100 μL total lysate, 1 mM acyl-CoA, 3 mM NADH (Sigma-Aldrich), 100 mM HEPES, 10% glycerol at pH 7.5 was incubated at 37° C. for 30 min, extracted with 100 μL ethyl acetate and analyzed by GC/MS equipped with a HP-5 ms column (Agilent, Santa Clara, Calif.). Total ion chromatography (TIC) indicated the detection of aldehydes produced from corresponding acyl-CoA substrates by the AcrM-containing cell extract in the presence of supplemented NADH, as shown in FIG. 2.

Example 2

Feeding Fatty Acid to *Synechococcus* Sp. PCC 7002 Strain Expressing adm-carB-entD Results in Detection of Corresponding Aldehyde and Alkane The carboxylic acid reductase (carB) gene (SEQ ID NO. 3) was PCR-amplified from *Mycobacterium smegmatis* and verified by sequencing with multiple primers by Genewiz (South Plainfield, N.J.). Cyanothece adm, *E. coli* leaderless tesA and *E. coli* entD genes were codon-optimized for *E. coli* overexpression and synthesized by DNA 2.0 (Menlo Park, Calif.; SEQ ID NO. 4 and 5) with an individual ribosome binding site in front of each gene. All four genes were subcloned into a pUC 19 vector containing an ammonia-repressible P(nir07) promoter, upstream/downstream homology regions, and a spectinomycin marker. The resulting plasmid, pAQ3::P(nir07)-adm-carB-tesA-entD-SpecR (SEQ ID NO. 6), was transformed into wild-type *Synechococcus* sp. PCC 7002 and segregated in the presence of spectinomycin.

Figure 3:
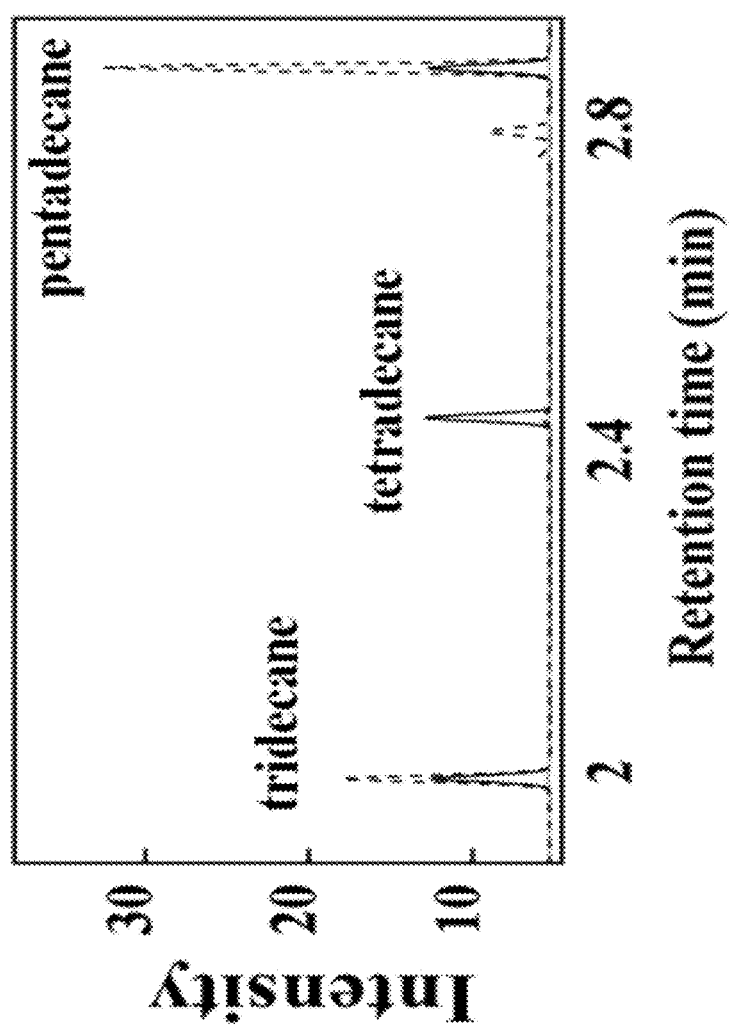
FIG. 3. GC/FID chromatogram showing the detection of C13 and C15 alkanes produced by *Synechococcus* sp. PCC 7002 strain expressing Adm, CarB, TesA and EntD proteins. Grey trace: control strain (does not express CarB protein); solid black trace: Standards of C13, C14, and C15 n-alkanes; dashed black trace: *Synechococcus* sp. PCC 7002 strain expressing Adm, CarB, TesA, and EntD proteins.

The expression and activity of the Adm, CarB, TesA, and EntD proteins were demonstrated by detection of tridecane and pentadecane in the transformed *Synechococcus* sp. PCC 7002 strain by GC/FID (FIG. 3).

Figure 4:
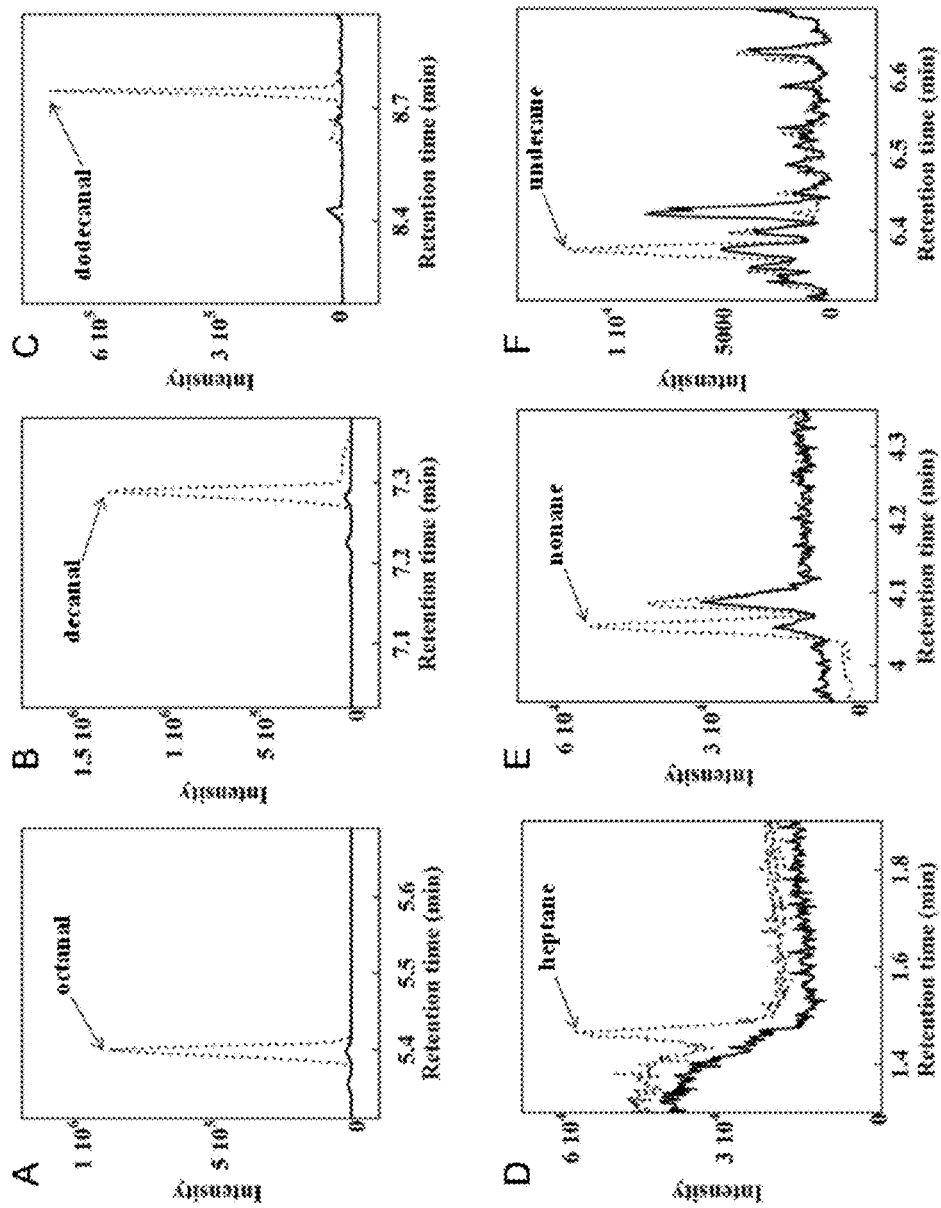
FIG. 4. TIC chromatograms of samples from acid-fed (dashed lines) or control (solid lines) *Synechococcus* sp. PCC 7002 expressing Adm and CarB. A and D: octanoic acid feeding, B and E: decanoic acid feeding, C and F: dodecanoic acid feeding.

The *Synechococcus* sp. PCC 7002 cultures were grown to $OD_{730}$~5 before 1 mM fatty acid (100 mM stock in ethanol) was added and were then shaken at 150 rpm, 37° C. for ~3 hours in the absence (lauric acid feeding) or presence (octanoic acid and decanoic acid feeding) of a pentadecane overlay (6 mL culture with 1 mL overlay). The pentadecane overlay from the octanoic acid-fed culture (FIGS. 4A and 4D), or decanoic acid culture (FIGS. 4B and 4E) was analyzed by GC/MS equipped with an HP-5 ms column. For the lauric acid feeding assay, 1 mL culture was extracted with 400 μL hexane by vortexing for 1 min before being analyzed by GC/MS (FIG. 4C, 4F). Note that the pAQ3::P(nir07)-adm-carB-tesA-entD-SpecR expressing *Synechococcus* sp. PCC

Example 3

*Synechococcus* Sp. PCC 7002 Strain Expressing adm-carB-fatB2-entD Results in Increased Detection of Nonane in Pentadecane Overlay The *E. coli* leaderless tesA of pAQ3::P(nir07)-adm-carB-tesA-entD-SpecR, was replaced by *Cuphea hookeriana* leaderless fatB2 (a medium-chain acyl-ACP thioesterase), which was codon-optimized for *E. coli* overexpression and synthesized by DNA 2.0 (Menlo Park, Calif.; SEQ ID NO. 7), with an individual ribosome binding site in front of the gene, a 5' Kpn I restriction site and a 3' Hind III restriction site. The resulting plasmid, pAQ3::P(nir07)-adm-carB-fatB2-entD-SpecR (SEQ ID NO. 8), was transformed into wild-type *Synechococcus* sp. PCC 7002 and segregated in the presence of spectinomycin.

Figure 5:
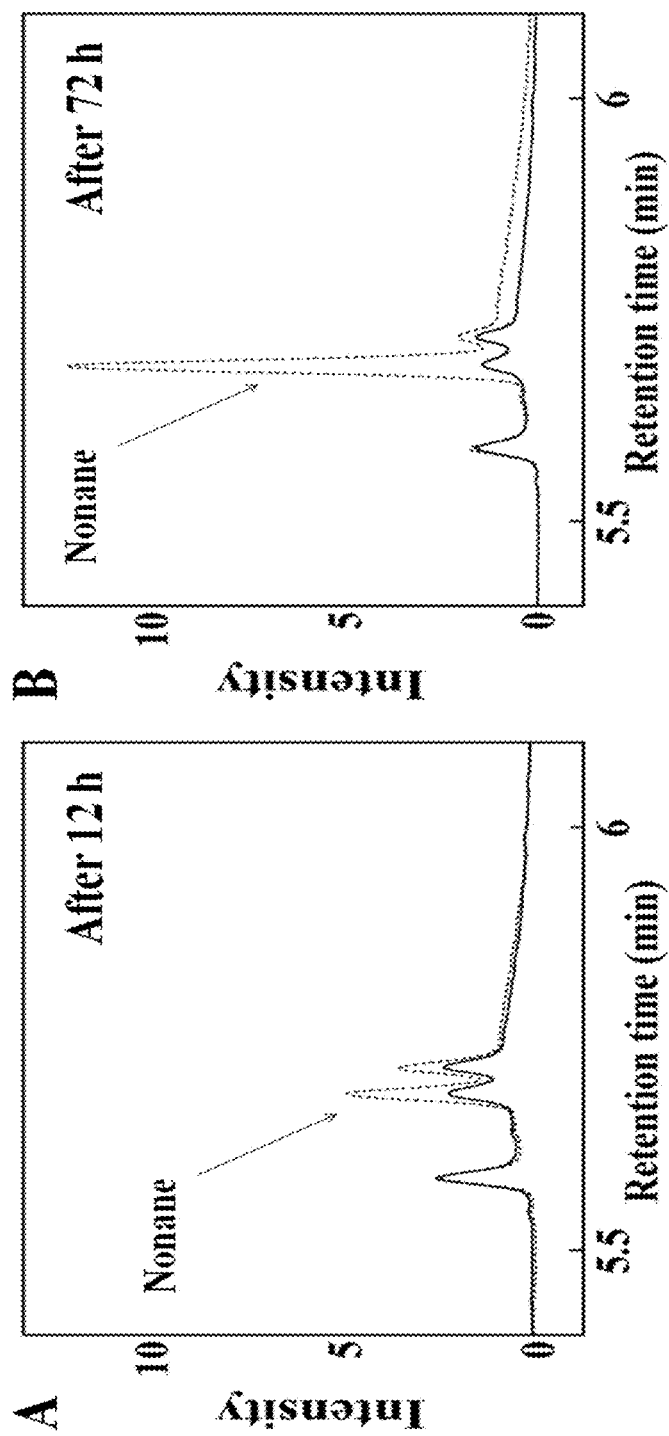
FIG. 5. GC/FID chromatogram showing the detection of nonane produced by *Synechococcus* sp. PCC 7002 strain expressing Adm, CarB, FatB2 and EntD proteins at 12 h and 72 h. Solid trace: control strain (wild type); dotted trace: *Synechococcus* sp. PCC 7002 strain expressing Adm, CarB, FatB2, and EntD proteins.

The wild type *Synechococcus* sp. PCC 7002 and pAQ3::P(nir07)-adm-carB-fatB2-entD-SpecR expressing *Synechococcus* sp. PCC 7002 cultures (35 mL) were grown to $OD_{730}$~3 (in the presence of 2 mM urea) before a 10 mL pentadecane overlay was added. The cultures were shaken at 150 rpm, 37° C. for 3 more days continuously. 100 µL pentadecane overlay samples from each flask were taken 12 hours (FIG. 5A) or 72 hours (FIG. 5B) after pentadecane addition, respectively, and analyzed directly by GC/FID equipped with a 20 meter hp-5 ms column. An increase of nonane production was detected in the pAQ3::P(nir07)-adm-carB-fatB2-entD-SpecR expressing *Synechococcus* sp. PCC 7002 cultures but not in the wild type control ones. A relative increase in octane and heptanes production was also detected in the pAQ3::P(nir07)-adm-carB-fatB2-entD-SpecR expressing *Synechococcus* sp. PCC 7002 cultures (data not shown).

Example 4

Medium Chain-Length Alkane Production

One or more recombinant genes encoding one or more enzymes having enzyme activities which catalyze the production of medium chain-length alkanes are identified and selected. The enzyme activities include: an alkane deformylative monooxygenase activity, a thioesterase activity, a carboxylic acid reductase activity, and a phosphopantetheinyl transferase activity, a long-chain fatty acid CoA-ligase activity, and/or a long-chain acyl-CoA reductase activity. Such genes and enzymes can be those described in Tables 1 and 2.

Figure 6:
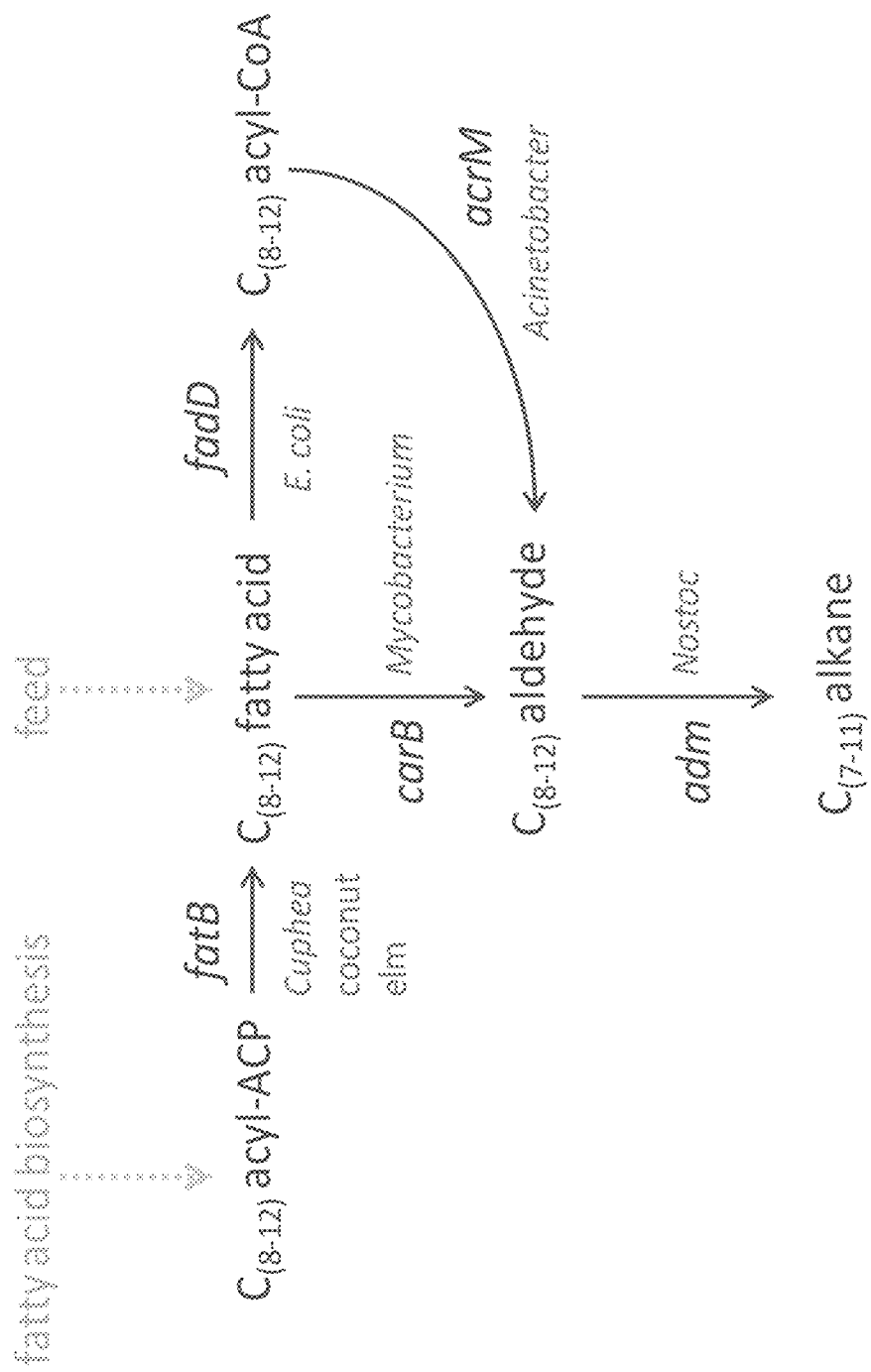
FIG. 6. Examples of pathways for production of medium chain-length alkanes. Note that the use of carB can be facilitated by the product of entD (phosphopatetheinyl transferase), which phosphopatetheinylates the ACP moiety of the CarB protein. For example, one can use the *Bacillus* entD, whose enzyme product has a wide substrate spectrum that includes CarB.

The selected genes are cloned into an expression vector. For example, adm-carB-entD-fatB or adm-acrM-fadD-fatB (or combinations of homologs thereof) are cloned into one or more vectors. See FIG. 6. The genes can be under inducible control (such as the urea-repressible nir07 promoter or the cumate-inducible cum02 promoter). The genes may or may not be expressed operonically; and one or more of the genes can be placed under constitutive control such that when the other gene(s) are induced, the genes under constitutive control are already expressed. For example, one might express adm, carB, and entD constitutively while placing fatty-acid-generating fatB under inducible control; thus when fatty acids are made by fatB after induction, the remainder of the pathway is already present.

One or more vectors are selected and transformed into a microorganism (e.g., cyanobacteria). The cells are grown to a suitable optical density. In some instances cells are grown to a suitable optical density in an uninduced state, and then an induction signal is applied to commence alkane production.

Alkanes are produced by the transformed cells. The alkanes generally have 7, 8, 9, 10, or 11 carbon atoms. In some instances, alkanes are detected. In some instances, alkanes are quantified. In some instances, alkanes are collected.

In some aspects, a thioesterase such as fatB can be used. To test downstream of fatB, fatty acids of various chain lengths are fed along with inorganic carbon (e.g., $CO_2$) to cells, and alkane production is monitored. After fatB addition, cells are provided with inorganic carbon (e.g., $CO_2$) and alkane production is monitored.

TABLE 1

| SEQ ID NO | DESCRIPTION | SEQUENCE |
|---|---|---|
| 1 | acrM (from *Acinetobacter* sp. M-1), codon-optimized for *E. coli* | ATGAATGCAAAACTGAAGAAATTGTTCCAGCAGAAAGTAGACGGCAAGACCATCAT<br>CGTGACCGGTGCAAGCAGCGGTATTGGCTTGACCGTGAGCAAATACCTGGCTCAGG<br>CGGGTGCACACGTGCTGCTGCTGGCGCGTACGAAAGAGAAACTGGATGAGGTCAAG<br>GCGGAGATTGAAGCGGAAGGCGGTAAGGCTACTGTTTTCCCGTGCGATTTGAATGA<br>CATGGAATCCATTGACGCAGTCAGCAAAGAGATCCTGGCAGCCGTTGATCATATCG<br>ACATTCTGGTGAATAACGCGGGTCGCAGCATCCGTCGCGCGGTCCACGAAAGCGTG<br>GATCGCTTCCATGACTTTGAGCGTACCATGCAACTGAATTACTTCGGTGCCGTTCG<br>TCTGGTCCTGAATGTTCTGCCGCACATGATGCAGCGCAAAGATGGCCAAATCATTA<br>ACATTAGCAGCATTGGCGTTTTGGCGAACGCGACGCGTTTCAGCGCGTATGTGGCG<br>AGCAAGGCTGCACTGGATGCCTTCTCCCGTTGTCTGAGCGCCGAGGTCCATTCGCA<br>CAAGATTGCGATTACCTCTATCTATATGCCGCTGGTTCGTACCCCGATGATTGCGC<br>CGACGAAGATCTACAAGTATGTCCCAACGTTGTCCCCGGAAGAGGCGGCTGACCTG<br>ATTGCTTATGCGATCGTTAAACGTCCGAAAAAGATCGCCACCAATCTGGGTCGCCT<br>GGCAAGCATCACCTACGCGATTGCCCCGGACATCAACAACATCCTGATGAGCATCG<br>GCTTTAACCTGTTTCCGTCTAGCACGGCGAGCGTGGGTGAGCAAGAAAAGCTGAAC<br>CTGATTCAACGTGCCTACGCACGTCTGTTTCCTGGTGAACACTGGTAA |
| 2 | Plasmid pET28a-acrM | TGGCGAATGGGACGCGCCCTGTAGCGGCGCATTAAGCGCGGCGGGTGTGGTGGTTA<br>CGCGCAGCGTGACCGCTACACTTGCCAGCGCCCTAGCGCCCGCTCCTTTCGCTTTC<br>TTCCCTTCCTTTCTCGCCACGTTCGCCGGCTTTCCCCGTCAAGCTCTAAATCGGGG<br>GCTCCCTTTAGGGTTCCGATTTAGTGCTTTACGGCACCTCGACCCCAAAAACTTG<br>ATTAGGGTGATGGTTCACGTAGTGGGCCATCGCCCTGATAGACGGTTTTTCGCCCT<br>TTGACGTTGGAGTCCACGTTCTTTAATAGTGGACTCTTGTTCCAAACTGGAACAAC<br>ACTCAACCCTATCTCGGTCTATTCTTTTGATTTATAAGGGATTTTGCCGATTTCGG<br>CCTATTGGTTAAAAAATGAGCTGATTTAACAAAAATTTAACGCGAATTTTAACAAA |

TABLE 1-continued

| SEQ ID NO | DESCRIPTION | SEQUENCE |
|---|---|---|
| | | ATATTAACGTTTACAATTTCAGGTGGCACTTTTCGGGGAAATGTGCGCGGAACCCC |
| | | TATTTGTTTATTTTTCTAAATACATTCAAATATGTATCCGCTCATGAATTAATTCT |
| | | TAGAAAAACTCATCGAGCATCAAATGAAACTGCAATTTATTCATATCAGGATTATC |
| | | AATACCATATTTTTGAAAAAGCCGTTTCTGTAATGAAGGAGAAAACTCACCGAGGC |
| | | AGTTCCATAGGATGGCAAGATCCTGGTATCGGTCTGCGATTCCGACTCGTCCAACA |
| | | TCAATACAACCTATTAATTTCCCCTCGTCAAAAATAAGGTTATCAAGTGAGAAATC |
| | | ACCATGAGTGACGACTGAATCCGGTGAGAATGGCAAAAGTTTATGCATTTCTTTCC |
| | | AGACTTGTTCAACAGGCCAGCCATTACGCTCGTCATCAAAATCACTCGCATCAACC |
| | | AAACCGTTATTCATTCGTGATTGCGCCTGAGCGAGACGAAATACGCGATCGCTGTT |
| | | AAAAGGACAATTACAAACAGGAATCGAATGCAACCGGCGCAGGAACACTGCCAGCG |
| | | CATCAACAATATTTTCACCTGAATCAGGATATTCTTCTAATACCTGGAATGCTGTT |
| | | TTCCCGGGGATCGCAGTGGTGAGTAACCATGCATCATCAGGAGTACGGATAAAATG |
| | | CTTGATGGTCGGAAGAGGCATAAATTCCGTCAGCCAGTTTAGTCTGACCATCTCAT |
| | | CTGTAACATCATTGGCAACGCTACCTTTGCCATGTTTCAGAAACAACTCTGGCGCA |
| | | TCGGGCTTCCCATACAATCGATAGATTGTCGCACCTGATTGCCCGACATTATCGCG |
| | | AGCCCATTTATACCCATATAAATCAGCATCCATGTTGGAATTTAATCGCGGCCTAG |
| | | AGCAAGACGTTTCCCGTTGAATATGGCTCATAACACCCCTTGTATTACTGTTTATG |
| | | TAAGCAGACAGTTTTATTGTTCATGACCAAAATCCCTTAACGTGAGTTTTCGTTCC |
| | | ACTGAGCGTCAGACCCCGTAGAAAAGATCAAAGGATCTTCTTGAGATCCTTTTTTT |
| | | CTGCGCGTAATCTGCTGCTTGCAAACAAAAAAACCACCGCTACCAGCGGTGGTTTG |
| | | TTTGCCGGATCAAGAGCTACCAACTCTTTTTCCGAAGGTAACTGGCTTCAGCAGAG |
| | | CGCAGATACCAAATACTGTCCTTCTAGTGTAGCCGTAGTTAGGCCACCACTTCAAG |
| | | AACTCTGTAGCACCGCCTACATACCTCGCTCTGCTAATCCTGTTACCAGTGGCTGC |
| | | TGCCAGTGGCGATAAGTCGTGTCTTACCGGGTTGGACTCAAGACGATAGTTACCGG |
| | | ATAAGGCGCAGCGGTCGGGCTGAACGGGGGGTTCGTGCACACAGCCCAGCTTGGAG |
| | | CGAACGACCTACACCGAACTGAGATACCTACAGCGTGAGCTATGAGAAAGCGCCAC |
| | | GCTTCCCGAAGGGAGAAAGGCGGACAGGTATCCGGTAAGCGGCAGGGTCGGAACAG |
| | | GAGAGCGCACGAGGGAGCTTCCAGGGGGAAACGCCTGGTATCTTTATAGTCCTGTC |
| | | GGGTTTCGCCACCTCTGACTTGAGCGTCGATTTTTGTGATGCTCGTCAGGGGGGCG |
| | | GAGCCTATGGAAAAACGCCAGCAACGCGGCCTTTTTACGGTTCCTGGCCTTTTGCT |
| | | GGCCTTTTGCTCACATGTTCTTTCCTGCGTTATCCCCTGATTCTGTGGATAACCGT |
| | | ATTACCGCCTTTGAGTGAGCTGATACCGCTCGCCGCAGCCGAACGACCGAGCGCAG |
| | | CGAGTCAGTGAGCGAGGAAGCGGAAGAGCGCCTGATGCGGTATTTTCTCCTTACGC |
| | | ATCTGTGCGGTATTTCACACCGCATATATGGTGCACTCTCAGTACAATCTGCTCTG |
| | | ATGCCGCATAGTTAAGCCAGTATACACTCCGCTATCGCTACGTGACTGGGTCATGG |
| | | CTGCGCCCCGACACCCGCCAACACCCGCTGACGCGCCCTGACGGGCTTGTCTGCTC |
| | | CCGGCATCCGCTTACAGACAAGCTGTGACCGTCTCCGGGAGCTGCATGTGTCAGAG |
| | | GTTTTCACCGTCATCACCGAAACGCGCGAGGCAGCTGCGGTAAAGCTCATCAGCGT |
| | | GGTCGTGAAGCGATTCACAGATGTCTGCCTGTTCATCCGCGTCCAGCTCGTTGAGT |
| | | TTCTCCAGAAGCGTTAATGTCTGGCTTCTGATAAAGCGGGCCATGTTAAGGGCGGT |
| | | TTTTTCCTGTTTGGTCACTGATGCCTCCGTGTAAGGGGGATTTCTGTTCATGGGGG |
| | | TAATGATACCGATGAAACGAGAGAGGATGCTCACGATACGGGTTACTGATGATGAA |
| | | CATGCCCGGTTACTGGAACGTTGTGAGGGTAAACAACTGGCGGTATGGATGCGGCG |
| | | GGACCAGAGAAAAATCACTCAGGGTCAATGCCAGCGCTTCGTTAATACAGATGTAG |
| | | GTGTTCCACAGGGTAGCCAGCAGCATCCTGCGATGCAGATCCGGAACATAATGGTG |
| | | CAGGGCGCTGACTTCCGCGTTTCCAGACTTTACGAAACACGGAAACCGAAGACCAT |
| | | TCATGTTGTTGCTCAGGTCGCAGACGTTTTGCAGCAGCAGTCGCTTCACGTTCGCT |
| | | CGCGTATCGGTGATTCATTCTGCTAACCAGTAAGGCAACCCCGCCAGCCTAGCCGG |
| | | GTCCTCAACGACAGGAGCACGATCATGCGCACCCGTGGGCCGCCATGCCGGCGAT |
| | | AATGGCCTGCTTCTCGCCGAAACGTTTGGTGGCGGGACCAGTGACGAAGGCTTGAG |
| | | CGAGGGCGTGCAAGATTCCGAATACCGCAAGCGACAGGCCGATCATCGTCGCGCTC |
| | | CAGCGAAAGCGGTCCTCGCCGAAAATGACCCAGAGCGCTGCCGGCACCTGTCCTAC |
| | | GAGTTGCATGATAAAGAAGACAGTCATAAGTGCGGCGACGATAGTCATGCCCCGCG |
| | | CCCACCGGAAGGAGCTGACTGGGTTGAAGGCTCTCAAGGGCATCGGTCGAGATCCC |
| | | GGTGCCTAATGAGTGAGCTAACTTACATTAATTGCGTTGCGCTCACTGCCCGCTTT |
| | | CCAGTCGGGAAACCTGTCGTGCCAGCTGCATTAATGAATCGGCCAACGCGCGGGGA |
| | | GAGGCGGTTTGCGTATTGGGCGCCAGGGTGGTTTTTCTTTTCACCAGTGAGACGGG |
| | | CAACAGCTGATTGCCCTTCACCGCCTGGCCCTGAGAGAGTTGCAGCAAGCGGTCCA |
| | | CGCTGGTTTGCCCCAGCAGGCGAAAATCCTGTTTGATGGTGGTTAACGGCGGGATA |
| | | TAACATGAGCTGTCTTCGGTATCGTCGTATCCCACTACCGAGATATCCGCACCAAC |
| | | GCGCAGCCCGGACTCGGTAATGGCGCGCATTGCGCCCAGCGCCATCTGATCGTTGG |
| | | CAACCAGCATCGCAGTGGGAACGATGCCCTCATTCAGCATTTGCATGGTTTGTTGA |
| | | AAACCGGACATGGCACTCCAGTCGCCTTCCCGTTCCGCTATCGGCTGAATTTGATT |
| | | GCGAGTGAGATATTTATGCCAGCCAGCCAGACGCAGACGCGCCGAGACAGAACTTA |
| | | ATGGGCCCGCTAACAGCGCGATTTGCTGGTGACCCAATGCGACCAGATGCTCCACG |
| | | CCCAGTCGCGTACCGTCTTCATGGGAGAAAATAATACTGTTGATGGGTGTCTGGTC |
| | | AGAGACATCAAGAAATAACGCCGGAACATTAGTGCAGGCAGCTTCCACAGCAATGG |
| | | CATCCTGGTCATCCAGCGGATAGTTAATGATCAGCCCACTGACGCGTTGCGCGAGA |
| | | AGATTGTGCACCGCCGCTTTACAGGCTTCGACGCCGCTTCGTTCTACCATCGACAC |
| | | CACCACGCTGGCACCCAGTTGATCGGCGCGAGATTTAATCGCCGCGACAATTTGCG |
| | | ACGGCGCGTGCAGGGCCAGACTGGAGGTGGCAACGCCAATCAGCAACGACTGTTTG |
| | | CCCGCCAGTTGTTGTGCCACGCGGTTGGGAATGTAATTCAGCTCCGCCATCGCCGC |
| | | TTCCACTTTTTCCCGCGTTTTCGCAGAAACGTGGCTGGCCTGGTTCACCACGCGGG |
| | | AAACGGTCTGATAAGAGACACCGGCATACTCTGCGACATCGTATAACGTTACTGGT |
| | | TTCACATTCACCACCCTGAATTGACTCTCTTCCGGGCGCTATCATGCATACCGCG |
| | | AAAGGTTTTGCGCCATTCGATGGTGTCCGGGATCTCGACGCTCTCCCTTATGCGAC |

TABLE 1-continued

| SEQ ID NO | DESCRIPTION | SEQUENCE |
|---|---|---|
| | | TCCTGCATTAGGAAGCAGCCCAGTAGTAGGTTGAGGCCGTTGAGCACCGCCGCCGC
AAGGAATGGTGCATGCAAGGAGATGGCGCCCAACAGTCCCCGGCCACGGGGCCTG
CCACCATACCCACGCCGAAACAAGCGCTCATGAGCCCGAAGTGGCGAGCCCGATCT
TCCCCATCGGTGATGTCGGCGATATAGGCGCCAGCAACCGCACCTGTGGCGCCGGT
GATGCCGGCCACGATGCGTCCGGCGTAGAGGATCGAGATCTCGATCCCGCGAAATT
AATACGACTCACTATAGGGGAATTGTGAGCGGATAACAATTCCCCTCTAGAAATAA
TTTTGTTTAACTTTAAGAAGGAGATATACCATGGGCAGCAGCCATCATCATCATCA
TCACAGCAGCGGCCTGGTGCCGCGCGGCAGCCATATGAATGCAAAACTGAAGAAAT
TGTTCCAGCAGAAAGTAGACGGCAAGACCATCATCGTGACCGGTGCAAGCAGCGGT
ATTGGCTTGACCGTGAGCAAATACCTGGCTCAGGCGGGTGCACACGTGCTGCTGCT
GGCGCGTACGAAAGAGAAACTGGATGAGGTCAAGGCGGAGATTGAAGCGGAAGGCG
GTAAGGCTACTGTTTTCCCGTGCGATTTGAATGACATGGAATCCATTGACGCAGTC
AGCAAAGAGATCCTGGCAGCCGTTGATCATATCGACATTCTGGTGAATAACGCGGG
TCGCAGCATCCGTCGCGCGGTCCACGAAAGCGTGGATCGCTTCCATGACTTTGAGC
GTACCATGCAACTGAATTACTTCGGTGCCGTTCGTCGGTCCTGAATGTTCTGCCG
CACATGATGCAGCGCAAAGATGGCCAAATCATTAACATTAGCAGCATTGGCGTTTT
GGCGAACGCGACGCGTTTCAGCGCGTATGTGGCGAGCAAGGCTGCACTGGATGCCT
TCTCCCGTTGTCTGAGCGCCGAGGTCCATTCGCACAAGATTGCGATTACCTCTATC
TATATGCCGCTGGTTCGTACCCCGATGATTGCGCCGACGAAGATCTACAAGTATGT
CCCAACGTTGTCCCCGGAAGAGGCGGCTGACCTGATTGCTTATGCGATCGTTAAAC
GTCCGAAAAAGATCGCCACCAATCTGGGTCGCCTGGCAAGCATCACCTACGCGATT
GCCCCGGACATCAACAACATCCTGATGAGCATCGGCTTTAACCTGTTTCCGTCTAG
CACGGCGAGCGTGGGTGAGCAAGAAAAGCTGAACCTGATTCAACGTGCCTACGCAC
GTCTGTTTCCTGGTGAACACTGGTAAGAATTCGAGCTCCGTCGACAAGCTTGCGGC
CGCACTCGAGCACCACCACCACCACCACTGAGATCCGGCTGCTAACAAAGCCCGAA
AGGAAGCTGAGTTGGCTGCTGCCACCGCTGAGCAATAACTAGCATAACCCCTTGGG
GCCTCTAAACGGGTCTTGAGGGGTTTTTTGCTGAAAGGAGGAACTATATCCGGAT |
| 3 | carboxylic acid reductase amplified from *Mycobacterium smegmatis*. | GAGCTCGAGGAGGTTTTTACAATGACCAGCGATGTTCACGACGCCACAGACGGCGT
CACCGAAACCGCACTCGACGACGAGCAGTCGACCCGCCGCATCGCCGAGCTGTACG
CCACCGATCCCGAGTTCGCCGCCGCCGCACCGTTGCCCGCCGTGGTCGACGCGGCG
CACAAACCCGGGCTGCGGCTGGCAGAGATCCTGCAGACCCTGTTCACCGGCTACGG
TGACCGCCCGGCGCTGGGATACCGCGCCGTGAACTGGCCACCGACGAGGGCGGGC
GCACCGTGACGCGTCTGCTGCCGCGGTTCGACACCCTCACCTACGCCCAGGTGTGG
TCGCGCGTGCAAGCGGTCGCCGCGGCCCTGCGCCACAACTTCGCGCAGCCGATCTA
CCCCGGCGACGCCGTCGCGACGATCGGTTTCGCGAGTCCCGATTACCTGACGCTGG
ATCTCGTATGCGCCTACCTGGGCCTCGTGAGTGTTCCGCTGCAGCACAACGCACCG
GTCAGCCGGCTCGCCCCGATCCTGGCCGAGGTCGAACCGCGGATCCTCACCGTGAG
CGCCGAATACCTCGACCTCGCAGTCGAATCCGTGCGGGACGTCAACTCGGTGTCGC
AGCTCGTGGTGTTCGACCATCACCCCGAGGTCGACGACCACCGCGACGCACTGGCC
CGCGCGCGTGAACAACTCGCCGGCAAGGGCATCGCCGTCACCACCCTGGACGCGAT
CGCCGACGAGGGCGCCGGGCTGCCGGCCGAACCGATCTACACCGCCGACCATGATC
AGCGCCTCGCGATGATCCTGTACACCTCGGGTTCCACCGGCGCACCCAAGGGTGCG
ATGTACACCGAGGCGATGGTGGCGCGGCTGTGGACCATGTCGTTCATCACGGGTGA
CCCCACGCCGGTCATCAACGTCAACTTCATGCCGCTCAACCACCTGGGCGGGCGCA
TCCCCATTTCCACCGCCGTGCAGAACGGTGGAACCAGTTACTTCGTACCGGAATCC
GACATGTCCACGCTGTTCGAGGATCTCGCGCTGGTGCGCCCGACCGAACTCGGCCT
GGTTCCGCGCGTCGCCGACATGCTCTACCAGCACCACCTCGCCACCGTCGACCGCC
TGGTCACGCAGGGCGCCGACGAACTGACCGCCGAGAAGCAGGCCGGTGCCGAACTG
CGTGAGCAGGTGCTCGGCGGACGCGTGATCACCGGATTCGTCAGCACCGCCACCGCT
GGCCGCGGAGATGAGGGCGTTCCTCGACATCACCCTGGGCGCACACATCGTCGACG
GCTACGGGCTCACCGAGACCGGCGCCGTGACACGCGACGGTGTGATCGTGCGGCCA
CCGGTGATCGACTACAAGCTGATCGACGTTCCCGAACTCGGCTACTTCAGCACCGA
CAAGCCCTACCCGCGTGGCGAACTGCTGGTCAGGTCGCAAACGCTGACTCCCGGGT
ACTACAAGCGCCCGAGGTCACCGCGAGCGTCTTCGACCGGGACGGCTACTACCAC
ACCGGCGACGTCATGGCCGAGACCGCACCCGACCACCTGGTGTACGTGGACCGTCG
CAACAACGTCCTCAAACTCGCGCAGGGCGAGTTCGTGGCGGTCGCCAACCTGGAGG
CGGTGTTCTCCGGCGCGGCGCTGGTGCGCCAGATCTTCGTGTACGGCAACAGCGAG
CGCAGTTTCCTTCTGGCCGTGGTGGTCCCGACGCCGGAGGCGCTCGAGCAGTACGA
TCCGGCCGCGCTCAAGGCCGCGCTGGCCGACTCGCTGCAGCGCACCGCACGCGACG
CCGAACTGCAATCCTACGAGGTGCCGGCCGATTTCATCGTCGAGACCGAGCCGTTC
AGCGCCGCCAACGGGCTGCTGTCGGGTGTCGGAAAACTGCTGCGGCCCAACCTCAA
AGACCGCTACGGGCAGCGCCTGGAGCAGATGTACGCCGATATCGCGGCCACGCAGG
CCAACCAGTTGCGCGAACTGCGGCGCGCGGCCGCACACAACCGGTGATCGACACC
CTCACCCAGGCCGCTGCCACGATCCTCGGCACCGGGAGCGAGGTGGCATCCGACGC
CCACTTCACCGACCTGGGCGGGATTCCCTGTCGGCGCTGACACTTTCGAACCTGC
TGAGCGATTTCTTCGGTTTCGAAGTTCCCGTCGGCACCATCGTGAACCCGGCCACC
AACCTCGCCCAACTCGCCCAGCACATCGAGGCGCAGCGCACCGCGGGTGACCGCAG
GCCGAGTTTCACCACCGTCACGGCGCGGACGCCACCGAGATCCGGGCGAGTGAGC
TGACCCTGGACAAGTTCATCGACGCCGAAACGCTCCGGGCCGCACCGGGTCTGCCC
AAGGTCACCACCGAGCCACGGACGGTGTTGCTCTCGGGCGCGAACGGCTGGCTGGG
CCGGTTCCTCACGTTGCAGTGGCTGGAACGCCTGGCACCTGTCGGCGGCACCCTCA
TCACGATCGTGCGGGGCCGCGACGACGCCGCGGCCCGCACGGCTGACCCAGGCC
TACGACACCGATCCCGAGTTGTCCCGCGCTTCGCCGAGCTGGCCGACCGCCACCT
GCGGGTGGTCGCCGGTGACATCGGCGACCCGAATCTGGGCCTCACACCCGAGATCT
GGCACCGGCTCGCCGCCGAGGTCGACCTGGTGGTGCATCCGGCAGCGCTGGTCAAC |

TABLE 1-continued

| SEQ ID NO | DESCRIPTION | SEQUENCE |
|---|---|---|
| | | CACGTGCTCCCCTACCGGCAGCTGTTCGGCCCCAACGTCGTGGGCACGGCCGAGGT
GATCAAGCTGGCCCTCACCGAACGGATCAAGCCCGTCACGTACCTGTCCACCGTGT
CGGTGGCCATGGGGATCCCCGACTTCGAGGAGGACGGCGACATCCGGACCGTGAGC
CCGGTGCGCCCGCTCGACGGCGGATACGCCAACGGCTACGGCAACAGCAAGTGGGC
CGGCGAGGTGCTGCTGGGGAGGCCCACGATCTGTGCGGGCTGCCCGTGGCGACGT
TCCGCTCGGACATGATCCTGGCGCATCCGCGCTACCGCGGTCAGGTCAACGTGCCA
GACATGTTCACGCGACTCCTGTTGAGCCTCTTGATCACCGGCGTCGCCGCCGCGGTC
GTTCTACATCGGAGACGGTGAGCGCCCGCGGGCGCACTACCCCGGCCTGACGGTCG
ATTTCGTGGCCGAGGCGGTCACGACGCTCGGCGCGCAGCAGCGCGAGGGATACGTG
TCCTACGACGTGATGAACCCGCACGACGACGGGATCTCCCTGGATGTGTTCGTGGA
CTGGCTGATCCGGGCGGCCATCCGATCGACCGGGTCGACGACTACGACGACTGGG
TGCGTCGGTTCGAGACCGCGTTGACCGCGCTTCCCGAGAAGCGCCGCGCACAGACC
GTACTGCCGCTGCTGCACGCGTTCCGCGCTCCGCAGGCACCGTTGCGCGGCGCACC
CGAACCCACGGAGGTGTTCCACGCCGCGGTGCGCACCGCGAAGGTGGGCCCGGGAG
ACATCCCGCACCTCGACGAGGCGCTGATCGACAAGTACATACGCGATCTGCGTGAG
TTCGGTCTGATCTGA<u>GGTACC</u> |
| 4 | codon-optimized Cyanothece adm. | <u>CAT</u>ATGCAAGAACTGGCCCTGAGAAGCGAGCTGGACTTCAATAGCGAAACCTATAA
AGATGCGTATAGCCGTATTAACGCCATTGTGATCGAAGGCGAGCAAGAAGCATACC
AAAACTACCTGGACATGGCGCAACTGCTGCCGGAGGACGAGGCTGAGCTGATTCGT
TTGAGCAAGATGGAGAACCGTCACAAAAAGGGTTTTCAAGCGTGCGGCAAGAACCT
CAATGTGACTCCGGATATGGATTATGCACAGCAGTTCTTTGCGGAGCTGCACGGCA
ATTTTCAGAAGGCTAAAGCCGAGGGTAAGATTGTTACCTGCCTGCTCATCCAAAGC
CTGATCATCGAGGCGTTTGCGATTGCAGCCTACAACATTTACATTCCAGTGGCTGA
TCCGTTTGCACGTAAAATCACCGAGGGTGTCGTCAAGGATGAGTATACCCACCTGA
ATTTCGGCGAAGTTTGGTTGAAGGAACATTTTGAAGCAAGCAAGGCGGAGTTGGAG
GACGCCAACAAAGAGAACTTACCGCTGGTCTGGCAGATGTTGAACCAGGTCGAAAA
GGATGCCGAAGTGCTGGGTATGGAGAAAGAGGCTCTGGTGGAGGACTTTATGATTA
GCTATGGTGAGGCACTGAGCAACATCGGCTTTTCTACGAGAGAAATCATGAAGATG
AGCGCGTACGGTCTGCGTGCAGCATAA<u>GAGCTC</u> |
| 5 | codon-optimized E. coli tesA and E. coli entD genes. | <u>GAGCTCGAGGAGGTTTTTAC</u>AATGACCAGCGATGTTCACGACGCCACAGACGGCGT
CACCGAAACCGCACTCGACGACGAGCAGTCGACCCGCCGCATCGCCGAGCTGTACG
CCACCGATCCCGAGTTCGCCGCCGCCGCCACCGTTGCCCGCCGTGGTCGACGCGGCG
CACAAACCCGGGCTGCGGCTGGCAGAGATCCTGCAGACCCTGTTCACCGGCTACGG
TGACCGCCCGGCGCTGGGATACCGCGCCCGTGAACTGGCCACCGACGAGGGCGGGC
GCACCGTGACGCGTCTGCTGCCGCGGTTCGACACCCTCACCTACGCCCAGGTGTGG
TCGCGCGTGCAAGCGGTCGCCGCGGCCCTGCGCCACAACTTCGCGCAGCCGATCTA
CCCCGGCGACGCCGTCGCGACGATCGGTTTCGCGAGTCCCGATTACCTGACGCTGG
ATCTCGTATGCGCCTACCTGGGCCTCGTGAGTGTTCCGCTGCAGCACAACGCACCG
GTCAGCCGGCTCGCCCCGATCCTGGCCGAGGTCGAACCGGGATCCTCACCGTGAG
CGCCGAATACCTCGACCTCGCAGTCGAATCCGTGCGGGACGTCAACTCGGTGTCGC
AGCTCGTGGTGTTCGACCATCACCCCGAGGTCGACGACCACCGCGACGCACTGGCC
CGCGCGCGTGAACAACTCGCCGGCAAGGGCATCGCCGTCACCACCCTGGACGCGAT
CGCCGACGAGGGCGCCGGGCTGCCGGCCGAACCGATCTACACCGCCGACCATGATC
AGCGCCTCGCGATGATCCTGTACACCTCGGGTTCCACCGGCGCACCCAAGGGTGCG
ATGTACACCGAGGCGATGGTGGCGCGGCTGTGGACCATGTCGTTCATCACGGGTGA
CCCCACGCCGGTCATCAACGTCAACTTCATGCCGCTCAACCACCTGGGCGGGCGCA
TCCCCATTTCCACCGCCGTGCAGAACGGTGGAACCAGTTACTTCGTACCGGAATCC
GACATGTCCACGCTGTTCGAGGATCTCGCGCTGGTGCGCCCGACCGAACTCGGCCT
GGTTCCGCGCGTCGCCGACATGCTCTACCAGCACCACCTCGCCACCGTCGACCGCC
TGGTCACGCAGGGCGCCGACGAACTGACCGCCGAGAAGCAGGCCGGTGCCGAACTG
CGTGAGCAGGTGCTCGGCGGACGCGTGATCACCGGATTCGTCAGCACCGCACCGCT
GGCCGCGGAGATGAGGGCGTTCCTCGACATCACCCTGGGCGCACACATCGTCGACG
GCTACGGGCTCACCGAGACCGGCGCCGTGACACGCGACGGTGTGATCGTGCGGCCA
CCGGTGATCGACTACAAGCTGATCGACGTTCCCGAACTCGGCTACTTCAGCACCGA
CAAGCCCTACCCGCGTGGCGAACTGCTGGTCAGGTCGCAAACGCTGACTCCCGGGT
ACTACAAGCGCCCCGAGGTCACCGCGAGCGTCTTCGACCGGGACGGCTACTACCAC
ACCGGCGACGTCATGGCCGAGACCGCACCCGACCACCTGGTGTACGTGGACCGTCG
CAACAACGTCCTCAAACTCGCGCAGGGCGAGTTCGTGGCGGTCGCCAACCTGGAGG
CGGTGTTCTCCGGCGCGGCGCTGGTGCGCCAGATCTTCGTGTACGGCAACAGCGAG
CGCAGTTTCCTTCTGGCCGTGGTGGTCCCGACGCCGGAGGCGCTCGAGCAGTACGA
TCCGGCCGCGCTCAAGGCCGCGCTGGCCGACTCGCTGCAGCGCACCGCACGCAGCG
CCGAACTGCAATCCTACGAGGTGCCGGCCGATTTCATCGTCGAGACCGAGCCGTTC
AGCGCCGCCAACGGGCTGCTGTCGGGTGTCGGAAAACTGCTGCGGCCCAACCTCAA
AGACCGCTACGGGCAGCGCCTGGAGCAGATGTACGCCGATATCGCGGCCACGCAGG
CCAACCAGTTGCGCGAACTGCGGCGCGCGGCCGCCACACAACCGGTGATCGACACC
CTCACCCAGGCCGCTGCCACGATCCTCGGCACCGGGAGCGAGGTGGCATCCGACGC
CCACTTCACCGACCTGGGCGGGATTCCCTGTCGGCGCTGACACTTTCGAACCTGC
TGAGCGATTTCTTCGGTTTCGAAGTTCCCGTCGGCACCATCGTGAACCCGGCCACC
AACCTCGCCCAACTCGCCCAGCACATCGAGGCGCAGCGACCGCGGGTGACCGCAG
GCCGAGTTTCACCACCGTGCACGGCGCGGACGCCACCGAGATCCGGGCGAGTGAGC
TGACCCTGGACAAGTTCATCGACGCCGAAACGCTCCGGGCCGCACCGGGTCTGCCC
AAGGTCACCACCGAGCCACGGACGGTGTTGCTCTCGGGCGCCAACGGCTGGCTGGG
CCGGTTCCTCACGTTGCAGTGGCTGGAACGCTGGCACCTGTCGGCGGCACCCTCA
TCACGATCGTGCGGGGCCGCGACGACGCCGCGGCCCCGCGCACGGCTGACCCAGGCC |

TABLE 1-continued

| SEQ ID NO | DESCRIPTION | SEQUENCE |
|---|---|---|
| | | TACGACACCGATCCCGAGTTGTCCCGCCGCTTCGCCGAGCTGGCCGACCGCCACCT<br>GCGGGTGGTCGCCGGTGACATCGGCGACCCGAATCTGGGCCTCACACCCGAGATCT<br>GGCACCGGCTCGCCGCCGAGGTCGACCTGGTGGTGCATCCGGCAGCGCTGGTCAAC<br>CACGTGCTCCCCTACCGGCAGCTGTTCGGCCCCAACGTCGTGGGCACGGCCGAGGT<br>GATCAAGCTGGCCCTCACCGAACGGATCAAGCCCGTCACGTACCTGTCCACCGTGT<br>CGGTGGCCATGGGGATCCCCGACTTCGAGGAGGACGGCGACATCCGGACCGTGAGC<br>CCGGTGCGCCCGCTCGACGGCGGATACGCCAACGGCTACGGCAACAGCAAGTGGGC<br>CGGCGAGGTGCTGCTGCGGGAGGCCCACGATCTGTGCGGGCTGCCCGTGGCCGACGT<br>TCCGCTCGGACATGATCCTGGCGCATCCGCGCTACCGCGGTCAGGTCAACGTGCCA<br>GACATGTTCACGCGACTCCTGTTGAGCCTCTTGATCACCGGCGTCGCCGCCGGTC<br>GTTCTACATCGGAGACGGTGAGCGCCCGCGGGCGCACTACCCCGGCCTGACGGTCG<br>ATTTCGTGGCCGAGGCGGTCACGACGCTCGGCGCGCAGCAGCGCGAGGGATACGTG<br>TCCTACGACGTGATGAACCCGCACGACGACGGGATCTCCCTGGATGTGTTCGTGGA<br>CTGGCTGATCCGGGCGGGCCATCCGATCGACCGGGTCGACGACTACGACGACTGGG<br>TGCGTCGGTTCGAGACCGCGTTGACCGCGCTTCCCGAGAAGCGCCGCGCACAGACC<br>GTACTGCCGCTGCTGCACGCGTTCCGCGCTCCGCAGGCACCGTTGCGCGGCGCACC<br>CGAACCCACGGAGGTGTTCCACGCCGCGGTGCGCACCGCGAAGGTGGGCCCGGGAG<br>ACATCCCGCACCTCGACGAGGCGCTGATCGACAAGTACATACGCGATCTGCGTGAG<br>TTCGGTCTGATCTGAGGTACCAGGAGGTTTTTACAATGGCTGATACTTTGTTGATT<br>TTGGGTGATTCTCTCTCTGCAGGCTACCGTATGTCCGCGAGCGCGGCATGGCCGGC<br>TCTGCTGAACGATAAGTGGCAGAGCAAGACCAGCGTGGTCAATGCGAGCATCAGCG<br>GCGATACCAGCCAGCAGGGTCTGGCACGTCTGCCAGCGCTGCTGAAGCAACACCAG<br>CCGCGTTGGGTGCTGGTTGAACTGGGCGGCAATGACGGTCTGCGTGGTTTTCAGCC<br>GCAGCAGACCGAACAAACGTTGCGTCAGATTCTGCAGGACGTCAAGGCGGCTAACG<br>CGGAACCGCTGCTGATGCAAATTCGCCTGCCGGCGAATTATGGTCGTCGTTACAAC<br>GAGGCTTTTCAGCGCCATTTATCCTAAACTGGCTAAAGAGTTTGACGTGCCGCTGCT<br>GCCGTTCTTCATGGAAGAGGTCTACCTGAAACCGCAATGGATGCAAGACGACGGTA<br>TTCATCCGAATCGTGATGCACAACCTTTCATCGCGGATTGGATGGCGAAGCAATTG<br>CAACCGCTGGTGAACCATGACTCGTAAAAGCTTGTTGCTGCATGCAGGAGGTTTTT<br>ACAATGAAAACGACCCACACCAGCTTACCATTTGCCGGCCACACGTTACATTTCGT<br>CGAATTTGATCCGGCGAACTTTTGTGAACAAGACCTGTTGTGGCTGCCGCATTATG<br>CCCAGCTGCAGCACGCAGGCCGTAAGCGTAAAACTGAACATCTGGCCGGTCGCATT<br>GCGGCAGTGTATGCCCTGCGCGAGTACGGCTACAAATGCGTGCCGGCCATTGGTGA<br>ACTGCGTCAACCGGTTTGGCCGGCAGAAGTTTACGGTTCCATCTCCCACTGCGGTA<br>CTACCGCGTTGGCGGTTGTGTCTCGCCAGCCGATCGGTATTGATATTGAAGAGATA<br>TTCTCTGTCCAGACGGCACGCGAGCTGACGGACAACATCATTACCCCGGCAGAGCA<br>CGAGCGTCTGGCGGACTGTGGTCTGGCGTTCAGCCTGGCGCTGACCCTGGCATTCA<br>GCGCAAAAGAGAGCGCGTTCAAGGCTTCCGAGATCCAAACCGATGCGGGCTTCCTG<br>GATTATCAAATCATCAGCTGGAACAAGCAACAGGTTATCATTCACCGTGAGAATGA<br>GATGTTTGCCGTCCATTGGCAGATTAAAGAGAAAATCGTTATCACCCTGTGCCAGC<br>ACGACTGA<u>GAATTC</u> |
| 6 | plasmid pAQ3::Pnir07_adm_carB_tesA_entD_SpecR. | AAAAGCAGAGCATTACGCTGACTTGACGGGACGGCGCAAGCTCATGACCAAAATCC<br>CTTAACGTGAGTTACGCGCGCGTCGTTCCACTGAGCGTCAGACCCCGTAGAAAAGA<br>TCAAAGGATCTTCTTGAGATCCTTTTTTTCTGCGCGTAATCTGCTGCTTGCAAACA<br>AAAAAACCACCGCTACCAGCGGTGGTTTGTTTGCCGGATCAAGAGCTACCAACTCT<br>TTTTCCGAAGGTAACTGGCTTCAGCAGAGCGCAGATACCAAATACTGTTCTTCTAG<br>TGTAGCCGTAGTTAGCCCACCACTTCAAGAACTCTGTAGCACCGCCTACATACCTC<br>GCTCTGCTAATCCTGTTACCAGTGGCTGCTGCCAGTGGCGATAAGTCGTGTCTTAC<br>CGGGTTGGACTCAAGACGATAGTTACCGGATAAGGCGCAGCGGTCGGGCTGAACGG<br>GGGGTTCGTGCACACAGCCCAGCTTGGAGCGAACGACCTACACCGAACTGAGATAC<br>CTACAGCGTGAGCTATGAGAAAGCGCCACGCTTCCCGAAGGGAGAAAGGCGGACAG<br>GTATCCGGTAAGCGGCAGGGTCGGAACAGGAGAGCGCACGAGGGAGCTTCCAGGGG<br>GAAACGCCTGGTATCTTTATAGTCCTGTCGGGTTTCGCCACCTCTGACTTGAGCGT<br>CGATTTTTGTGATGCTCGTCAGGGGGGCGGAGCCTATGGAAAAACGCCAGCAACGC<br>GGCCTTTTTACGGTTCCTGGCCTTTTGCTGGCCTTTTGCTCACATGTTCTTTCCTG<br>CGTTATCCCCTGATTCTGTGGATAACCGTATTACCGCCTTTGAGTGAGCTGATACC<br>GCTCGCCGCAGCCGAACGACCGAGCGCAGCGAGTCAGTGAGCGAGGAAGCGGAAGG<br>CGAGAGTAGGGAACTGCCAGGCATCAAACTAAGCAGAAGGCCCCTGACGGATGGCC<br>TTTTTGCGTTTCTACAAACTCTTTCTGTGTTGTAAAACGACGGCCAGTCTTAAGCT<br>CGGGCCCCCTGGGCGGTTCTGATAACGAGTAATCGTTAATCCGCAAATAACGTAAA<br>AACCCGCTTCGGCGGGTTTTTTTATGGGGGGAGTTTAGGGAAAGAGCATTTGTCAG<br>AATATTTAAGGGCGCCTGTCACTTTGCTTGATATATGAGAATTATTTAACCTTATA<br>AATGAGAAAAAAGCAACGCACTTTAAATAAGATACGTTGCTTTTTCGATTGATGAA<br>CACCTATAATTAAACTATTCATCTATTATTTATGATTTTTTGTATATACAATATTT<br>CTAGTTTGTTAAAGAGAATTAAGAAATAAATCTCGAAAATAATAAAGGGAAAATC<br>AGTTTTTGATATACAAATTATACATGTCAACGATAATACAAAATATAATACAAACT<br>ATAAGATGTTATCAGTATTTATTATGCATTTAGAATAAATTTTGTGTCGCCCTTCG<br>CTGAACCTGCAGGCGAGCATTTCAACGATGATGAATGGGACGGCGAACCCACTGAA<br>CCCGTCGCCATTGACCCAGAACCGCGCAAAGAACGGGAAAAAATTGATCTCGATCT<br>GGAGGATGAACCAGAGGAAAACCGCAAACCGCAAAAAATCAAAGTGAAGTTAGCCG<br>ATGGAAAGAGCGGGAACTCGCCCATACTCAAACCACAACTTTTTGGGATGCTGAT<br>GGTAAACCCATTTCCGCCCAAGAATTTATCGAAAAGCTATTTGGCGACCTGCCCGA<br>CCTCTTCAAGGATGAAGCCGAACTACGCACCATCTGGGGGAAACCCGATACCCGTA<br>AATCGTTCCTGACCGGACTCGCGGAAAAAGGCTACGGTGACACCCAACTGAAGGCG<br>ATCGCACGCATTGCCGAAGCGGAAAAAAGTGATGTCTATGATGTCCTGACTTGGGT |

TABLE 1-continued

| SEQ ID NO | DESCRIPTION | SEQUENCE |
|---|---|---|
| | | TGCCTACAACACCAAACCCATTAGCAGAGAAGAGCGAGTAATTAAGCATCGAGATC
TGATTTTCTCGAAGTACACCGGAAAGCAGCAAGAATTTTTAGATTTTGTCCTAGAC
CAATACATTCGAGAAGGAGTGGAGGAACTTGATCGGGGGAAACTGCCTACCCTCAT
CGAAATCAAATACCAAACCGTTAATGAAGGTTTAGTGATCTTGGGTCAGGATATCG
GTCAAGTATTCGCAGATTTTCAGGCGGATTTATATACCGAAGATGTGGCATAAAAA
AGGACGGCGATCGCCGGGGGCGTTGCCTGCCTTGAGCGGCCGCTTGTAGCAATTGC
TACTAAAAACTGCGATCGCTGCTGAAATGAGCTGGAATTTTGTCCCTCTCAGCTCA
AAAAGTATCAATGATTACTTAATGTTTGTTCTGCGCAAACTTCTTGCAGAACATGC
ATGATTTACAAAAAGTTGTAGTTTCTGTTACCAATTGCGAATCGAGAACTGCCTAA
TCTGCCGAGTATGCGATCCTTTAGCAGGAGGAAAACCATATGCAAGAACTGGCCCT
GAGAAGCGAGCTGGACTTCAATAGCGAAACCTATAAAGATGCGTATAGCCGTATTA
ACGCCATTGTGATCGAAGGCGAGCAAGAAGCATACCAAAACTACCTGGACATGGCG
CAACTGCTGCCGGAGGACGAGGCTGAGCTGATTCGTTTGAGCAAGATGGAGAACCG
TCACAAAAAGGGTTTTCAAGCGTGCGGCAAGAACCTCAATGTGACTCCGGATATGG
ATTATGCACAGCAGTTCTTTGCGGAGCTGCACGGCAATTTTCAGAAGGCTAAAGCC
GAGGGTAAGATTGTTACCTGCCTGCTCATCCAAAGCCTGATCATCGAGGCGTTTGC
GATTGCAGCCTACAACATTTACATTCCAGTGGCTGATCCGTTTGCACGTAAAATCA
CCGAGGGTGTCGTCAAGGATGAGTATACCCACCTGAATTTCGGCGAAGTTTGGTTG
AAGGAACATTTTGAAGCAAGCAAGGCGGAGTTGGAGGACGCCAACAAAGAGAACTT
ACCGCTGGTCTGGCAGATGTTGAACCAGGTCGAAAAGGATGCCGAAGTGCTGGGTA
TGGAGAAAGAGGCTCTGGTGGAGGACTTTATGATTAGCTATGGTGAGGCACTGAGC
AACATCGGCTTTTCTACGAGAGAAATCATGAAGATGAGCGCGTACGGTCTGCGTGC
AGCATAAGAGCTCGAGGAGGTTTTTACAATGACCAGCGATGTTCACGACGCCACAG
ACGGCGTCACCGAAACCGCACTCGACGACGAGCAGTCGACCCGCCGCATCGCCGAG
CTGTACGCCACCGATCCCGAGTTCGCCGCCGCCACCGTTGCCCGCCGTGGTCGA
CGCGGCGCACAAACCCGGGCTGCGGCTGGACAGAGATCCTGCAGACCCTGTTCACCG
GCTACGGTGACCGCCGGCGCTGGGATACCGCGCCCGTGAACTGGCCACCGACGAG
GGCGGGCGCACCGTGACGCGTCTGCTGCCGCGGTTCGACACCCTCACCTACGCCCA
GGTGTGGTCGCGCGTGCAAGCGGTCGCCGCGGCCCTGCGCCACAACTTCGCGCAGC
CGATCTACCCCGGCGACGCCGTCGCGACGATCGGTTTCGCGAGTCCCGATTACCTG
ACGCTGGATCTCGTATGCGCCTACCTGGGCCTCGTGAGTGTTCCGCTGCAGCACAA
CGCACCGGTCAGCCGGCTCGCCCCGATCCTGGCCGAGGTCGAACCGCGGATCCTCA
CCGTGAGCGCCGAATACCTCGACCTCGCAGTCGAATCCGTGCGGGACGTCAACTCG
GTGTCGCAGCTCGTGGTGTTCGACCATCACCCCGAGGTCGACGACCACCGCGACGC
ACTGGCCCGCGCGTGAACAACTCGCCGGCAAGGGCATCGCCGTCACCACCCTGG
ACGCGATCGCCGACGAGGGCGCCGGGCTGCCGGCCGAACCGATCTACACCGCCGAC
CATGATCAGCGCCTCGCGATGATCCTGTACACCTCGGGTTCCACCGGCGCACCCAA
GGGTGCGATGTACACCGAGGCGATGGTGGCGCGGCTGTGGACCATGTCGTTCATCA
CGGGTGACCCCACGCCGGTCATCAACGTCAACTTCATGCCGCTCAACCACCTGGGC
GGGCGCATCCCCATTTCCACCGCCGTGCAGAACGGTGGAACCAGTTACTTCGTACC
GGAATCCGACATGTCCACGCTGTTCGAGGATCTCGCGCTGGTGCGCCCGACCGAAC
TCGGCCTGGTTCCGCGCGTCGCCGACATGCTCTACCAGCACCACCTCGCCACCGTC
GACCGCCTGGTCACGCAGGGCGCCGACGAACTGACCGCCGAGAAGCAGGCCGGTGC
CGAACTGCGTGAGCAGGTGCTCGGCGGACGCGTGATCACCGGATTCGTCAGCACCG
CACCGCTGGCCGCGGAGATGAGGGCGTTCCTCGACATCACCCTGGGCGCACACATC
GTCGACGGCTACGGGCTCACCGAGACCGGCGCCGTGACACGCGACGGTGTGATCGT
GCGGCCACCGGTGATCGACTACAAGCTGATCGACGTTCCCGAACTCGGCTACTTCA
GCACCGACAAGCCCTACCCGCGTGCGCAACTGCTGGTCAGGTCGCAAACGCTGACT
CCCGGGTACTACAAGCGCCCCGAGGTCACCGCGAGCGTCTTCGACCGGGACGGCTA
CTACCACACCGGCGACGTCATGGCCGAGACCGCACCCGACCACCTGGTGTACGTGG
ACCGTCGCAACAACGTCCTCAAACTCGCGCAGGGCGAGTTCGTGGCGGTCGCCAAC
CTGGAGGCGGTGTTCTCCGGCGCGGCGCTGGTGCGCCAGATCTTCGTGTACGGCAA
CAGCGAGCGCAGTTTCCTTCTGGCCGTGGTGGTCCCGACGCCGGAGGCGCTCGAGC
AGTACGATCCGGCCGCGCTCAAGGCCGCGCTGGCCGACTCGCTGCAGCGCACCGCA
CGCGACGCCGAACTGCAATCCTACGAGGTGCCGGCCGATTTCATCGTCGAGACCGA
GCCGTTCAGCGCCGCCAACGGGCTGCTGTCGGGTGTCGGAAAACTGCTGCGGCCCA
ACCTCAAAGACCGCTACGGGCAGCGCCTGGAGCAGATGTACGCCGATATCGCGGCC
ACGCAGGCCAACCAGTTGCGCGAACTGCGGCGCGCGGCCGCCACACAACCGGTGAT
CGACACCCTCACCCAGGCCGCTGCCACGATCCTCGGCACCGGGAGCGAGGTGGCAT
CCGACGCCCACTTCACCGACCTGGGCGGGATTCCCTGTCGGCGCTGACACTTTCG
AACCTGCTGAGCGATTTCTTCGGTTTCGAAGTTCCCGTCGGCACCATCGTGAACCC
GGCCACCAACCTCGCCCAACTCGCCCAGCACATCGAGGCGCAGCGCACCGCGGGTG
ACCGCAGGCCGAGTTTCACCACCGTGCACGGCGCGGACGCCATCCGACGATCCGGGCG
AGTGAGCTGACCCTGGACAAGTTCATCGACGCCGAAACGCTCCGGGCCGCACCGGG
TCTGCCCAAGGTCACCACCGAGCCACGGACGGTGTTGCTCTCGGGCGCCAACGGCT
GGCTGGGCCGGTTCCTCACGTTGCAGTGGCTGGAACGCCTGGCACCTGTCGGCGGC
ACCCTCATCACGATCGTGCGGGGCCGCGACGACGCCGCGGCCCGCGCACGGCTGAC
CCAGGCCTACGACACCGATCCCGAGTTGTCCCGCCGCTTCGCCGAGCTGGCCGACC
GCCACCTGCGGGTGGTCGCCGGTGACATCGGCGACCCGAATCTGGGCCTCACACCC
GAGATCTGGCACCGGCTCGCCGCCGAGGTCGACCTGGTGGTGCATCCGGCAGCGCT
GGTCAACCACCTGCTCCCCTACCGGCAGCTGTTCGGCCCCAACCGTCGTGGGCACGG
CCGAGGTGATCAAGCTGGCCCTCACCGAACGGATCAAGCCCGTCACGTACCTGTCC
ACCGTGTCGGTGGCCATGGGGATCCCCGACTTCGAGGAGGACGGCGACATCCGGAC
CGTGAGCCCGGTGCGCCCGCTCGACGGCGGATACGCCAACGGCTACGGCAACAGCA
AGTGGGCCGGCGAGGTGCTGCTGCGGGAGGCCCACGATCTGTGCGGGCTGCCCGTG
GCGACGTTCCGCTCGGACATGATCCTGGCGCATCCGCGCTACCGCGGTCAGGTCAA |

TABLE 1-continued

| SEQ ID NO | DESCRIPTION | SEQUENCE |
|---|---|---|
| | | CGTGCCAGACATGTTCACGCGACTCCTGTTGAGCCTCTTGATCACCGGCGTCGCGC
CGCGGTCGTTCTACATCGGAGACGGTGAGCGCCCGCGGGCGCACTACCCCGGCCTG
ACGGTCGATTTCGTGGCCGAGGCGGTCACGACGCTCGGCGCGCAGCAGCGCGAGGG
ATACGTGTCCTACGACGTGATGAACCCGCACGACGACGGGATCTCCCTGGATGTGT
TCGTGGACTGGCTGATCCGGGCGGGCCATCCGATCGACCGGGTCGACGACTACGAC
GACTGGGTGCGTCGGTTCGAGACCGCGTTGACCGCGCTTCCCGAGAAGCGCCGCGC
ACAGACCGTACTGCCGCTGCTGCACGCGTTCCGCGCTCCGCAGGCACCGTTGCGCG
GCGCACCCGAACCCACGGAGGTGTTCCACGCCGCGGTGCGCACCGCGAAGGTGGGC
CCGGGAGACATCCCGCACCTCGACGAGGCGCTGATCGACAAGTACATACGCGATCT
GCGTGAGTTCGGTCTGATCTGAGGTACCAGGAGGTTTTTACAATGGCTGATACTTT
GTTGATTTTGGGTGATTCTCTCTCTGCAGGCTACCGTATGTCCGCGAGCGCGGCAT
GGCCGGCTCTGCTGAACGATAAGTGGCAGAGCAAGACCAGCGTGGTCAATGCGAGC
ATCAGCGGCGATACCAGCCAGCAGGGTCTGGCACGTCTGCCAGCGCTGCTGAAGCA
ACACCAGCCGCGTTGGGTGCTGGTTGAACTGGGCGGCAATGACGGTCTGCGTGGTT
TTCAGCCGCAGCAGACCGAACAAACGTTGCGTCAGATTCTGCAGGACGTCAAGGCG
GCTAACGCGGAACCGCTGCTGATGCAAATTCGCCTGCCGGCGAATTATGGTCGTCG
TTACAACGAGGCTTTCAGCGCCATTTATCCTAAACTGGCTAAAGAGTTTGACGTGC
CGCTGCTGCCGTTCTTCATGGAAGAGGTCTACCTGAAACCGCAATGGATGCAAGAC
GACGGTATTCATCCGAATCGTGATGCACAACCTTTCATCGCGGATTGGATGGCGAA
GCAATTGCAACCGCTGGTGAACCATGACTCGTAAAAGCTTGTTGCTGCATGCAGGA
GGTTTTTACAATGAAAACGACCCACACCAGCTTACCATTTGCCGGCCACACGTTAC
ATTTCGTCGAATTTGATCCGGCGAACTTTTGTGAACAAGACCTGTTGTGGCTGCCG
CATTATGCCCAGCTGCAGCACGCAGGCCGTAAGCGTAAAACTGAACATCTGGCCGG
TCGCATTGCGGCAGTGTATGCCCTGCGCGAGTACGGCTACAAATGCGTGCCGGCCA
TTGGTGAACTGCGTCAACCGGTTTGGCCGGCAGAAGTTTACGGTTCCATCTCCCAC
TGCGGTACTACCGCGTTGGCGGTTGTGTCTCGCCAGCCGATCGGTATTGATATTGA
AGAGATATTCTCTGTCCAGACGGCACGCGAGCTGACGGACAACATCATTACCCCGG
CAGAGCACGAGCGTCTGGCGGACTGTGGTCTGGCGTTCAGCCTGGCGCTGACCCTG
GCATTCAGCGCAAAAGAGAGCGCGTTCAAGGCTTCCGAGATCCAAACCGATGCGGG
CTTCCTGGATTATCAAATCATCAGCTGGAACAAGCAACAGGTTATCATTCACCGTG
AGAATGAGATGTTTGCCGTCCATTGGCAGATTAAAGAGAAATCGTTATCACCCTG
TGCCAGCACGACTGAGAATTCGGTTTTCCGTCCTGTCTTGATTTTCAAGCAAACAA
TGCCTCCGATTTCTAATCGGAGGCATTTGTTTTTGTTTATTGCAAAAACAAAAAAT
ATTGTTACAAATTTTTACAGGCTATTAAGCCTACCGTCATAAATAATTTGCCATTT
ACTAGTTTTTAATTAACCAGAACCTTGACCGAACGCAGCGGTGGTAACGGCGCAGT
GGCGGTTTTCATGGCTTGTTATGACTGTTTTTTTGGGGTACAGTCTATGCCTCGGG
CATCCAAGCAGCAAGCGCGTTACGCCGTGGGTCGATGTTTGATGTTATGGAGCAGC
AACGATGTTACGCAGCAGGGCAGTCGCCCTAAAACAAAGTTAAACATCATGAGGGA
AGCGGTGATCGCCGAAGTATCGACTCAACTATCAGAGGTAGTTGGCGTCATCGAGC
GCCATCTCGAACCGACGTTGCTGGCCGTACATTTGTACGGCTCCGCAGTGGATGGC
GGCCTGAAGCCACACAGTGATATTGATTTGCTGGTTACGGTGACCGTAAGGCTTGA
TGAAACAACGCGGCGAGCTTTGATCAACGACCTTTTGGAAACTTCGGCTTCCCCTG
GAGAGAGCGAGATTCTCCGCGCTGTAGAAGTCACCATTGTTGTGCACGACGACATC
ATTCCGTGGCGTTATCCAGCTAAGCGCGAACTGCAATTTGGAGAATGGCAGCGCAA
TGACATTCTTGCAGGTATCTTCGAGCCAGCCACGATCGACATTGATCGGCTATCT
TGCTGACAAAAGCAAGAGAACATAGCGTTGCTTGGATAGGTCCAGCGGCGGAGGAA
CTCTTTGATCCGGTTCCTGAACAGGATCTATTTGAGGCGCTAAATGAAACCTTAAC
GCTATGGAACTCGCCGCCCGACTGGGCTGGCGATGAGCGAAATGTAGTGCTTACGT
TGTCCCGCATTTGGTACAGCGCAGTAACCGGCAAAATCGCGCCGAAGGATGTCGCT
GCCGACTGGGCAATGGAGCGCCTGCCGGCCCAGTATCAGCCCGTCATACTTGAAGC
TAGACAGGCTTATCTTGGACAAGAAGAAGATCGCTTGGCCTCGCGCGCAGATCAGT
TGGAAGAATTTGTCCACTACGTGAAAGGCGAGATCACCAAGGTAGTCGGCAAATAA
TGTCTAACAATTCGTTCAAGCCGACGCCGCTTCGCGGCGCGGCTTAACTCAAGCGT
TAGATGCACTAAGCACATAATTGCTCACAGCCAAACTATCAGGTCAAGTCTGCTTT
TATTATTTTTAAGCGTGCATAATAAGCCCTACACAAATTGGGAGATATATCATGAG
GCGCGCCACGAGAAAGAGTTATGACAAATTAAAATTCTGACTCTTAGATTATTTCC
AGAGAGGCTGATTTTCCCAATCTTTGGGAAAGCCTAAGTTTTTAGATTCTATTTCT
GGATACATCTCAAAAGTTCTTTTTAAATGCTGTGCAAAATTATGCTCTGGTTTAAT
TCTGTCTAAGAGATACTGAATACAACATAAGCCAGTGAAAATTTTACGGCTGTTTC
TTTGATTAATATCCTCCAATACTTCTCTAGAGAGCCATTTTCCTTTTAACCTATCA
GGCAATTTAGGTGATTCTCCTAGCTGTATATTCCAGAGCCTTGAATGATGAGCGCA
AATATTTCTAATATGCGACAAAGACCGTAACCAAGATATAAAAAACTTGTTAGGTA
ATTGGAAATGAGTATGTATTTTTTGTCGTGTCTTAGATGGTAATAAATTTGTGTAC
ATTCTAGATAACTGCCCAAAGGCGATTATCTCCAAAGCCATATATGACGGCGGTAG
TAGAGGATTTGTGTACTTGTTTCGATAATGCCCGATAAATTCTTCTACTTTTTTAG
ATTGGCAATATTGAGTAATCGAATCGATTAATTCTTGATGCTTCCCAGTGTCATAA
AATAAACTTTTATTCAGATACCAATGAGGATCATAATCATGGGAGTAGTGATAAAT
CATTTGAGTTCTGACTGCTACTTCTATCGACTCCGTAGCATTAAAAATAAGCATTC
TCAAGGATTTATCAAACTTGTATAGATTTGGCCGGCCCGTCAAAAGGGCGACACCC
CATAATTAGCCCGGGCGAAAGGCCCAGTCTTTCGACTGAGCCTTTCGTTTTATTTG
ATGCCTGGCAGTTCCCTACTCTCGCATGGGGAGTCCCCACACTACCATCGGCGCTA
CGGCGTTTCACTTCTGAGTTCGGCATGGGGTCAGGTGGGACCACCGCGCTACTGCC
GCCAGGCAAACAAGGGGTGTTATGAGCCATATTCAGGTATAAATGGGCTCGCGATA
ATGTTCAGAATTGGTTAATTGGTTGTAACACTGACCCCTATTTGTTTATTTTCTA
AATACATTCAAATATGTATCCGCTCATGAGACAATAACCCTGATAAATGCTTCAAT
AATATTGAAAAAGGAAGAATATGAGTATTCAACATTTCCGTGTCGCCCTTATTCCC |

| SEQ ID NO | DESCRIPTION | SEQUENCE |
|---|---|---|
| | | TTTTTTGCGGCATTTTGCCTTCCTGTTTTTGCTCACCCAGAAACGCTGGTGAAAGT<br>AAAAGATGCTGAAGATCAGTTGGGTGCACGAGTGGGTTACATCGAACTGGATCTCA<br>ACAGCGGTAAGATCCTTGAGAGTTTTCGCCCCGAAGAACGTTTTCCAATGATGAGC<br>ACTTTTAAAGTTCTGCTATGTGGCGCGGTATTATCCCGTATTGACGCCGGGCAAGA<br>GCAACTCGGTCGCCGCATACACTATTCTCAGAATGACTTGGTTGAGTACTCACCAG<br>TCACAGAAAAGCATCTTACGGATGGCATGACAGTAAGAGAATTATGCAGTGCTGCC<br>ATAACCATGAGTGATAACACTGCGGCCAACTTACTTCTGACAACGATCGGAGGACC<br>GAAGGAGCTAACCGCTTTTTTGCACAACATGGGGGATCATGTAACTCGCCTTGATC<br>GTTGGGAACCGGAGCTGAATGAAGCCATACCAAACGACGAGCGTGACACCACGATG<br>CCTGTAGCGATGGCAACAACGTTGCGCAAACTATTAACTGGCGAACTACTTACTCT<br>AGCTTCCCGGCAACAATTAATAGACTGGATGGAGGCGGATAAAGTTGCAGGACCAC<br>TTCTGCGCTCGGCCCTTCCGGCTGGCTGGTTTATTGCTGATAAATCCGGAGCCGGT<br>GAGCGTGGTTCTCGCGGTATCATCGCAGCGCTGGGGCCAGATGGTAAGCCCTCCCG<br>TATCGTAGTTATCTACACGACGGGGAGTCAGGCAACTATGGATGAACGAAATAGAC<br>AGATCGCTGAGATAGGTGCCTCACTGATTAAGCATTGGT |
| 7 | codon-optimized *Cuphea hookeriana* leaderless fatB2 gene. | <u>GGTACCAGGAGGTTTTTAC</u>ATGGACCGTAAAAGCAAGCGTCCGGACATGCTGGTTG<br>ATTCCTTTGGTCTGGAAAGCACCGTGCAGGACGGTCTGGTTTTCCGTCAGTCTTTC<br>TCCATTCGTAGCTATGAGATTGGTACTGATCGTACCGCCTCTATCGAAACCCTGAT<br>GAATCACCTGCAAGAAACCTCTCTGAACCATTGTAAGTCTACTGGCATCCTGCTGG<br>ACGGTTTCGTACCCTGGAGATGTGCAAACGCGACCTGATTTGGGTAGTGATC<br>AAAATGCAGATCAAAGTTAACCGTTATCCGGCATGGGGTGATACCGTTGAAATCAA<br>CACCCGCTTTTCTCGTCTGGGCAAAATCGGTATGGGCCGTGACTGGCTGATCTCTG<br>ACTGTAACACTGGTGAAATTCTGGTTCGTGCTACTAGCGCATACGCGATGATGAAC<br>CAGAAAAACCCGTCGCCTGAGCAAGCTGCCGTACGAGGTCCACCAGGAGATTGTTCC<br>GCTGTTTGTAGACAGCCCAGTGATTGAGGATTCTGACCTGAAAGTGCATAAATTCA<br>AAGTGAAGACCGGTGACAGCATCCAAAAAGGCCTGACCCCAGGTTGGAACGATCTG<br>GACGTTAACCAGCACGTTTCCAACGTGAAGTATATCGGTTGGATTCTGGAGAGCAT<br>GCCGACCGAGGTCCTGGAAACCCAGGAGCTGTGTTCCCTGGCGCTGGAGTACCGCC<br>GTGAGTGCGGCCGTGACAGCGTGCTGGAGTCTGTGACCGCTATGGACCCAAGCAAA<br>GTTGGTGTTCGTAGCCAGTACCAGCACCTGCTGCGTCTGGAAGACGGTACTGCTAT<br>CGTGAACGGTGCAACTGAATGGCGTCCTAAAAACGCGGGTGCAAACGGTGCTATCA<br>GCACCGGTAAAACCTCTAACGGTAACTCCGTGAGCTAA<u>AAGCTT</u> |
| 8 | plasmid pAQ3::P(nir07)_adm_carB_fatB2_entD_SpecR. | AAAAGCAGAGCATTACGCTGACTTGACGGGACGGCGCAAGCTCATGACCAAAATCC<br>CTTAACGTGAGTTACGCGCGCGTCGTTCCACTGAGCGTCAGACCCCGTAGAAAAGA<br>TCAAAGGATCTTCTTGAGATCCTTTTTTTCTGCGCGTAATCTGCTGCTTGCAAACA<br>AAAAAACCACCGCTACCAGCGGTGGTTTGTTTGCCGGATCAAGAGCTACCAACTCT<br>TTTTCCGAAGGTAACTGGCTTCAGCAGAGCGCAGATACCAAATACTGTTCTTCTAG<br>TGTAGCCGTAGTTAGCCCACCACTTCAAGAACTCTGTAGCACCGCCTACATACCTC<br>GCTCTGCTAATCCTGTTACCAGTGGCTGCTGCCAGTGGCGATAAGTCGTGTCTTAC<br>CGGGTTGGACTCAAGACGATAGTTACCGGATAAGGCGCAGCGGTCGGGCTGAACGG<br>GGGGTTCGTGCACACAGCCCAGCTTGGAGCGAACGACCTACACCGAACTGAGATAC<br>CTACAGCGTGAGCTATGAGAAAGCGCCACGCTTCCCGAAGGGAGAAAGGCGGACAG<br>GTATCCGGTAAGCGGCAGGGTCGGAACAGGAGAGCGCACGAGGGAGCTTCCAGGGG<br>GAAACGCCTGGTATCTTTATAGTCCTGTCGGGTTTCGCCACCTCTGACTTGAGCGT<br>CGATTTTTGTGATGCTCGTCAGGGGGCGGAGCCTATGGAAAAACGCCAGCAACGC<br>GGCCTTTTTACGGTTCCTGGCCTTTTGCTGGCCTTTTGCTCACATGTTCTTTCCTG<br>CGTTATCCCCTGATTCTGTGGATAACCGTATTACCGCCTTTGAGTGAGCTGATACC<br>GCTCGCCGCAGCCGAACGACCGAGCGCAGCGAGTCAGTGAGCGAGGAAGCGGAAGG<br>CGAGAGTAGGGAACTGCCAGGCATCAAACTAAGCAGAAGGCCCCTGACGGATGGCC<br>TTTTTGCGTTTCTACAAACTCTTTCTGTGTTGTAAAACGACGGCCAGTCTTAAGCT<br>CGGGCCCCTGGGCGGTTCTGATAACGAGTAATCGTTAATCCGCAAATAACGTAAA<br>AACCCGCTTCGGCGGGTTTTTTTATGGGGGGAGTTTAGGGAAAGAGCATTTGTCAG<br>AATATTTAAGGGCGCCTGTCACTTTGCTTGATATATGAGAATTATTTAACCTTATA<br>AATGAGAAAAAAGCAACGCACTTTAAATAAGATACGTTGCTTTTTCGATTGATGAA<br>CACCTATAATTAAACTATTCATCTATTATTTATGATTTTTTGTATATACAATATTT<br>CTAGTTTGTTAAAGAGAATTAAGAAAATAAATCTCGAAAATAATAAAGGGAAAATC<br>AGTTTTTGATATCAAAATTATACATGTCAACGATAATACAAAATATAATACAAACT<br>ATAAGATGTTATCAGTATTTATTATGCATTTAGAATAAATTTTGTGTCGCCCTTCG<br>CTGAACCTGCAGGCGAGCATTTCAACGATGATGAATGGGACGGCGAACCCACTGAA<br>CCCGTCGCCATTGACCCAGAACCGCGCAAAGAACGGGAAAAAATTGATCTCGATCT<br>GGAGGATGAACCAGAGGAAAACCGCAAACCGCAAAAAATCAAAGTGAAGTTAGCCG<br>ATGGGAAAGAGCGGGAACTCGCCCATACTCAAACCACAACTTTTTGGGATGCTGAT<br>GGTAAACCCATTTCCGCCCAAGAATTTATCGAAAAGCTATTTGGCGACCTGCCCGA<br>CCTCTTCAAGGATGAAGCCGAACTACGCACCATCTGGGGGAAACCCGATACCCGTA<br>AATCGTTCCTGACCGGACTCGCGGAAAAAGGCTACGGTGACACCCAACTGAAGGCG<br>ATCGCACGCATTGCCGAAGCGGAAAAAAGTGATGTCTATGATGTCCTGACTTGGGT<br>TGCCTACAACACCAAACCCATTAGCAGAGAAGAGCGAGTAATTAAGCATCGAGATC<br>TGATTTTCTCGAAGTACACCGGAAAGCAGCAAGAATTTTTAGATTTTGTCCTAGAC<br>CAATACATTCGAGAAGGAGTGGAGGAACTTGATCGGGGGAAACTGCCTACCCTCAT<br>CGAAATCAAATACCAAACCGTTAATGAAGGTTTAGTGATCTTGGGTCAGGATATCG<br>GTCAAGTATTCGCAGATTTCAGGCGGATTTATATACCGAAGATGTGGCATAAAAA<br>AGGACGGCGATCGCCGGGGCGTTGCCTGCCTTGAGCGGCGCTTGTAGCAATTGC<br>TACTAAAAACTGCGATCGCTGCTGAAATGAGCTGGAATTTTTGTCCCTCTCAGCTCA<br>AAAGTATCAATGATTACTTAATGTTTGTTCTGCGCAAACTTCTTGCAGAACATGC |

TABLE 1-continued

| SEQ ID NO | DESCRIPTION | SEQUENCE |
|---|---|---|
| | | ATGATTTACAAAAAGTTGTAGTTTCTGTTACCAATTGCGAATCGAGAACTGCCTAA
TCTGCCGAGTATGCGATCCTTTAGCAGGAGGAAAACCATATGCAAGAACTGGCCCT
GAGAAGCGAGCTGGACTTCAATAGCGAAACCTATAAAGATGCGTATAGCCGTATTA
ACGCCATTGTGATCGAAGGCGAGCAAGAAGCATACCAAAACTACCTGGACATGGCG
CAACTGCTGCCGGAGGACGAGGCTGAGCTGATTCGTTTGAGCAAGATGGAGAACCG
TCACAAAAAGGGTTTTCAAGCGTGCGGCAAGAACCTCAATGTGACTCCGGATATGG
ATTATGCACAGCAGTTCTTTGCGGAGCTGCACGGCAATTTTCAGAAGGCTAAAGCC
GAGGGTAAGATTGTTACCTGCCTGCTCATCCAAAGCCTGATCATCGAGGCGTTTGC
GATTGCAGCCTACAACATTTACATTCCAGTGGCTGATCCGTTTGCACGTAAAATCA
CCGAGGGTGTCGTCAAGGATGAGTATACCCACCTGAATTTCGGCGAAGTTTGGTTG
AAGGAACATTTTGAAGCAAGCAAGGCGGAGTTGGAGGACGCCAACAAAGAGAACTT
ACCGCTGGTCTGGCAGATGTTGAACCAGGTCGAAAAGGATGCCGAAGTGCTGGGTA
TGGAGAAAGAGGCTCTGGTGGAGGACTTTATGATTAGCTATGGTGAGGCACTGAGC
AACATCGGCTTTTCTACGAGAGAAATCATGAAGATGAGCGCGTACGGTCTGCGTGC
AGCATAAGAGCTCGAGGAGGTTTTTACAATGACCAGCGATGTTCACGACGCCACAG
ACGGCGTCACCGAAACCGCACTCGACGACGAGCAGTCGACCCGCCGCATCGCCGAG
CTGTACGCCACCGATCCCGAGTTCGCCGCCGCCACCGTTGCCCGCCGTGGTCGA
CGCGGCGCACAAACCCGGGCTGCGGCTGGCAGAGATCCTGCAGACCCTGTTCACCG
GCTACGGTGACCGCCCGGCGCTGGGATACCGCGCCCGTGAACTGGCCACCGACGAG
GGCGGGCGCACCGTGACGCGTCTGCTGCCGCGGTTCGACACCCTCACCTACGCCCA
GGTGTGGTCGCGCGTGCAAGCGGTCGCCGCGCCCTGCGCCACAACTTCGCGCAGC
CGATCTACCCCGGCGACGCCGTCGCGACGATCGGTTTCGCGAGTCCCGATTACCTG
ACGCTGGATCTCGTATGCGCCTACCTGGGCCTCGTGAGTGTTCCGCTGCAGCACAA
CGCACCGGTCAGCCGGCTCGCCCCGATCCTGGCCGAGGTCGAACCGCGGATCCTCA
CCGTGAGCGCCGAATACCTCGACCTCGCAGTCGAATCCGTGCGGGACGTCAACTCG
GTGTCGCAGCTCGTGGTGTTCGACCATCACCCCGAGGTCGACGACCACCGCGACGC
ACTGGCCCGCGCGTGAACAACTCGCCGGCAAGGGCATCGCCGTCACCACCCTGG
ACGCGATCGCCGACGAGGGCGCCGGGCTGCCGGCCGAACCGATCTACACCGCCGAC
CATGATCAGCGCCTCGCGATGATCCTGTACACCTCGGGTTCCACCGGCGCACCCAA
GGGTGCGATGTACACCGAGGCGATGGTGGCGCGGCTGTGGACCATGTCGTTCATCA
CGGGTGACCCCACGCCGGTCATCAACGTCAACTTCATGCCGCTCAACCACCTGGGC
GGGCGCATCCCCATTTCCACCGCCGTGCAGAACGGTGGAACCAGTTACTTCGTACC
GGAATCCGACATGTCCACGCTGTTCGAGGATCTCGCGCTGGTGCGCCCGACCGAAC
TCGGCCTGGTTCCGCGCGTCGCCGACATGCTCTACCAGCACCACCTCGCCACCGTC
GACCGCCTGGTCACGCAGGGCGCCGACGAACTGACCGCCGAGAAGCAGGCCGGTGC
CGAACTGCGTGAGCAGGTGCTCGGCGGACGCGTGATCACCGGATTCGTCAGCACCG
CACCGCTGGCCGCGGAGATGAGGGCGTTCCTCGACATCACCCTGGGCGCACACATC
GTCGACGGCTACGGGCTCACCGAGACCGGCGCCGTGACACGCGACGGTGTGATCGT
GCGGCCACCGGTGATCGACTACAAGCTGATCGACGTTCCCGAACTCGGCTACTTCA
GCACCGACAAGCCCTACCCGCGTGGCGAACTGCTGGTCAGGTCGCAAACGCTGACT
CCCGGGTACTACAAGCGCCCCGAGGTCACCGCGAGCGTCTTCGACCGGGACGGCTA
CTACCACACCGGCGACGTCATGGCCGAGACCGCACCCGACCACCTGGTGTACGTGG
ACCGTCGCAACAACGTCCTCAAACTCGCGCAGGGCGAGTTCGTGGCGGTCGCCAAC
CTGGAGGCGGTGTTCTCCGGCGCGGCGCTGGTGCGCCAGATCTTCGTGTACGGCAA
CAGCGAGCGCAGTTTCCTTCTGGCCGTGGTGGTCCCGACGCCGGAGGCGCTCGAGC
AGTACGATCCGGCCGCGCTCAAGGCCGCGCTGGCCGACTCGCTCGCAGCGCACCGA
CGCGACGCCGAACTGCAATCCTACGAGGTGCCGGCCGATTTCATCGTCGAGACCGA
GCCGTTCAGCGCCGCCAACGGGCTGCTGTCGGGTGTCGGAAAACTGCTGCGGCCCA
ACCTCAAAGACCGCTACGGGCAGCGCCTGGAGCAGATGTACGCCGATATCGCGGCC
ACGCAGGCCAACCAGTTGCGCGAACTGCGGCGCGGCCGCCACAACCGGTGAT
CGACACCCTCACCCAGGCCGCTGCCACGATCCTCGGCACCGGGAGCGAGGTGGCAT
CCGACGCCCACTTCACCGACCTGGGCGGGGATTCCCTGTCGGCGCTGACACTTTCG
AACCTGCTGAGCGATTTCTTCGGTTTCGAAGTTCCCGTCGGCACCATCGTGAACCC
GGCCACCAACCTCGCCCAACTCGCCCAGCACATCGAGGCGCAGCGCACCGCGGGTG
ACCGCAGGCCGAGTTTCACCACCGTGCACGGCGCGGACGCCACCGAGATCCGGGCG
AGTGAGCTGACCCTGGACAAGTTCATCGACGCCGAAACGCTCCGGGCCGCACCGGG
TCTGCCCAAGGTCACCACCGAGCCACGGACGGTGTTGCTCTCGGGCGCCAACGGCT
GGCTGGGCCGGTTCCTCACGTTGCAGTGGCTGGAACGCCTGGCACCTGTCGGCGGC
ACCCTCATCACGATCGTGCGGGGCCGCGACGACGCCGCGGCCCGCGCACGGCTGAC
CCAGGCCTACGACACCGATCCCGAGTTGTCCCGCCGCTTCGCCGAGCTGGCCGACC
GCCACCTGCGGGTGGTCGCCGGTGACATCGGCGACCCGAATCTGGGCCTCACACCC
GAGATCTGGCACCGGCTCGCCGCCGAGGTCGACCTGGTGGTGCATCCGGCAGCGCT
GGTCAACCACGTGCTCCCCTACCGGCAGCTGTTCGGCCCCAACGTCGTGGGCACGG
CCGAGGTGATCAAGCTGGCCCTCACCGAACGGATCAAGCCCGTCACGTACCTGTCC
ACCGTGTCGGTGGCCATGGGGATCCCCGACTTCGAGGAGGACGGCGACATCCGGAC
CGTGAGCCCGGTGCGCCCGCTCGACGCGGATACGCCAACGGCTACGGCAACAGCA
AGTGGGCCGGCGAGGTGCTGCTGCGGGAGGCCCACGATCTGTGCGGGCTGCCCGTG
GCGACGTTCCGCTCGGACATGATCCTGGCGCATCCGCGCTACCGCGGTCAGGTCAA
CGTGCCAGACATGTTCACGCGACTCCTGTTGAGCCTCTTGATCACCGGCGTCGCGC
CGCGGTCGTTCTACATCGGAGACGGTGAGCGCCCGCGGGCGCACTACCCCGGCCTG
ACGGTCGATTTCGTGGCCGAGGCGGTCACGACGCTCGGCGCCGCAGCGCGCAGGGG
ATACGTGTCCTACGACGTGATGAACCCGCACGACGACGGGATCTCCCTGGATGTGT
TCGTGGACTGGCTGATCCGGGCGGGCCATCCGATCGACCGGGTCGACGACTACGAC
GACTGGGTGCGTCGGTTCGAGACCGCGTTGACCGCGCTTCCCGAGAAGCGCCGCGC
ACAGACCGTACTGCCGCTGCTGCACGCGTTCCGCGCTCCGCAGGCACCGTTGCGCG
GCGCACCCGAACCCACGGAGGTGTTCCACGCCGCGGTGCGCACCGCGAAGGTGGGC |

TABLE 1-continued

| SEQ ID NO | DESCRIPTION | SEQUENCE |
|---|---|---|
| | | CCGGGAGACATCCCGCACCTCGACGAGGCGCTGATCGACAAGTACATACGCGATCT |
| | | GCGTGAGTTCGGTCTGATCTGAGGTACCAGGAGGTTTTTACATGGACCGTAAAAGC |
| | | AAGCGTCCGGACATGCTGGTTGATTCCTTTGGTCTGGAAAGCACCGTGCAGGACGG |
| | | TCTGGTTTTCCGTCAGTCTTTCTCCATTCGTAGCTATGAGATTGGTACTGATCGTA |
| | | CCGCCTCTATCGAAACCCTGATGAATCACCTGCAAGAAACCTCTCTGAACCATTGT |
| | | AAGTCTACTGGCATCCTGCTGGACGGTTTCGGTCGTACCCTGGAGATGTGCAAACG |
| | | CGACCTGATTTGGGTAGTGATCAAAATGCAGATCAAAGTTAACCGTTATCCGGCAT |
| | | GGGGTGATACCGTTGAAATCAACACCCGCTTTTCTCGTCTGGGCAAAATCGGTATG |
| | | GGCCGTGACTGGCTGATCTCTGACTGTAACACTGGTGAAATTCTGGTTCGTGCTAC |
| | | TAGCGCATACGCGATGATGAACCAGAAAACCCGTCGCCTGAGCAAGCTGCCGTACG |
| | | AGGTCCACCAGGAGATTGTTCCGCTGTTTGTAGACAGCCCAGTGATTGAGGATTCT |
| | | GACCTGAAAGTGCATAAATTCAAAGTGAAGACCGGTGACAGCATCCAAAAAGGCCT |
| | | GACCCCAGGTTGGAACGATCTGGACGTTAACCAGCACGTTTCCAACGTGAAGTATA |
| | | TCGGTTGGATTCTGGAGAGCATGCCGACCGAGGTCCTGGAAACCCAGGAGCTGTGT |
| | | TCCCTGGCGCTGGAGTACCGCCGTGAGTGCGCCGTGACAGCGTGCTGGAGTCTGT |
| | | GACCGCTATGGACCCAAGCAAAGTTGGTGTTCGTAGCCAGTACCAGCACCTGCTGC |
| | | GTCTGGAAGACGGTACTGCTATCGTGAACGGTGCAACTGAATGGCGTCCTAAAAAC |
| | | GCGGGTGCAAACGGTGCTATCAGCACCGGTAAAACCTCTAACGGTAACTCCGTGAG |
| | | CTAAAAGCTTGTTGCTGCATGCAGGAGGTTTTTACAATGAAAACGACCCACACCAG |
| | | CTTACCATTTGCCGGCCACACGTTACATTTCGTCGAATTTGATCCGGCGAACTTTT |
| | | GTGAACAAGACCTGTTGTGGCTGCCGCATTATGCCCAGCTGCAGCACGCAGGCCGT |
| | | AAGCGTAAAACTGAACATCTGGCCGGTCGCATTGCGGCAGTGTATGCCCTGCGCGA |
| | | GTACGGCTACAAATGCGTGCCGGCCATTGGTGAACTGCGTCAACCGGTTTGGCCGG |
| | | CAGAAGTTTACGGTTCCATCTCCCACTGCGGTACTACCGCGTTGGCGGTTGTGTCT |
| | | CGCCAGCCGATCGGTATTGATATTGAAGAGATATTCTCTGTCCAGACGGCACGCGA |
| | | GCTGACGGACAACATCATTACCCCGGCAGAGCACGAGCGTCTGGCGGACTGTGGTC |
| | | TGGCGTTCAGCCTGGCGCTGACCCTGGCATTCAGCGCAAAAGAGAGCGCGTTCAAG |
| | | GCTTCCGAGATCCAAACCGATGCGGGCTTCCTGGATTATCAAATCATCAGCTGGAA |
| | | CAAGCAACAGGTTATCATTCACCGTGAGAATGAGATGTTTGCCGTCGTCATTGGCAGA |
| | | TTAAAGAGAAAATCGTTATCACCCTGTGCCAGCACGACTGAGAATTCGGTTTTCCG |
| | | TCCTGTCTTGATTTTCAAGCAAACAATGCCTCCGATTTCTAATCGGAGGCATTTGT |
| | | TTTTGTTTATTGCAAAAACAAAAAATATTGTTACAAATTTTTACAGGCTATTAAGC |
| | | CTACCGTCATAAATAATTTGCCATTTACTAGTTTTTAATTAACCAGAACCTTGACC |
| | | GAACGCAGCGGTGGTAACGGCGCAGTGGCGGTTTTCATGGCTTGTTATGACTGTTT |
| | | TTTTGGGGTACAGTCTATGCCTCGGGCATCCAAGCAGCAAGCGCGTTACGCCGTGG |
| | | GTCGATGTTTGATGTTATGGAGCAGCAACGATGTTACGCAGCAGGGCAGTCGCCCT |
| | | AAAACAAAGTTAAACATCATGAGGGAAGCGGTGATCGCCGAAGTATCGACTCAACT |
| | | ATCAGAGGTAGTTGGCGTCATCGAGCGCCATCTCGAACCGACGTTGCTGGCCGTAC |
| | | ATTTGTACGGCTCCGCAGTGGATGGCGGCCTGAAGCCACACAGTGATATTGATTTG |
| | | CTGGTTACGGTGACCGTAAGGCTTGATGAAACAACCGGCGAGCTTTGATCAACGA |
| | | CCTTTTGGAAACTTCGGCTTCCCCTGGAGAGAGCGAGATTCTCCGCGCTGTAGAAG |
| | | TCACCATTGTTGTGCACGACGACATCATTCCGTGGCGTTATCCAGCTAAGCGCGAA |
| | | CTGCAATTTGGAGAATGGCAGCGCAATGACATTCTTGCAGGTATCTTCGAGCCAGC |
| | | CACGATCGACATTGATCTGGCTATCTTGCTGACAAAAGCAAGAGAACATAGCGTTG |
| | | CCTTGGTAGGTCCAGCGGCGGAGGAACTCTTTGATCCGGTTCCTGAACAGGATCTA |
| | | TTTGAGGCGCTAAATGAAACCTTAACGCTATGGAACTCGCCGCCCGACTGGGCTGG |
| | | CGATGAGCGAAATGTAGTGCTTACGTTGTCCCGCATTTGGTACAGCGCAGTAACCG |
| | | GCAAAATCGCGCCGAAGGATGTCGCTGCCGACTGGGCAATGGAGCGCCTGCCGGCC |
| | | CAGTATCAGCCCGTCATACTTGAAGCTAGACAGGCTTATCTTGGACAAGAAGAAGA |
| | | TCGCTTGGCCTCGCGCGCAGATCAGTTGGAAGAATTTGTCCACTACGTGAAAGGCG |
| | | AGATCACCAAGGTAGTCGGCAAATAATGTCTAACAATTCGTTCAAGCCGACGCCGC |
| | | TTCGCGGCGCGGCTTAACTCAAGCGTTAGATGCACTAAGCACATAATTGCTCACAG |
| | | CCAAACTATCAGGTCAAGTCTGCTTTTATTATTTTTAAGCGTGCATAATAAGCCCT |
| | | ACACAAATTGGGAGATATATCATGAGGCGCGCCACGAGAAAGAGTTATGACAAATT |
| | | AAAATTCTGACTCTTAGATTATTTCCAGAGAGGCTGATTTTCCCAATCTTTGGGAA |
| | | AGCCTAAGTTTTTAGATTCTATTTCTGGATACATCTCAAAAGTTCTTTTTAAATGC |
| | | TGTGCAAAATTATGCTCTGGTTTAATTCTGTCTAAGAGATACTGAATACAACATAA |
| | | GCCAGTGAAAATTTTACGGCTGTTTCTTTGATTAATATCCTCCAATACTTCTCTAG |
| | | AGAGCCATTTTCCTTTTAACCTATCAGGCAATTTAGGTGATTCTCCTAGCTGTATA |
| | | TTCCAGAGCCTTGAATGATGAGCGCAAATATTTCTAATATGCGACAAAGACCGTAA |
| | | CCAAGATATAAAAAACTTGTTAGGTAATTGGAAATGAGTATGTATTTTTTGTCGTG |
| | | TCTTAGATGGTAATAAATTTGTGTACATTCTAGATAACTGCCCAAAGGCGATTATC |
| | | TCCAAAGCCATATATGACGGCGGTAGTAGAGGATTTGTGTACTTGTTTCGATAATG |
| | | CCCGATAAATTCTTCTACTTTTTTAGATTGGCAATATTGAGTAATCGAATCGATTA |
| | | ATTCTTGATGCTTCCCAGTGTCATAAAATAAACTTTTATTCAGATACCAATGAGGA |
| | | TCATAATCATGGAGTAGTGATAAATCATTTGAGTTCTGACTGCTACTTCTATCGA |
| | | CTCCGTAGCATTAAAAATAAGCATTCTCAAGGATTTATCAAACTTGTATAGATTTG |
| | | GCCGGCCCGTCAAAAGGGCGACACCCCATAATTAGCCCGGGCGAAAGGCCCAGTCT |
| | | TTCGACTGAGCCTTTCGTTTTATTTGATGCCTGGCAGTTCCCTACTCTCGCATGGG |
| | | GAGTCCCCACACTACCATCGGCGCTACGGCGTTTCACTTCTGAGTTCGGCATGGGG |
| | | TCAGGTGGGACCACCGCGCTACTGCCGCCAGGCAAACAAGGGGTGTTATGAGCCAT |
| | | ATTCAGGTATAAATGGGCTCGCGATAATGTTCAGAATTGGTTAATTGGTTGTAACA |
| | | CTGACCCCTATTTGTTTATTTTTCTAAATACATTCAAATATGTATCCGCTCATGAG |
| | | ACAATAACCCTGATAAATGCTTCAATAATATTGAAAAAGGAAGAATATGAGTATTC |
| | | AACATTTCCGTGTCGCCCTTATTCCCTTTTTTGCGGCATTTTGCCTTCCTGTTTTT |
| | | GCTCACCCAGAAACGCTGGTGAAAGTAAAAGATGCTGAAGATCAGTTGGGTGCACG |

TABLE 1-continued

| SEQ ID NO | DESCRIPTION | SEQUENCE |
|---|---|---|
| | | AGTGGGTTACATCGAACTGGATCTCAACAGCGGTAAGATCCTTGAGAGTTTTCGCC<br>CCGAAGAACGTTTTCCAATGATGAGCACTTTTAAAGTTCTGCTATGTGGCGCGGTA<br>TTATCCCGTATTGACGCCGGGCAAGAGCAACTCGGTCGCCGCATACACTATTCTCA<br>GAATGACTTGGTTGAGTACTCACCAGTCACAGAAAAGCATCTTACGGATGGCATGA<br>CAGTAAGAGAATTATGCAGTGCTGCCATAACCATGAGTGATAACACTGCGGCCAAC<br>TTACTTCTGACAACGATCGGAGGACCGAAGGAGCTAACCGCTTTTTTGCACAACAT<br>GGGGGATCATGTAACTCGCCTTGATCGTTGGGAACCGGAGCTGAATGAAGCCATAC<br>CAAACGACGAGCGTGACACCACGATGCCTGTAGCGATGGCAACAACGTTGCGCAAA<br>CTATTAACTGGCGAACTACTTACTCTAGCTTCCCGGCAACAATTAATAGACTGGAT<br>GGAGGCGGATAAAGTTGCAGGACCACTTCTGCGCTCGGCCCTTCCGGCTGGCTGGT<br>TTATTGCTGATAAATCCGGAGCCGGTGAGCGTGGTTCTCGCGGTATCATCGCAGCG<br>CTGGGGCCAGATGGTAAGCCCTCCCGTATCGTAGTTATCTACACGACGGGGAGTCA<br>GGCAACTATGGATGAACGAAATAGACAGATCGCTGAGATAGGTGCCTCACTGATTA<br>AGCATTGGT |
| 9 | carB<br>Mycobacterium<br>smegmatis | MTSDVHDATDGVTETALDDEQSTRRIAELYATDPEFAAAAPLPAVVDAAHKPGLRL<br>AEILQTLFTGYGDRPALGYRARELATDEGGRTVTRLLPRFDTLTYAQVWSRVQAVA<br>AALRHNFAQPIYPGDAVATIGFASPDYLTLDLVCAYLGLVSVPLQHNAPVSRLAPI<br>LAEVEPRILTVSAEYLDLAVESVRDVNSVSQLVVFDHHPEVDDHRDALARAREQLA<br>GKGIAVTTLDAIADEGAGLPAEPIYTADHDQRLAMILYTSGSTGAPKGAMYTEAMV<br>ARLWTMSFITGDPTPVINVNFMPLNHLGGRIPISTAVQNGGTSYFVPESDMSTLFE<br>DLALVRPTELGLVPRVADMLYQHHLATVDRLVTQGADELTAEKQAGAELREQVLGG<br>RVITGFVSTAPLAAEMRAFLDITLGAHIVDGYGLTETGAVTRDGVIVRPPVIDYKL<br>IDVPELGYFSTDKPYPRGELLVRSQTLTPGYYKRPEVTASVFDRDGYYHTGDVMAE<br>TAPDHLVYVDRRNNVLKLAQGEFVAVANLEAVFSGAALVRQIFVYGNSERSFLLAV<br>VVPTPEALEQYDPAALKAALADSLQRTARDAELQSYEVPADFIVETEPFSAANGLL<br>SGVGKLLRPNLKDRYGQRLEQMYADIAATQANQLRELRRAAATQPVIDTLTQAAAT<br>ILGTGSEVASDAHFTDLGGDSLSALTLSNLLSDFFGFEVPVGTIVNPATNLAQLAQ<br>HIEAQRTAGDRRPSFTTVHGADATEIRASELTLDKFIDAETLRAAPGLPKVTTEPR<br>TVLLSGANGWLGRFLTLQWLERLAPVGGTLITIVRGRDDAAARARLTQAYDTDPEL<br>SRRFAELADRHLRVVAGDIGDPNLGLTPEIWHRLAAEVDLVVHPAALVNHVLPYRQ<br>LFGPNVVGTAEVIKLALTERIKPVTYLSTVSVAMGIPDFEEDGDIRTVSPVRPLDG<br>GYANGYGNSKWAGEVLLREAHDLCGLPVATFRSDMILAHPRYRGQVNVPDMFTRLL<br>LSLLITGVAPRSFYIGDGERPRAHYPGLTVDFVAEAVTTLGAQQREGYVSYDVMNP<br>HDDGISLDVFVDWLIRAGHPIDRVDDYDDWVRRFETALTALPEKRRAQTVLPLLHA<br>FRAPQAPLRGAPEPTEVFHAAVRTAKVGPGDIPHLDEALIDKYIRDLREFGLI |
| 10 | entD E.coli | MKTTHTSLPFAGHTLHFVEFDPANFCEQDLLWLPHYAQLQHAGRKRKTEHLAGRIA<br>AVYALREYGYKCVPAIGELRQPVWPAEVYGSISHCGTTALAVVSRQPIGIDIEEIF<br>SVQTARELTDNIITPAEHERLADCGLAFSLALTLAFSAKESAFKASEIQTDAGFLD<br>YQIISWNKQQVIIHRENEMFAVHWQIKEKIVITLCQHD |
| 11 | acrM<br>Acinetobacter<br>sp. M-1 | MNAKLKKLFQQKVDGKTIIVTGASSGIGLTVSKYLAQAGAHVLLLARTKEKLDEVK<br>AEIEAEGGKATVFPCDLNDMESIDAVSKEILAAVDHIDILVNNAGRSIRRAVHESV<br>DRFHDFERTMQLNYFGAVRLVLNVLPHMMQRKDGQIINISSIGVLANATRFSAYVA<br>SKAALDAFSRCLSAEVHSHKIAITSIYMPLVRTPMIAPTKIYKYVPTLSPEEAADL<br>IAYAIVKRPKKIATNLGRLASITYAIAPDINNILMSIGFNLFPSSTASVGEQEKLN<br>LIQRAYARLFPGEHW |
| 12 | fadD E.coli | MKKVWLNRYPADVPTEINPDRYQSLVDMFEQSVARYADQPAFVNMGEVMTFRKLEE<br>RSRAFAAYLQQGLGLKKGDRVALMMPNLLQYPVALFGILRAGMIVVNVNPLYTPRE<br>LEHQLNDSGASAIVIVSNFAHTLEKVVDKTAVQHVILTRMGDQLSTAKGTVVNFVV<br>KYIKRLVPKYHLPDAISFRSALHNGYRMQYVKPELVPEDLAFLQYTGGTTGVAKGA<br>MLTHRNMLANLEQVNATYGPLLHPGKELVVTALPLYHIFALTINCLLFIELGGQNL<br>LITNPRDIPGLVKELAKYPFTAITGVNTLFNALLNNKEFQQLDFSSLHLSAGGGMP<br>VQQVVAERWVKLTGQYLLEGYGLTECAPLVSVNPYDIDYHSGSIGLPVPSTEAKLV<br>DDDDNEVPPGQPGELCVKGPQVMLGYWQRPDATDEIIKNGWLHTGDIAVMDEEGFL<br>RIVDRKKDMILVSGFNVYPNEIEDVVMQHPGVQEVAAVGVPSGSSGEAVKIFVVKK<br>DPSLTEESLVTFCRRQLTGYKVPKLVEFRDELPKSNVGKILRRELRDEARGKVDNK<br>A |
| 13 | fatB(C12<br>fatty acid)<br>Umbellularia<br>californica | MATTSLASAFCSMKAVMLARDGRGMKPRSSDLQLRAGNAPTSLKMINGTKFSYTES<br>LKRLPDWSMLFAVITTIFSAAEKQWTNLEWKPKPKLPQLLDDHFGLHGLVFRRTFA<br>IRSYEVGPDRSTSILAVMNHMQEATLNHAKSVGILGDGFGTTLEMSKRDLMWVVRR<br>THVAVERYPTWGDTVEVECWIGASGNNGMRRDFLVRDCKTGEILTRCTSLSVLMNT<br>RTRRLSTIPDEVRGEIGPAFIDNVAVKDDEIKKLQKLNDSTADYIQGGLTPRWNDL<br>DVNQHVNNLKYVAWVFETVPDSIFESHHISSFTLEYRRECTRDSVLRSLTTVSGGS<br>SEAGLVCDHLLQLEGGSEVLRARTEWRPKLTDSFRGISVIPAEPRV |
| 14 | fatBmat(fatB<br>without<br>leader<br>sequence)<br>Umbellularia<br>californica | MEWKPKPKLPQLLDDHFGLHGLVFRRTFAIRSYEVGPDRSTSILAVMNHMQEATLN<br>HAKSVGILGDGFGTTLEMSKRDLMWVVRRTHVAVERYPTWGDTVEVECWIGASGNN<br>GMRRDFLVRDCKTGEILTRCTSLSVLMNTRTRRLSTIPDEVRGEIGPAFIDNVAVK<br>DDEIKKLQKLNDSTADYIQGGLTPRWNDLDVNQHVNNLKYVAWVFETVPDSIFESH<br>HISSFTLEYRRECTRDSVLRSLTTVSGGSSEAGLVCDHLLQLEGGSEVLRARTEWR<br>PKLTDSFRGISVIPAEPRV |

TABLE 1-continued

| SEQ ID NO | DESCRIPTION | SEQUENCE |
|---|---|---|
| 15 | fatB2(C8 C10 fatty acid) Cuphea hookeriana | MVAAAASSAFFPVPAPGASPKPGKFGNWPSSLSPSFKPKSIPNGGFQVKANDSAHP KANGSAVSLKSGSLNTQEDTSSSPPPRTFLHQLPDWSRLLTAITTVFVKSKRPDMH DRKSKRPDMLVDSFGLESTVQDGLVFRQSFSIRSYEIGTDRTASIETLMNHLQETS LNHCKSTGILLDGFGRTLEMCKRDLIWVVIKMQIKVNRYPAWGDTVEINTRFSRLG KIGMGRDWLISDCNTGEILVRATSAYAMMNQKTRRLSKLPYEVHQEIVPLFVDSPV IEDSDLKVHKFKVKTGDSIQKGLTPGWNDLDVNQHVSNVKYIGWILESMPTEVLET QELCSLALEYRRECGRDSVLESVTAMDPSKVGVRSQYQHLLRLEDGTAIVNGATEW RPKNAGANGAISTGKTSNGNSVS |
| 16 | fatB2mat(fatB 2 without leader sequence) Cuphea hookeriana | MDRKSKRPDMLVDSFGLESTVQDGLVFRQSFSIRSYEIGTDRTASIETLMNHLQET SLNHCKSTGILLDGFGRTLEMCKRDLIWVVIKMQIKVNRYPAWGDTVEINTRFSRL GKIGMGRDWLISDCNTGEILVRATSAYAMMNQKTRRLSKLPYEVHQEIVPLFVDSP VIEDSDLKVHKFKVKTGDSIQKGLTPGWNDLDVNQHVSNVKYIGWILESMPTEVLE TQELCSLALEYRRECGRDSVLESVTAMDPSKVGVRSQYQHLLRLEDGTAIVNGATE WRPKNAGANGAISTGKTSNGNSVS |
| 17 | kivd Lactococcus lactis | MYTVGDYLLDRLHELGIEEIFGVPGDYNLQFLDQIISRKDMKWVGNANELNASYMA DGYARTKKAAAFLTTFGVGELSAVNGLAGSYAENLPVVEIVGSPTSKVQNEGKFVH HTLADGDFKHFMKMHEPVTAARTLLTAENATVEIDRVLSALLKERKPVYINLPVDV AAAKAEKPSLPLKKENPTSNTSDQEILNKIQESLKNAKKPIVITGHEIISFGLENT VTQFISKTKLPITTLNFGKSSVDETLPSFLGIYNGKLSEPNLKEFVESADFILMLG VKLTDSSTGAFTHHLNENKMISLNIDEGKIFNESIQNFDFESLISSLLDLSGIEYK GKYIDKKQEDFVPSNALLSQDRLWQAVENLTQSNETIVAEQGTSFFGASSIFLKPK SHFIGQPLWGSIGYTFPAALGSQIADKESRHLLFIGDGSLQLTVQELGLAIREKIN PICFIINNDGYTVEREIHGPNQSYNDIPMWNYSKLPESFGATEERVVSKIVRTENE FVSVMKEAQADPNRMYWIELVLAKEDAPKVLKKMGKLFAEQNKS |

TABLE 2

| | General Enzyme Activity | Enzyme Activity | Enzyme | EC # | Gene Name | Organism | Accession Number |
|---|---|---|---|---|---|---|---|
| 1 | Alkane deformylative monooxygenase activity | An aldehyde + O2 + 2 NADPH + 2 H+ = an (n-1) alkane + formate + H2O + 2 NADP+ | alkane deformylative monooxygenase | 4.1.99.5 | adm | Cyanothece sp. ATCC 51142 | YP_001802195 |
| | | | | | adm | Nostoc punctiforme | YP_001865325 |
| | | | | | adm | Prochlorococcus marinus MIT 9312 | YP_397029 |
| | | | | | adm | Thermosynechococcus elongatus BP-1 | NP_682103 |
| 2 | Carboxylic acid reductase activity | An aldehyde + acceptor + H2O = a carboxylate + reduced acceptor | carboxylic acid reductase | 1.2.99.6 | carB | Mycobacterium smegmatis str. MC2 155 | YP_889972 |
| | | | | | car | Nocardia iowensis | AAR91681 |
| | | | | | fadD9 | Mycobacterium marinum M | YP_001850422 |
| 3 | Phosphopantetheinyl transferase activity | CoA-[4'-phosphopantetheine] + apo-[acyl-carrier protein] = adenosine 3',5'-bisphosphate + holo-[acyl-carrier protein] | phosphopantetheinyl transferase | 2.7.8.7 | entD | Escherichia coli | NP_415115 |
| | | | | | sfp | Bacillus subtilis subsp. subtilis str. SC-8 | ZP_12673024 |
| 4 | Thioesterase activity | A fatty acyl-[acyl-carrier protein] + H2O = [acyl-carrier protein] + a fatty acid | thioesterase | 3.1.2.14 | fatB2 | Cuphea hookeriana | AAC49269 |
| | | | | | tesA | Escherichia coli | NP_415027 |
| | | | | | FatB3 | Cocos nucifera | AEM72521 |
| | | | | | Ua-FatB1 | Ulmus americana | AAB71731 |
| 5 | Long-chain acyl-CoA reductase activity | An aldehyde + CoA + NADP+ = an acyl-CoA + NADPH + H+ | long-chain acyl-CoA reductase | 1.2.1.50 | acrM | Acinetobacter sp. M-1 | BAB85476 |
| | | | | | ucpA | Escherichia coli | NP_416921 |
| | | | | | ybbO | Escherichia coli | NP_415026 |
| | | | | | luxC | Photorhabdus luminescens subsp. laumondii TTO1 | NP_929340 |
| | | | | | acr1 | Acinetobacter sp. ADP-1 | YP_047869 |

TABLE 2-continued

| General Enzyme Activity | Enzyme Activity | Enzyme | EC # | Gene Name | Organism | Accession Number |
|---|---|---|---|---|---|---|
| 6 Long-chain fatty acid CoA-ligase activity | ATP + a long-chain fatty acid + CoA = AMP + diphosphate + an acyl-CoA | long-chain fatty acid CoA-ligase | 6.2.1.3 | fadD<br>fadD<br>TTC0079 | *Escherichia coli*<br>*Synechococcus elongatus*<br>*Thermus thermophilus* HB27 | NP_416319<br>YP_001733936<br>YP_004054 |

What is claimed is:

1. An engineered cyanobacterium, wherein the engineered cyanobacterium comprises recombinant genes encoding an alkane deformylative monooxygenase having EC number 4.1.99.5, a thioesterase having EC number 3.1.2.14, and a carboxylic acid reductase having EC number 1.2.99.6, wherein the alkane deformylative monooxygenase is encoded by adm, the thioesterase is encoded by fatB or fatB2, and the carboxylic acid reductase is encoded by carB, wherein the thioesterase converts $C_{(8-12)}$ acyl-ACP to $C_{(8-12)}$ fatty acid, wherein the carboxylic acid reductase converts $C_{(8-12)}$ fatty acid to $C_{(8-12)}$ aldehyde, wherein the alkane deformylative monooxygenase converts $C_{(8-12)}$ aldehyde to $C_{(7-11)}$ alkane, and wherein the engineered cyanobacterium produces at least one of heptane, nonane, and undecane in an amount greater than an otherwise identical cyanobacterium, cultured under identical conditions, but lacking recombinant genes encoding alkane deformylative monooxygenase, thioesterase, and carboxylic acid reductase.

2. The engineered cyanobacterium of claim 1, wherein the cyanobacterium further comprises one or more recombinant genes encoding a phosphopanthetheinyl transferase.

3. The engineered cyanobacterium of claim 1, wherein the cyanobacterium further comprises one or more recombinant genes encoding a phosphopanthetheinyl transferase having EC number 2.7.8.7.

4. The engineered cyanobacterium of claim 3, wherein the phosphopanthetheinyl transferase is encoded by entD.

5. The engineered cyanobacterium of claim 1, wherein the cyanobacterium is a thermotolerant cyanobacterium, or a *Synechococcus* species.

6. The engineered cyanobacterium of claim 1, wherein expression of an operon comprising one or more of the recombinant genes is controlled by a recombinant promoter, and wherein the promoter is constitutive or inducible.

7. The engineered cyanobacterium of claim 1, wherein the cyanobacterium produces alkanes 7 to 11 carbon atoms in length; or alkanes 7, 8, 9, 10, or 11 carbon atoms in length.

8. A cell culture comprising a culture medium and the cyanobacterium of claim 1.

9. A method for producing hydrocarbons, comprising:
culturing an engineered cyanobacterium of claim 1 in a culture medium, wherein the engineered cyanobacterium produces increased amounts of alkanes relative to an otherwise identical cyanobacterium, cultured under identical conditions, but lacking the recombinant genes.

10. A method for producing hydrocarbons, comprising:
(i) culturing an engineered cyanobacterium of claim 1 in a culture medium; and
(ii) exposing the engineered cyanobacterium to light and inorganic carbon, wherein said exposure results in the conversion of said inorganic carbon by the cyanobacterium into alkanes, wherein the alkanes are produced in an amount greater than that produced by an otherwise identical cyanobacterium, cultured under identical conditions, but lacking the recombinant genes.

11. The engineered cyanobacterium of claim 1, wherein the cyanobacterium produces alkanes 9 carbon atoms in length.

12. The engineered cyanobacterium of claim 1, wherein the cyanobacterium produces alkanes 11 carbon atoms in length.

13. The engineered cyanobacterium of claim 1, wherein the cyanobacterium produces alkanes 9 and 11 carbon atoms in length.

14. The method of claim 9, wherein the alkanes produced are 9 or 11 carbons in length.

15. The method of claim 10, wherein the alkanes produced are 9 or 11 carbons in length.

16. The engineered cyanobacterium of claim 1, wherein the predominant alkane produced by the cyanobacterium is nonane.

* * * * *

SEQUENCE LISTING

<160> NUMBER OF SEQ ID NOS: 18

<210> SEQ ID NO 1
<211> LENGTH: 888
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
atgaatgcaa aactgaagaa attgttccag cagaaagtag acggcaagac catcatcgtg     60
accggtgcaa gcagcggtat tggcttgacc gtgagcaaat acctggctca ggcgggtgca    120
cacgtgctgc tgctggcgcg tacgaaagag aaactggatg aggtcaaggc ggagattgaa    180
gcggaaggcg gtaaggctac tgttttcccg tgcgatttga atgacatgga atccattgac    240
gcagtcagca aagagatcct ggcagccgtt gatcatatcg acattctggt gaataacgcg    300
ggtcgcagca tccgtcgcgc ggtccacgaa agcgtggatc gcttccatga ctttgagcgt    360
accatgcaac tgaattactt cggtgccgtt cgtctggtcc tgaatgttct gccgcacatg    420
atgcagcgca aagatggcca aatcattaac attagcagca ttggcgtttt ggcgaacgcg    480
acgcgtttca gcgcgtatgt ggcgagcaag gctgcactgg atgccttctc ccgttgtctg    540
agcgccgagg tccattcgca caagattgcg attacctcta tctatatgcc gctggttcgt    600
accccgatga ttgcgccgac gaagatctac aagtatgtcc caacgttgtc cccggaagag    660
gcggctgacc tgattgctta tgcgatcgtt aaacgtccga aaaagatcgc caccaatctg    720
ggtcgcctgg caagcatcac ctacgcgatt gccccggaca tcaacaacat cctgatgagc    780
atcggcttta acctgtttcc gtctagcacg gcgagcgtgg gtgagcaaga aaagctgaac    840
ctgattcaac gtgcctacgc acgtctgttt cctggtgaac actggtaa                 888
```

<210> SEQ ID NO 2
<211> LENGTH: 6215
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta aatcggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
```

```
ctttaatagt ggactcttgt tccaaactgg aacaacactc aaccctatct cggtctattc      360
ttttgattta taagggattt tgccgatttc ggcctattgg ttaaaaaatg agctgattta      420
acaaaaattt aacgcgaatt ttaacaaaat attaacgttt acaatttcag gtggcacttt      480
tcggggaaat gtgcgcggaa cccctatttg tttattttc taaatacatt caaatatgta      540
tccgctcatg aattaattct tagaaaaact catcgagcat caaatgaaac tgcaatttat      600
tcatatcagg attatcaata ccatattttt gaaaaagccg tttctgtaat gaaggagaaa      660
actcaccgag gcagttccat aggatggcaa gatcctggta tcggtctgcg attccgactc      720
gtccaacatc aatacaacct attaatttcc cctcgtcaaa aataaggtta tcaagtgaga      780
aatcaccatg agtgacgact gaatccggtg agaatggcaa aagtttatgc atttctttcc      840
agacttgttc aacaggccag ccattacgct cgtcatcaaa atcactcgca tcaaccaaac      900
cgttattcat tcgtgattgc gcctgagcga gacgaaatac gcgatcgctg ttaaaaggac      960
aattacaaac aggaatcgaa tgcaaccggc gcaggaacac tgccagcgca tcaacaatat     1020
tttcacctga atcaggatat tcttctaata cctggaatgc tgttttcccg gggatcgcag     1080
tggtgagtaa ccatgcatca tcaggagtac ggataaaatg cttgatggtc ggaagaggca     1140
taaattccgt cagccagttt agtctgacca tctcatctgt aacatcattg gcaacgctac     1200
ctttgccatg tttcagaaac aactctggcg catcgggctt cccatacaat cgatagattg     1260
tcgcacctga ttgcccgaca ttatcgcgag cccatttata cccatataaa tcagcatcca     1320
tgttggaatt taatcgcggc ctagagcaag acgtttcccg ttgaatatgg ctcataacac     1380
cccttgtatt actgtttatg taagcagaca gttttattgt tcatgaccaa aatcccttaa     1440
cgtgagtttt cgttccactg agcgtcagac cccgtagaaa agatcaaagg atcttcttga     1500 gatcctttt ttctgcgcgt aatctgctgc ttgcaaacaa aaaaaccacc gctaccagcg     1560
gtggtttgtt tgccggatca agagctacca actcttttc cgaaggtaac tggcttcagc     1620
agagcgcaga taccaaatac tgtccttcta gtgtagccgt agttaggcca ccacttcaag     1680
aactctgtag caccgcctac atacctcgct ctgctaatcc tgttaccagt ggctgctgcc     1740
agtggcgata agtcgtgtct taccgggttg gactcaagac gatagttacc ggataaggcg     1800
cagcggtcgg gctgaacggg gggttcgtgc acacagccca gcttggagcg aacgacctac     1860
accgaactga gatacctaca gcgtgagcta tgagaaagcg ccacgcttcc gaagggagaa     1920
aaggcggaca ggtatccggt aagcggcagg gtcggaacag gagagcgcac gagggagctt     1980
ccagggggaa acgcctggta tctttatagt cctgtcgggt ttcgccacct ctgacttgag     2040
cgtcgatttt tgtgatgctc gtcagggggg cggagcctat ggaaaaacgc cagcaacgcg     2100
gcctttttac ggttcctggc cttttgctgg ccttttgctc acatgttctt tcctgcgtta     2160
tcccctgatt ctgtggataa ccgtattacc gcctttgagt gagctgatac cgctcgccgc     2220
agccgaacga ccgagcgcag cgagtcagtg agcgaggaag cggaagagcg cctgatgcgg     2280
tattttctcc ttacgcatct gtgcggtatt tcacaccgca tatatggtgc actctcagta     2340
caatctgctc tgatgccgca tagttaagcc agtatacact ccgctatcgc tacgtgactg     2400
ggtcatggct gcgccccgac acccgccaac cccgctgac gcgccctgac gggcttgtct     2460
gctcccggca tccgcttaca gacaagctgt gaccgtctcc gggagctgca tgtgtcagag     2520
gttttcaccg tcatcaccga aacgcgcgag gcagctgcgg taaagctcat cagcgtggtc     2580
gtgaagcgat tcacagatgt ctgcctgttc atccgcgtcc agctcgttga gtttctccag     2640
aagcgttaat gtctggcttc tgataaagcg ggccatgtta agggcggttt tttcctgttt     2700
```

```
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag gtggtttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg tgtccggga    4680 tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
```

| | |
|---|---|
| tttgttttaa ctttaagaag gagatatacc atgggcagca gccatcatca tcatcatcac | 5100 |
| agcagcggcc tggtgccgcg cggcagccat atgaatgcaa aactgaagaa attgttccag | 5160 |
| cagaaagtag acggcaagac catcatcgtg accggtgcaa gcagcggtat tggcttgacc | 5220 |
| gtgagcaaat acctggctca ggcgggtgca cacgtgctgc tgctggcgcg tacgaaagag | 5280 |
| aaactggatg aggtcaaggc ggagattgaa gcggaaggcg gtaaggctac tgttttcccg | 5340 |
| tgcgatttga atgacatgga atccattgac gcagtcagca aagagatcct ggcagccgtt | 5400 |
| gatcatatcg acattctggt gaataacgcg ggtcgcagca tccgtcgcgc ggtccacgaa | 5460 |
| agcgtggatc gcttccatga ctttgagcgt accatgcaac tgaattactt cggtgccgtt | 5520 |
| cgtctggtcc tgaatgttct gccgcacatg atgcagcgca aagatggcca aatcattaac | 5580 |
| attagcagca ttggcgtttt ggcgaacgcg acgcgtttca gcgcgtatgt ggcgagcaag | 5640 |
| gctgcactgg atgccttctc ccgttgtctg agcgccgagg tccattcgca caagattgcg | 5700 |
| attacctcta tctatatgcc gctggttcgt accccgatga ttgcgccgac gaagatctac | 5760 |
| aagtatgtcc caacgttgtc cccggaagag gcggctgacc tgattgctta tgcgatcgtt | 5820 |
| aaacgtccga aaagatcgc caccaatctg ggtcgcctgg caagcatcac ctacgcgatt | 5880 |
| gccccggaca tcaacaacat cctgatgagc atcggcttta acctgtttcc gtctagcacg | 5940 |
| gcgagcgtgg gtgagcaaga aaagctgaac ctgattcaac gtgcctacgc acgtctgttt | 6000 |
| cctggtgaac actggtaaga attcgagctc cgtcgacaag cttgcggccg cactcgagca | 6060 |
| ccaccaccac caccactgag atccggctgc taacaaagcc cgaaaggaag ctgagttggc | 6120 |
| tgctgccacc gctgagcaat aactagcata accccttggg gcctctaaac gggtcttgag | 6180 |
| gggttttttg ctgaaaggag gaactatatc cggat | 6215 |

<210> SEQ ID NO 3
<211> LENGTH: 3549
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

| | |
|---|---|
| gagctcgagg aggttttac aatgaccagc gatgttcacg acgccacaga cggcgtcacc | 60 |
| gaaaccgcac tcgacgacga gcagtcgacc cgccgcatcg ccgagctgta cgccaccgat | 120 |
| cccgagttcg ccgccgccgc accgttgccc gccgtggtcg acgcggcgca caaacccggg | 180 |
| ctgcggctga cagagatcct gcagaccctg ttcaccggct acggtgaccg cccggcgctg | 240 |
| ggataccgcg cccgtgaact ggccaccgac gagggcgggc gcaccgtgac gcgtctgctg | 300 |
| ccgcggttca cacccctcac ctacgcccag gtgtggtcgc gcgtgcaagc ggtcgccgcg | 360 |
| gccctgcgcc acaacttcgc gcagccgatc taccccggcg acgccgtcgc gacgatcggt | 420 |
| ttcgcgagtc ccgattacct gacgctggat ctcgtatgcg cctacctggg cctcgtgagt | 480 |
| gttccgctgc agcacaacgc accggtcagc cggctcgccc cgatcctggc cgaggtcgaa | 540 |
| ccgcggatcc tcaccgtgag cgccgaatac ctcgacctcg cagtcgaatc cgtgcgggac | 600 |
| gtcaactcgg tgtcgcagct cgtggtgttc gaccatcacc ccgaggtcga cgaccaccgc | 660 |
| gacgcactgg cccgcgcgcg tgaacaactc gccggcaagg gcatcgccgt caccaccctg | 720 |
| gacgcgatcg ccgacgaggg cgccgggctg cggccgaaac cgatctacac cgccgaccat | 780 |
| gatcagcgcc tcgcgatgat cctgtacacc tcgggttcca ccggcgcacc caagggtgcg | 840 |

```
atgtacaccg aggcgatggt ggcgcggctg tggaccatgt cgttcatcac gggtgacccc    900
acgccggtca tcaacgtcaa cttcatgccg ctcaaccacc tgggcgggcg catccccatt    960
tccaccgccg tgcagaacgg tggaaccagt tacttcgtac cggaatccga catgtccacg   1020
ctgttcgagg atctcgcgct ggtgcgcccc accgaactcg gcctggttcc gcgcgtcgcc   1080
gacatgctct accagcacca cctcgccacc gtcgaccgcc tggtcacgca gggcgccgac   1140
gaactgaccg ccgagaagca ggccggtgcc gaactgcgtg agcaggtgct cggcggacgc   1200
gtgatcaccg gattcgtcag caccgcaccg ctggccgcgg agatgagggc gttcctcgac   1260
atcaccctgg gcgcacacat cgtcgacggc tacgggctca ccgagaccgg cgccgtgaca   1320
cgcgacggtg tgatcgtgcg gccaccggtg atcgactaca agctgatcga cgttcccgaa   1380
ctcggctact tcagcaccga caagccctac ccgcgtggcg aactgctggt caggtcgcaa   1440
acgctgactc ccgggtacta caagcgcccc gaggtcaccg cgagcgtctt cgaccgggac   1500
ggctactacc acaccggcga cgtcatggcg gagaccgcac ccgaccacct ggtgtacgtg   1560
gaccgtcgca acaacgtcct caaactcgcg cagggcgagt tcgtggcggt cgccaacctg   1620
gaggcggtgt tctccggcgc ggcgctggtg cgccagatct tcgtgtacgg caacagcgag   1680
cgcagttttc ttctggccgt ggtggtcccg acgccggagg cgctcgagca gtacgatccg   1740
gccgcgctca aggccgcgct ggccgactcg ctgcagcgca ccgcacgcga cgccgaactg   1800
caatcctaca aggtgccggc cgatttcatc gtcgagaccg agccgttcag cgccgccaac   1860
gggctgctgt cgggtgtcgg aaaactgctg cggcccaacc tcaaagaccg ctacgggcag   1920
cgcctggagc agatgtacgc cgatatcgcg gccacgcagg ccaaccagtt gcgcgaactg   1980
cggcgcgcgg ccgccacaca accggtgatc gacaccctca cccaggccgc tgccacgatc   2040
ctcggcaccg ggagcgaggt ggcatccgac gcccacttca ccgacctggg cggggattcc   2100
ctgtcggcgc tgacactttc gaacctgctg agcgatttct tcggtttcga agttcccgtc   2160
ggcaccatcg tgaacccggc caccaacctc gcccaactcg cccagcacat cgaggcgcag   2220
cgcaccgcgg gtgaccgcag gccgagtttc accaccgtgc acggcgcgga cgccaccgag   2280
atccgggcga gtgagctgac cctggacaag ttcatcgacg ccgaaacgct ccgggccgca   2340
ccgggtctgc ccaaggtcac caccgagcca cggacggtgt tgctctcggg cgccaacggc   2400
tggctgggcc ggttcctcac gttgcagtgg ctggaacgcc tggcacctgt cggcggcacc   2460
ctcatcacga tcgtgcgggg ccgcgacgac gccgcggccc gcgcacggct gacccaggcc   2520
tacgacaccg atcccgagtt gtcccgccgc ttcgccgagc tggccgaccg ccacctgcgg   2580
gtggtcgccg gtgacatcgg cgacccgaat ctgggcctca cacccgagat ctggcaccgg   2640
ctcgccgccg aggtcgacct ggtggtgcat ccggcagcgc tggtcaacca cgtgctcccc   2700
taccggcagc tgttcggccc caacgtcgtg ggcacggccg aggtgatcaa gctggccctc   2760
accgaacgga tcaagcccgt cacgtacctg tccaccgtgt cggtggccat ggggatcccc   2820
gacttcgagg aggacggcga catccggacc gtgagcccgg tgcgcccgct cgacggcgga   2880
tacgccaacg gctacggcaa cagcaagtgg gccggcgagg tgctgctgcg ggaggcccac   2940
gatctgtgcg ggctgcccgt ggcgacgttc gctcggacca tgatcctggc gcatccgcgc   3000
taccgcggtc aggtcaacgt gccagacatg ttcacgcgac tcctgttgag cctcttgatc   3060
accggcgtcg cgccgcggtc gttctacatc ggagacggtg agcgcccgcg ggcgcactac   3120
cccgccctga cggtcgattt cgtggccgag gcggtcacga cgctcggcgc gcagcagcgc   3180
gagggatacg tgtcctacga cgtgatgaac ccgcacgacg acgggatctc cctggatgtg   3240
```

```
ttcgtggact ggctgatccg ggcgggccat ccgatcgacc gggtcgacga ctacgacgac      3300
tgggtgcgtc ggttcgagac cgcgttgacc gcgcttcccg agaagcgccg cgcacagacc      3360
gtactgccgc tgctgcacgc gttccgcgct ccgcaggcac cgttgcgcgg cgcacccgaa      3420
cccacggagg tgttccacgc cgcggtgcgc accgcgaagg tgggcccggg agacatcccg      3480
cacctcgacg aggcgctgat cgacaagtac atacgcgatc tgcgtgagtt cggtctgatc      3540
tgaggtacc                                                              3549
```

<210> SEQ ID NO 4
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
catatgcaag aactggccct gagaagcgag ctggacttca atagcgaaac ctataaagat       60
gcgtatagcc gtattaacgc cattgtgatc gaaggcgagc aagaagcata ccaaaactac      120
ctggacatgg cgcaactgct gccggaggac gaggctgagc tgattcgttt gagcaagatg      180
gagaaccgtc acaaaaaggg tttcaagcg tgcggcaaga acctcaatgt gactccggat      240
atggattatg cacagcagtt cttgtgcgag ctgcacggca ttttcagaa ggctaaagcc      300 gagggtaaga ttgttacctg cctgctcatc caaagcctga tcatcgaggc gtttgcgatt      360
gcagcctaca acatttacat tccagtggct gatccgtttg cacgtaaaat caccgagggt      420
gtcgtcaagg atgagtatac ccacctgaat ttcggcgaag tttggttgaa ggaacatttt      480
gaagcaagca aggcggagtt ggaggacgcc aacaaagaga acttaccgct ggtctggcag      540
atgttgaacc aggtcgaaaa ggatgccgaa gtgctgggta tggagaaaga ggctctggtg      600
gaggacttta tgattagcta tggtgaggca ctgagcaaca tcggcttttc tacgagagaa      660
atcatgaaga tgagcgcgta cggtctgcgt gcagcataag agctc                      705
```

<210> SEQ ID NO 5
<211> LENGTH: 4774
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
gagctcgagg aggtttttac aatgaccagc gatgttcacg acgccacaga cggcgtcacc       60
gaaaccgcac tcgacgacga gcagtcgacc cgccgcatcg ccgagctgta cgccaccgat      120
cccgagttcg ccgccgccgc accgttgccc gccgtggtcg acgcggcgca caacccggg      180 ctgcggctgg cagagatcct gcagaccctg ttcaccggct acggtgaccg cccggcgctg      240
ggataccgcg cccgtgaact ggccaccgac gagggcgggc gcaccgtgac gcgtctgctg      300
ccgcggttcg acaccctcac ctacgcccag gtgtggtcgc gcgtgcaagc ggtcgccgcg      360
gccctgcgcc acaacttcgc gcagccgatc taccccggcg acgccgtcgc gacgatcggt      420
ttcgcgagtc ccgattacct gacgctggat ctcgtatgcg cctacctggg cctcgtgagt      480
gttccgctgc agcacaacgc accggtcagc cggctcgccc cgatcctggc cgaggtcgaa      540
ccgcggatcc tcaccgtgag cgccgaatac ctcgacctcg cagtcgaatc cgtgcgggac      600
```

```
gtcaactcgg tgtcgcagct cgtggtgttc gaccatcacc ccgaggtcga cgaccaccgc    660
gacgcactgg cccgcgcgcg tgaacaactc gccggcaagg gcatcgccgt caccaccctg    720
gacgcgatcg ccgacgaggg cgccgggctg ccggccgaac cgatctacac cgccgaccat    780
gatcagcgcc tcgcgatgat cctgtacacc tcgggttcca ccggcgcacc caagggtgcg    840
atgtacaccg aggcgatggt ggcgcggctg tggaccatgt cgttcatcac gggtgacccc    900
acgccggtca tcaacgtcaa cttcatgccg ctcaaccacc tgggcgggcg catccccatt    960
tccaccgccg tgcagaacgg tggaaccagt tacttcgtac cggaatccga catgtccacg   1020
ctgttcgagg atctcgcgct ggtgcgcccc accgaactcg gcctggttcc gcgcgtcgcc   1080
gacatgctct accagcacca cctcgccacc gtcgaccgcc tggtcacgca gggcgccgac   1140
gaactgaccg ccgagaagca ggccggtgcc gaactgcgtg agcaggtgct cggcggacgc   1200
gtgatcaccg gattcgtcag caccgcaccg ctggccgcgg agatgagggc gttcctcgac   1260
atcaccctgg gcgcacacat cgtcgacggc tacgggctca ccgagaccgg cgccgtgaca   1320
cgcgacggtg tgatcgtgcg gccaccggtg atcgactaca agctgatcga cgttcccgaa   1380
ctcggctact tcagcaccga caagccctac ccgcgtggcg aactgctggt caggtcgcaa   1440
acgctgactc ccgggtacta caagcgcccc gaggtcaccg cgagcgtctt cgaccgggac   1500
ggctactacc acaccggcga cgtcatggcc gagaccgcac ccgaccacct ggtgtacgtg   1560
gaccgtcgca caacgtcct caaactcgcg cagggcgagt cgtggcggt cgccaacctg   1620 gaggcggtgt tctccggcgc ggcgctggtg cgccagatct tcgtgtacgg caacagcgag   1680
cgcagttttc ttctggccgt ggtggtcccg acgccggagg cgctcgagca gtacgatccg   1740
gccgcgctca aggccgcgct ggccgactcg ctgcagcgca ccgcacgcga cgccgaactg   1800
caatcctacg aggtgccggc cgatttcatc gtcgagaccg agccgttcag cgccgccaac   1860
gggctgctgt cgggtgtcgg aaaactgctg cggcccaacc tcaaagaccg ctacgggcag   1920
cgcctggagc agatgtacgc cgatatcgcg gccacgcagg ccaaccagtt gcgcgaactg   1980
cggcgcgcgg ccgccacaca accggtgatc gacaccctca cccaggccgc tgccacgatc   2040
ctcggcaccg ggagcgaggt ggcatccgac gcccacttca ccgacctggg cggggattcc   2100
ctgtcggcgc tgacactttc gaacctgctg agcgatttct tcggtttcga agttcccgtc   2160
ggcaccatcg tgaacccggc caccaacctc gcccaactcg cccagcacat cgaggcgcag   2220
cgcaccgcgg gtgaccgcag gccgagtttc accaccgtgc acggcgcgga cgccaccgag   2280
atccgggcga gtgagctgac cctggacaag ttcatcgacg ccgaaacgct ccgggccgca   2340
ccgggtctgc ccaaggtcac caccgagcca cggacggtgt tgctctcggg cgccaacggc   2400
tggctgggcc ggttcctcac gttgcagtgg ctggaacgcc tggcacctgt cggcggcacc   2460
ctcatcacga tcgtgcgggg ccgcgacgac gccgcggccc gcgcacggct gacccaggcc   2520
tacgacaccg atcccgagtt gtcccgccgc ttcgccgagc tggccgaccg ccacctgcgg   2580
gtggtcgccg gtgacatcgg cgacccgaat ctgggcctca cacccgagat ctggcaccgg   2640
ctcgccgccg aggtcgacct ggtggtgcat ccggcagcgc tggtcaacca cgtgctcccc   2700
taccggcagc tgttcggccc caacgtcgtg ggcacggccg aggtgatcaa gctggccctc   2760
accgaacgga tcaagcccgt cacgtacctg tccaccgtgt cggtggccat ggggatcccc   2820
gacttcgagg aggacggcga catccggacc gtgagcccgg tgcgcccgct cgacggcgga   2880
tacgccaacg gctacggcaa cagcaagtgg gccggcgagg tgctgctgcg ggaggccacc   2940
gatctgtgcg ggctgcccgt ggcgacgttc cgctcggaca tgatcctggc gcatccgcgc   3000
```

```
taccgcggtc aggtcaacgt gccagacatg ttcacgcgac tcctgttgag cctcttgatc   3060
accggcgtcg cgccgcggtc gttctacatc ggagacggtg agcgcccgcg ggcgcactac   3120
cccggcctga cggtcgattt cgtggccgag gcggtcacga cgctcggcgc gcagcagcgc   3180
gagggatacg tgtcctacga cgtgatgaac ccgcacgacg acgggatctc cctggatgtg   3240
ttcgtggact ggctgatccg ggcgggccat ccgatcgacc gggtcgacga ctacgacgac   3300
tgggtgcgtc ggttcgagac cgcgttgacc gcgcttcccg agaagcgccg cgcacagacc   3360
gtactgccgc tgctgcacgc gttccgcgct ccgcaggcac cgttgcgcgg cgcacccgaa   3420
cccacggagg tgttccacgc cgcggtgcgc accgcgaagg tgggcccggg agacatcccg   3480
cacctcgacg aggcgctgat cgacaagtac atacgcgatc tgcgtgagtt cggtctgatc   3540
tgaggtacca ggaggttttt acaatggctg atactttgtt gattttgggt gattctctct   3600
ctgcaggcta ccgtatgtcc gcgagcgcgg catggccggc tctgctgaac gataagtggc   3660
agagcaagac cagcgtggtc aatgcgagca tcagcggcga taccagccag cagggtctgg   3720
cacgtctgcc agcgctgctg aagcaacacc agccgcgttg ggtgctggtt gaactgggcg   3780
gcaatgacgg tctgcgtggt tttcagccgc agcagaccga acaaacgttg cgtcagattc   3840
tgcaggacgt caaggcggct aacgcggaac cgctgctgat gcaaattcgc ctgccggcga   3900
attatggtcg tcgttacaac gaggctttca gcgccattta tcctaaactg gctaaagagt   3960
tgacgtgcc gctgctgccg ttcttcatgg aagaggtcta cctgaaaccg caatggatgc   4020
aagacgacg tattcatccg aatcgtgatg cacaaccttt catcgcggat tggatggcga   4080
agcaattgca accgctggtg aaccatgact cgtaaaagct tgttgctgca tgcaggaggt   4140
ttttacaatg aaaacgaccc acaccagctt accatttgcc ggccacacgt tacatttcgt   4200
cgaatttgat ccggcgaact tttgtgaaca agacctgttg tggctgccgc attatgccca   4260
gctgcagcac gcaggccgta agcgtaaaac tgaacatctg gccggtcgca ttgcggcagt   4320
gtatgccctg cgcgagtacg gctacaaatg cgtgccggcc attggtgaac tgcgtcaacc   4380
ggtttggccg gcagaagttt acggttccat ctcccactgc ggtactaccg cgttggcggt   4440
tgtgtctcgc cagccgatcg gtattgatat tgaagagata ttctctgtcc agacggcacg   4500
cgagctgacg gacaacatca ttaccccggc agagcacgag cgtctggcgg actgtggtct   4560
ggcgttcagc ctggcgctga ccctggcatt cagcgcaaaa gagagcgcgt tcaaggcttc   4620
cgagatccaa accgatgcgg gcttcctgga ttatcaaatc atcagctgga acaagcaaca   4680
ggttatcatt caccgtgaga atgagatgtt tgccgtccat ggcagatta aagagaaaat   4740
cgttatcacc ctgtgccagc acgactgaga attc                               4774
```

<210> SEQ ID NO 6
<211> LENGTH: 11239
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
aaaagcagag cattacgctg acttgacggg acggcgcaag ctcatgacca aaatcccttta   60
acgtgagtta cgcgcgcgtc gttccactga gcgtcagacc ccgtagaaaa gatcaaagga   120
tcttcttgag atcctttttt tctgcgcgta atctgctgct tgcaaacaaa aaaaccaccg   180
ctaccagcgg tggtttgttt gccggatcaa gagctaccaa ctctttttcc gaaggtaact   240
```

```
ggcttcagca gagcgcagat accaaatact gttcttctag tgtagccgta gttagcccac    300
cacttcaaga actctgtagc accgcctaca tacctcgctc tgctaatcct gttaccagtg    360
gctgctgcca gtggcgataa gtcgtgtctt accgggttgg actcaagacg atagttaccg    420
gataaggcgc agcggtcggg ctgaacgggg gttcgtgca cacagcccag cttggagcga    480
acgacctaca ccgaactgag atacctacag cgtgagctat gagaaagcgc cacgcttccc    540
gaagggagaa aggcggacag gtatccggta agcggcaggg tcggaacagg agagcgcacg    600
agggagcttc caggggaaaa cgcctggtat ctttatagtc ctgtcgggtt tcgccacctc    660
tgacttgagc gtcgattttt gtgatgctcg tcagggggc ggagcctatg gaaaaacgcc    720
agcaacgcgg ccttttacg gttcctggcc ttttgctggc cttttgctca catgttcttt    780
cctgcgttat ccctgattc tgtggataac cgtattaccg cctttgagtg agctgatacc    840
gctcgccgca gccgaacgac cgagcgcagc gagtcagtga gcgaggaagc ggaaggcgag    900
agtagggaac tgccaggcat caaactaagc agaaggcccc tgacggatgg cctttttgcg    960
tttctacaaa ctctttctgt gttgtaaaac gacggccagt cttaagctcg gccccctgg    1020 gcggttctga taacgagtaa tcgttaatcc gcaaataacg taaaaacccg cttcggcggg    1080 ttttttatg gggggagttt agggaaagag catttgtcag aatatttaag ggcgcctgtc    1140
actttgcttg atatatgaga attatttaac cttataaatg agaaaaaagc aacgcacttt    1200
aaataagata cgttgctttt tcgattgatg aacacctata attaaactat tcatctatta    1260
tttatgattt tttgtatata caatatttct agtttgttaa agagaattaa gaaaataaat    1320
ctcgaaaata ataagggaa aatcagtttt tgatatcaaa attatacatg tcaacgataa    1380
tacaaaatat aatacaaact ataagatgtt atcagtattt attatgcatt tagaataaat    1440
tttgtgtcgc ccttcgctga acctgcaggc gagcatttca acgatgatga atgggacggc    1500
gaacccactg aacccgtcgc cattgaccca gaaccgcgca aagaacggga aaaaattgat    1560
ctcgatctgg aggatgaacc agaggaaaac cgcaaaccgc aaaaaatcaa agtgaagtta    1620
gccgatggga aagagcggga actcgcccat actcaaacca caacttttg ggatgctgat    1680 ggtaaaccca tttccgccca agaatttatc gaaaagctat ttggcgacct gcccgacctc    1740
ttcaaggatg aagccgaact acgcaccatc tgggggaaac ccgatacccg taaatcgttc    1800
ctgaccggac tcgcggaaaa aggctacggt gacacccaac tgaaggcgat cgcacgcatt    1860
gccgaagcgg aaaaaagtga tgtctatgat gtcctgactt gggttgccta acaccaaa    1920 cccattagca gagaagagcg agtaattaag catcgagatc tgattttctc gaagtacacc    1980
ggaaagcagc aagaattttt agattttgtc ctagaccaat acattcgaga aggagtggag    2040
gaacttgatc gggggaaact gcctaccctc atcgaaatca ataccaaac cgttaatgaa    2100 ggtttagtga tcttgggtca ggatatcggt caagtattcg cagattttca ggcggattta    2160
tataccgaag atgtggcata aaaaaggacg gcgatcgccg ggggcgttgc ctgccttgag    2220
cggccgcttg tagcaattgc tactaaaaac tgcgatcgct gctgaaatga ctggaattt    2280 tgtccctctc agctcaaaaa gtatcaatga ttacttaatg tttgttctgc gcaaacttct    2340
tgcagaacat gcatgattta caaaaagttg tagtttctgt taccaattgc gaatcgagaa    2400
ctgcctaatc tgccgagtat gcgatccttt agcaggagga aaaccatatg caagaactgg    2460
ccctgagaag cgagctggac ttcaatagcg aaacctataa agatgcgtat agccgtatta    2520
acgccattgt gatcgaaggc gagcaagaag cataccaaaa ctacctggac atggcgcaac    2580
```

-continued

```
tgctgccgga ggacgaggct gagctgattc gtttgagcaa gatggagaac cgtcacaaaa    2640
agggttttca agcgtgcggc aagaacctca atgtgactcc ggatatggat tatgcacagc    2700
agttctttgc ggagctgcac ggcaattttc agaaggctaa agccgagggt aagattgtta    2760
cctgcctgct catccaaagc ctgatcatcg aggcgtttgc gattgcagcc tacaacattt    2820
acattccagt ggctgatccg tttgcacgta aaatcaccga gggtgtcgtc aaggatgagt    2880
atacccacct gaatttcggc gaagtttggt tgaaggaaca ttttgaagca agcaaggcgg    2940
agttggagga cgccaacaaa gagaacttac cgctggtctg gcagatgttg aaccaggtcg    3000
aaaaggatgc cgaagtgctg ggtatggaga agaggctct ggtggaggac tttatgatta    3060
gctatggtga ggcactgagc aacatcggct tttctacgag agaaatcatg aagatgagcg    3120
cgtacggtct gcgtgcagca taagagctcg aggaggtttt tacaatgacc agcgatgttc    3180
acgacgccac agacggcgtc accgaaaccg cactcgacga cgagcagtcg acccgccgca    3240
tcgccgagct gtacgccacc gatcccgagt cgccgccgc cgcaccgttg cccgccgtgg    3300
tcgacgcggc gcacaaaccc gggctgcggc tggcagagat cctgcagacc ctgttcaccg    3360
gctacggtga ccgcccggcg ctgggatacc gcgccgtga actggccacc gacgagggcg    3420
ggcgcaccgt gacgcgtctg ctgccgcggt tcgacaccct cacctacgcc caggtgtggt    3480
cgcgcgtgca agcggtcgcc gcggccctgc gccacaactt cgcgcagccg atctaccccg    3540
gcgacgccgt cgcgacgatc ggtttcgcga gtcccgatta cctgacgctg gatctcgtat    3600
gcgcctacct gggcctcgtg agtgttccgc tgcagcacaa cgcaccggtc agccggctcg    3660
ccccgatcct ggccgaggtc gaaccgcgga tcctcaccgt gagcgccgaa tacctcgacc    3720
tcgcagtcga atccgtgcgg gacgtcaact cggtgtcgca gctcgtggtg ttcgaccatc    3780
accccgaggt cgacgaccac cgcgacgcac tggcccgcgc cgtgaacaa ctcgccggca    3840 agggcatcgc cgtcaccacc ctggacgcga tcgccgacga gggcgccggg ctgccggccg    3900
aaccgatcta caccgccgac catgatcagc gcctcgcgat gatcctgtac acctcgggtt    3960
ccaccggcgc acccaagggt gcgatgtaca ccgaggcgat ggtggcgcgg ctgtggacca    4020
tgtcgttcat cacgggtgac cccacgccgg tcatcaacgt caacttcatg ccgctcaacc    4080
acctgggcgg gcgcatcccc atttccaccg ccgtgcagaa cggtggaacc agttacttcg    4140
taccggaatc cgacatgtcc acgctgttcg aggatctcgc gctggtgcgc ccgaccgaac    4200
tcggcctggt tccgcgcgtc gccgacatgc tctaccagca ccacctcgcc accgtcgacc    4260
gcctggtcac gcagggcgcc gacgaactga ccgccgagaa gcaggccggt gccgaactgc    4320
gtgagcaggt gctcggcgga cgcgtgatca ccggattcgt cagcaccgca ccgctggccg    4380
cggagatgag ggcgttcctc gacatcaccc tgggcgcaca catcgtcgac ggctacgggc    4440
tcaccgagac cggcgccgtg acacgcgacg gtgtgatcgt gcggccaccg gtgatcgact    4500
acaagctgat cgacgttccc gaactcggct acttcagcac cgacaagccc tacccgcgtg    4560
gcgaactgct ggtcaggtcg caaacgctga ctcccgggta ctacaagcgc cccgaggtca    4620
ccgcgagcgt cttcgaccgg gacggctact accacaccgg cgacgtcatg gccgagaccg    4680
cacccgacca cctggtgtac gtggaccgtc gcaacaacgt cctcaaactc gcgcagggcg    4740
agttcgtggc ggtcgccaac ctggaggcgg tgttctccgg cgcggcgctg gtgcgccaga    4800
tcttcgtgta cggcaacagc gagcgcagtt tccttctggc cgtggtggtc ccgacgccgg    4860
aggcgctcga gcagtacgat ccggccgcgc tcaaggccgc gctggccgac tcgctgcagc    4920
gcaccgcacg cgacgccgaa ctgcaatcct acgaggtgcc ggccgatttc atcgtcgaga    4980
```

```
ccgagccgtt cagcgccgcc aacgggctgc tgtcgggtgt cggaaaactg ctgcggccca    5040
acctcaaaga ccgctacggg cagcgcctgg agcagatgta cgccgatatc gcggccacgc    5100
aggccaacca gttgcgcgaa ctgcggcgcg cggccgccac acaaccggtg atcgacaccc    5160
tcacccaggc cgctgccacg atcctcggca ccgggagcga ggtggcatcc gacgcccact    5220
tcaccgacct gggcggggat tccctgtcgg cgctgacact ttcgaacctg ctgagcgatt    5280
tcttcggttt cgaagttccc gtcggcacca tcgtgaaccc ggccaccaac ctcgcccaac    5340
tcgcccagca catcgaggcg cagcgcaccg cgggtgaccg caggccgagt ttcaccaccg    5400
tgcacggcgc ggacgccacc gagatccggg cgagtgagct gaccctggac aagttcatcg    5460
acgccgaaac gctccgggcc gcaccgggtc tgcccaaggt caccaccgag ccacggacgg    5520
tgttgctctc gggcgccaac ggctggctgg ccggttcct cacgttgcag tggctggaac    5580
gcctggcacc tgtcggcggc accctcatca cgatcgtgcg gggccgcgac gacgccgcgg    5640
cccgcgcacg gctgacccag gcctacgaca ccgatcccga gttgtcccgc cgcttcgccg    5700
agctggccga ccgccacctg cgggtggtcg ccggtgacat cggcgacccg aatctgggcc    5760
tcacacccga gatctggcac cggctcgccg ccgaggtcga cctggtggtg catccggcag    5820
cgctggtcaa ccacgtgctc ccctaccggc agctgttcgg ccccaacgtc gtgggcacgg    5880
ccgaggtgat caagctggcc ctcaccgaac ggatcaagcc cgtcacgtac ctgtccaccg    5940
tgtcggtggc catggggatc cccgacttcg aggaggacgg cgacatccgg accgtgagcc    6000
cggtgcgccc gctcgacggc ggatacgcca acggctacgg caacagcaag tgggccggcg    6060
aggtgctgct gcgggaggcc cacgatctgt gcgggctgcc cgtggcgacg ttccgctcgg    6120
acatgatcct ggcgcatccg cgctaccgcg gtcaggtcaa cgtgccagac atgttcacgc    6180
gactcctgtt gagcctcttg atcaccggcg tcgcgccgcg gtcgttctac atcggagacg    6240
gtgagcgccc gcgggcgcac taccccgccc tgacggtcga tttcgtggcc gaggcggtca    6300
cgacgctcgg cgcgcagcag cgcgagggat acgtgtccta cgacgtgatg aacccgcacg    6360
acgacgggat ctccctggat gtgttcgtgg actggctgat ccgggcgggc catccgatcg    6420
accgggtcga cgactacgac gactgggtgc gtcggttcga accgcgttg accgcgcttc    6480
ccgagaagcg ccgcgcacag accgtactgc cgctgctgca cgcgttccgc gctccgcagg    6540
caccgttgcg cggcgcaccc gaacccacgg aggtgttcca cgccgcggtg cgcaccgcga    6600
aggtgggccc gggagacatc ccgcacctcg acgaggcgct gatcgacaag tacatacgcg    6660
atctgcgtga gttcggtctg atctgaggta ccaggaggtt tttacaatgg ctgatacttt    6720
gttgattttg ggtgattctc tctctgcagg ctaccgtatg tccgcgagcg cggcatggcc    6780
ggctctgctg aacgataagt ggcagagcaa gaccagcgtg gtcaatgcga gcatcagcgg    6840
cgataccagc cagcagggtc tggcacgtct gccagcgctg ctgaagcaac accagccgcg    6900
ttgggtgctg gttgaactgg gcggcaatga cggtctgcgt ggttttcagc cgcagcagac    6960
cgaacaaacg ttgcgtcaga ttctgcagga cgtcaaggcg gctaacgcgg aaccgctgct    7020
gatgcaaatt cgcctgccgg cgaattatgg tcgtcgttac aacgaggctt tcagcgccat    7080
ttatcctaaa ctggctaaag agtttgacgt gccgctgctg ccgttcttca tggaagaggt    7140
ctacctgaaa ccgcaatgga tgcaagacga cggtattcat ccgaatcgtg atgcacaacc    7200
tttcatcgcg gattggatgg cgaagcaatt gcaaccgctg gtgaaccatg actcgtaaaa    7260
gcttgttgct gcatgcagga ggttttttaca atgaaaacga cccacaccag cttaccattt    7320
```

-continued

```
gccggccaca cgttacattt cgtcgaattt gatccggcga acttttgtga acaagacctg    7380
ttgtggctgc cgcattatgc ccagctgcag cacgcaggcc gtaagcgtaa aactgaacat    7440
ctggccggtc gcattgcggc agtgtatgcc ctgcgcgagt acggctacaa atgcgtgccg    7500
gccattggtg aactgcgtca accgttttgg ccggcagaag tttacggttc catctcccac    7560
tgcggtacta ccgcgttggc ggttgtgtct cgccagccga tcggtattga tattgaagag    7620
atattctctg tccagacggc acgcgagctg acggacaaca tcattacccc ggcagagcac    7680
gagcgtctgg cggactgtgg tctggcgttc agcctggcgc tgaccctggc attcagcgca    7740
aaagagagcg cgttcaaggc ttccgagatc caaaccgatg cgggcttcct ggattatcaa    7800
atcatcagct ggaacaagca acaggttatc attcaccgtg agaatgagat gtttgccgtc    7860
cattggcaga ttaaagagaa aatcgttatc accctgtgcc agcacgactg agaattcggt    7920
tttccgtcct gtcttgattt tcaagcaaac aatgcctccg atttctaatc ggaggcattt    7980
gttttttgttt attgcaaaaa caaaaaatat tgttacaaat ttttacaggc tattaagcct    8040
accgtcataa ataatttgcc atttactagt ttttaattaa ccagaacctt gaccgaacgc    8100
agcggtggta acggcgcagt ggcggttttc atggcttgtt atgactgttt ttttggggta    8160
cagtctatgc ctcgggcatc caagcagcaa gcgcgttacg ccgtgggtcg atgtttgatg    8220
ttatggagca gcaacgatgt tacgcagcag ggcagtcgcc ctaaaacaaa gttaaacatc    8280
atgagggaag cggtgatcgc cgaagtatcg actcaactat cagaggtagt tggcgtcatc    8340
gagcgccatc tcgaaccgac gttgctggcc gtacatttgt acggctccgc agtggatggc    8400
ggcctgaagc cacacagtga tattgatttg ctggttacgg tgaccgtaag gcttgatgaa    8460
acaacgcggc gagctttgat caacgacctt ttggaaactt cggcttcccc tggagagagc    8520
gagattctcc gcgctgtaga agtcaccatt gttgtgcacg acgacatcat tccgtggcgt    8580
tatccagcta agcgcgaact gcaatttgga gaatggcagc gcaatgacat tcttgcaggt    8640
atcttcgagc cagccacgat cgacattgat ctggctatct tgctgacaaa agcaagagaa    8700
catagcgttg ccttggtagg tccagcggcg gaggaactct ttgatccggt tcctgaacag    8760
gatctatttg aggcgctaaa tgaaacctta acgctatgga actcgccgcc cgactgggct    8820
ggcgatgagc gaaatgtagt gcttacgttg tcccgcattt ggtacagcgc agtaaccggc    8880
aaaatcgcgc cgaaggatgt cgctgccgac tgggcaatgg agcgcctgcc ggcccagtat    8940
cagcccgtca tacttgaagc tagacaggct tatcttggac aagaagaaga tcgcttggcc    9000
tcgcgcgcag atcagttgga agaatttgtc cactacgtga aaggcgagat caccaaggta    9060
gtcggcaaat aatgtctaac aattcgttca agccgacgcc gcttcgcggc gcggcttaac    9120
tcaagcgtta gatgcactaa gcacataatt gctcacagcc aaactatcag gtcaagtctg    9180
cttttattat ttttaagcgt gcataataag ccctacacaa attgggagat atatcatgag    9240
gcgcgccacg agaagagtt atgacaaatt aaaattctga ctcttagatt atttccagag    9300
aggctgattt tcccaatctt tgggaaagcc taagtttta gattctattt ctggatacat    9360
ctcaaaagtt ctttttaaat gctgtgcaaa attatgctct ggtttaattc tgtctaagag    9420
atactgaata caacataagc cagtgaaaat tttacggctg tttctttgat taatatcctc    9480
caatacttct ctagagagcc attttccttt taacctatca ggcaatttag gtgattctcc    9540
tagctgtata ttccagagcc ttgaatgatg agcgcaaata tttctaatat gcgacaaaga    9600
ccgtaaccaa gatataaaaa acttgttagg taattggaaa tgagtatgta ttttttgtcg    9660
tgtcttagat ggtaataaat ttgtgtacat tctagataac tgcccaaagg cgattatctc    9720
```

| | |
|---|---|
| caaagccata tatgacggcg gtagtagagg atttgtgtac ttgtttcgat aatgcccgat | 9780 |
| aaattcttct acttttttag attggcaata ttgagtaatc gaatcgatta attcttgatg | 9840 |
| cttcccagtg tcataaaata aactttttatt cagataccaa tgaggatcat aatcatggga | 9900 |
| gtagtgataa atcatttgag ttctgactgc tacttctatc gactccgtag cattaaaaat | 9960 |
| aagcattctc aaggatttat caaacttgta tagatttggc cggcccgtca aaagggcgac | 10020 |
| accccataat tagcccgggc gaaaggccca gtctttcgac tgagcctttc gttttatttg | 10080 |
| atgcctggca gttccctact ctcgcatggg gagtccccac actaccatcg cgctacggc | 10140 |
| gtttcacttc tgagttcggc atggggtcag gtgggaccac cgcgctactg ccgccaggca | 10200 |
| aacaaggggt gttatgagcc atattcaggt ataaatgggc tcgcgataat gttcagaatt | 10260 |
| ggttaattgg ttgtaacact gaccccctatt tgttttattttt tctaaataca ttcaaatatg | 10320 |
| tatccgctca tgagacaata accctgataa atgcttcaat aatattgaaa aggaagaat | 10380 |
| atgagtattc aacatttccg tgtcgccctt attccctttt ttgcggcatt ttgccttcct | 10440 |
| gttttttgctc acccagaaac gctggtgaaa gtaaaagatg ctgaagatca gttgggtgca | 10500 |
| cgagtgggtt acatcgaact ggatctcaac agcggtaaga tccttgagag ttttcgcccc | 10560 |
| gaagaacgtt ttccaatgat gagcactttt aaagttctgc tatgtggcgc ggtattatcc | 10620 |
| cgtattgacg ccgggcaaga gcaactcggt cgccgcatac actattctca gaatgacttg | 10680 |
| gttgagtact caccagtcac agaaaagcat cttacggatg gcatgacagt aagagaatta | 10740 |
| tgcagtgctg ccataaccat gagtgataac actgcggcca acttacttct gacaacgatc | 10800 |
| ggaggaccga aggagctaac cgcttttttg cacaacatgg ggatcatgt aactcgcctt | 10860 |
| gatcgttggg aaccggagct gaatgaagcc ataccaaacg acgagcgtga caccacgatg | 10920 |
| cctgtagcga tggcaacaac gttgcgcaaa ctattaactg gcgaactact tactctagct | 10980 |
| tcccggcaac aattaataga ctggatggag gcggataaag ttgcaggacc acttctgcgc | 11040 |
| tcggcccttc cggctggctg gtttattgct gataaatccg gagccggtga gcgtggttct | 11100 |
| cgcggtatca tcgcagcgct ggggccagat ggtaagccct cccgtatcgt agttatctac | 11160 |
| acgacgggga gtcaggcaac tatggatgaa cgaaatagac agatcgctga gataggtgcc | 11220 |
| tcactgatta agcattggt | 11239 |

<210> SEQ ID NO 7
<211> LENGTH: 940
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

| | |
|---|---|
| ggtaccagga ggttttttaca tggaccgtaa aagcaagcgt ccggacatgc tggttgattc | 60 |
| ctttggtctg gaaagcaccg tgcaggacgg tctggttttc cgtcagtctt tctccattcg | 120 |
| tagctatgag attggtactg atcgtaccgc ctctatcgaa accctgatga atcacctgca | 180 |
| agaaacctct ctgaaccatt gtaagtctac tggcatcctg ctggacggtt tcggtcgtac | 240 |
| cctggagatg tgcaaacgcg acctgatttg gtagtgatc aaaatgcaga tcaaagttaa | 300 |
| ccgttatccg gcatggggtg ataccgttga aatcaacacc cgcttttctc gtctgggcaa | 360 |
| aatcggtatg ggccgtgact ggctgatctc tgactgtaac actggtgaaa ttctggttcg | 420 |
| tgctactagc gcatacgcga tgatgaacca gaaaacccgt cgcctgagca agctgccgta | 480 |

| | |
|---|---|
| cgaggtccac caggagattg ttccgctgtt tgtagacagc ccagtgattg aggattctga | 540 |
| cctgaaagtg cataaattca aagtgaagac cggtgacagc atccaaaaag gcctgacccc | 600 |
| aggttggaac gatctggacg ttaaccagca cgtttccaac gtgaagtata tcggttggat | 660 |
| tctggagagc atgccgaccg aggtcctgga aacccaggag ctgtgttccc tggcgctgga | 720 |
| gtaccgccgt gagtgcggcc gtgacagcgt gctggagtct gtgaccgcta tggacccaag | 780 |
| caaagttggt gttcgtagcc agtaccagca cctgctgcgt ctggaagacg gtactgctat | 840 |
| cgtgaacggt gcaactgaat ggcgtcctaa aaacgcgggt gcaaacggtg ctatcagcac | 900 |
| cggtaaaacc tctaacggta actccgtgag ctaaaagctt | 940 |

<210> SEQ ID NO 8
<211> LENGTH: 11601
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

| | |
|---|---|
| aaaagcagag cattacgctg acttgacggg acggcgcaag ctcatgacca aaatccctta | 60 |
| acgtgagtta cgcgcgcgtc gttccactga gcgtcagacc ccgtagaaaa gatcaaagga | 120 |
| tcttcttgag atcctttttt tctgcgcgta atctgctgct tgcaaacaaa aaaaccaccg | 180 |
| ctaccagcgg tggtttgttt gccggatcaa gagctaccaa ctcttttttcc gaaggtaact | 240 |
| ggcttcagca gagcgcagat accaaatact gttcttctag tgtagccgta gttagcccac | 300 |
| cacttcaaga actctgtagc accgcctaca tacctcgctc tgctaatcct gttaccagtg | 360 |
| gctgctgcca gtggcgataa gtcgtgtctt accgggttgg actcaagacg atagttaccg | 420 |
| gataaggcgc agcggtcggg ctgaacgggg ggttcgtgca cacagcccag cttggagcga | 480 |
| acgacctaca ccgaactgag atacctacag cgtgagctat gagaaagcgc cacgcttccc | 540 |
| gaagggagaa aggcggacag gtatccggta agcggcaggg tcggaacagg agagcgcacg | 600 |
| agggagcttc caggggggaaa cgcctggtat ctttatagtc ctgtcgggtt tcgccacctc | 660 |
| tgacttgagc gtcgattttt gtgatgctcg tcaggggggc ggagcctatg gaaaaacgcc | 720 |
| agcaacgcgg ccttttttacg gttcctggcc ttttgctggc cttttgctca catgttcttt | 780 |
| cctgcgttat cccctgattc tgtggataac cgtattaccg cctttgagtg agctgatacc | 840 |
| gctcgccgca gccgaacgac cgagcgcagc gagtcagtga gcgaggaagc ggaaggcgag | 900 |
| agtagggaac tgccaggcat caaactaagc agaaggcccc tgacggatgg ccttttttgcg | 960 |
| tttctacaaa ctcttttctgt gttgtaaaac gacggccagt cttaagctcg gccccctgg | 1020 |
| gcggttctga taacgagtaa tcgttaatcc gcaaataacg taaaaacccg cttcggcggg | 1080 |
| ttttttttatg gggggagttt agggaaagag catttgtcag aatatttaag ggcgcctgtc | 1140 |
| actttgcttg atatatgaga attatttaac cttataaatg agaaaaaagc aacgcacttt | 1200 |
| aaataagata cgttgctttt tcgattgatg aacacctata attaaactat tcatctatta | 1260 |
| tttatgattt tttgtatata caatatttct agtttgttaa agagaattaa gaaaataaat | 1320 |
| ctcgaaaata ataaagggaa atcagttttt tgatatcaaa attatacatg tcaacgataa | 1380 |
| tacaaaatat aatacaaact ataagatgtt atcagtattt attatgcatt tagaataaat | 1440 |
| tttgtgtcgc ccttcgctga acctgcaggc gagcatttca acgatgatga atgggacggc | 1500 |
| gaacccactg aacccgtcgc cattgaccca gaaccgcgca aagaacggga aaaaattgat | 1560 |

```
ctcgatctgg aggatgaacc agaggaaaac cgcaaaccgc aaaaaatcaa agtgaagtta    1620
gccgatggga aagagcggga actcgcccat actcaaacca caacttttg ggatgctgat     1680 ggtaaaccca tttccgccca agaatttatc gaaaagctat ttggcgacct gcccgacctc    1740
ttcaaggatg aagccgaact acgcaccatc tgggggaaac ccgatacccg taaatcgttc    1800
ctgaccggac tcgcggaaaa aggctacggt gacacccaac tgaaggcgat cgcacgcatt    1860
gccgaagcgg aaaaaagtga tgtctatgat gtcctgactt gggttgccta acaccaaa     1920 cccattagca gagaagagcg agtaattaag catcgagatc tgattttctc gaagtacacc    1980
ggaaagcagc aagaattttt agattttgtc ctagaccaat acattcgaga aggagtggag    2040
gaacttgatc gggggaaact gcctaccctc atcgaaatca ataccaaac cgttaatgaa     2100 ggtttagtga tcttgggtca ggatatcggt caagtattcg cagattttca ggcggattta    2160
tataccgaag atgtggcata aaaaaggacg gcgatcgccg ggggcgttgc ctgccttgag    2220
cggccgcttg tagcaattgc tactaaaaac tgcgatcgct gctgaaatga gctggaattt    2280
tgtccctctc agctcaaaaa gtatcaatga ttacttaatg tttgttctgc gcaaacttct    2340
tgcagaacat gcatgattta caaaaagttg tagtttctgt taccaattgc gaatcgagaa    2400
ctgcctaatc tgccgagtat gcgatccttt agcaggagga aaaccatatg caagaactgg    2460
ccctgagaag cgagctggac ttcaatagcg aaacctataa agatgcgtat agccgtatta    2520
acgccattgt gatcgaaggc gagcaagaag cataccaaaa ctacctggac atggcgcaac    2580
tgctgccgga ggacgaggct gagctgattc gtttgagcaa gatggagaac cgtcacaaaa    2640
agggttttca agcgtgcggc aagaacctca atgtgactcc ggatatggat tatgcacagc    2700
agttctttgc ggagctgcac ggcaatttc agaaggctaa agccgagggt aagattgtta    2760
cctgcctgct catccaaagc ctgatcatcg aggcgtttgc gattgcagcc tacaacattt    2820
acattccagt ggctgatccg tttgcacgta aaatcaccga gggtgtcgtc aaggatgagt    2880
atacccacct gaatttcggc gaagtttggt tgaaggaaca ttttgaagca agcaaggcgg    2940
agttggagga cgccaacaaa gagaacttac cgctggtctg gcagatgttg aaccaggtcg    3000
aaaaggatgc cgaagtgctg ggtatggaga agaggctct ggtggaggac tttatgatta    3060
gctatggtga ggcactgagc aacatcggct tttctacgag agaaatcatg aagatgagcg    3120
cgtacggtct gcgtgcagca taagagctcg aggaggtttt tacaatgacc agcgatgttc    3180
acgacgccac agacggcgtc accgaaaccg cactcgacga cgagcagtcg acccgccgca    3240
tcgccgagct gtacgccacc gatcccgagt tcgccgccgc cgcaccgttg cccgccgtgg    3300
tcgacgcggc gcacaaaccc gggctgcggc tggcagagat cctgcagacc ctgttcaccg    3360
gctacggtga ccgccggcg ctgggatacc gcgccgtga actggccacc gacgagggcg      3420
ggcgcaccgt gacgcgtctg ctgccgcggt tcgacaccct cacctacgcc aggtgtggt     3480 cgcgcgtgca agcggtcgcc gcggccctgc gccacaactt cgcgcagccg atctaccccg    3540
gcgacgccgt cgcgacgatc ggtttcgcga gtcccgatta cctgacgctg gatctcgtat    3600
gcgcctacct gggcctcgtg agtgttccgc tgcagcacaa cgcaccggtc agccggctcg    3660
ccccgatcct ggccgaggtc gaaccgcgga tcctcaccgt gagcgccgaa tacctcgacc    3720
tcgcagtcga atccgtgcgg gacgtcaact cggtgtcgca gctcgtggtg ttcgaccatc    3780
accccgaggt cgacgaccac cgcgacgcac tggcccgcgc gcgtgaacaa ctcgccggca    3840
agggcatcgc cgtcaccacc ctggacgcga tcgccgacga gggcgccggg ctgccggccg    3900
```

```
aaccgatcta caccgccgac catgatcagc gcctcgcgat gatcctgtac acctcgggtt   3960
ccaccggcgc acccaagggt gcgatgtaca ccgaggcgca ggtggcgcgg ctgtggacca   4020
tgtcgttcat cacgggtgac cccacgccgg tcatcaacgt caacttcatg ccgctcaacc   4080
acctgggcgg gcgcatcccc atttccaccg ccgtgcagaa cggtggaacc agttacttcg   4140
taccggaatc cgacatgtcc acgctgttcg aggatctcgc gctggtgcgc ccgaccgaac   4200
tcggcctggt tccgcgcgtc gccgacatgc tctaccagca ccacctcgcc accgtcgacc   4260
gcctggtcac gcagggcgcc gacgaactga ccgccgagaa gcaggccggt gccgaactgc   4320
gtgagcaggt gctcggcgga cgcgtgatca ccggattcgt cagcaccgca ccgctggccg   4380
cggagatgag ggcgttcctc gacatcaccc tgggcgcaca catcgtcgac ggctacgggc   4440
tcaccgagac cggcgccgtg acacgcgacg gtgtgatcgt gcggccaccg gtgatcgact   4500
acaagctgat cgacgttccc gaactcggct acttcagcac cgacaagccc tacccgcgtg   4560
gcgaactgct ggtcaggtcg caaacgctga ctcccgggta ctacaagcgc cccgaggtca   4620
ccgcgagcgt cttcgaccgg gacggctact accacaccgg cgacgtcatg ccgagaccg   4680
cacccgacca cctggtgtac gtggaccgtc gcaacaacgt cctcaaactc gcgcagggcg   4740
agttcgtggc ggtcgccaac ctggaggcgg tgttctccgg cgcggcgctg gtgcgccaga   4800
tcttcgtgta cggcaacagc gagcgcagtt ccttctggc cgtggtggtc ccgacgccgg   4860
aggcgctcga gcagtacgat ccggccgcgc tcaaggccgc gctggccgac tcgctgcagc   4920
gcaccgcacg cgacgccgaa ctgcaatcct acgaggtgcc ggccgatttc atcgtcgaga   4980
ccgagccgtt cagcgccgcc aacgggctgc tgtcgggtgt cggaaaactg ctgcggccca   5040
acctcaaaga ccgctacggg cagcgcctgg agcagatgta cgccgatatc gcggccacgc   5100
aggccaacca gttgcgcgaa ctgcggcgcg cggccgccac acaaccggtg atcgacaccc   5160
tcacccaggc cgctgccacg atcctcggca ccgggagcga ggtggcatcc gacgcccact   5220
tcaccgacct gggcgggat tccctgtcgg cgctgacact ttcgaacctg ctgagcgatt   5280
tcttcggttt cgaagttccc gtcggcacca tcgtgaaccc ggccaccaac ctcgcccaac   5340
tcgcccagca catcgaggcg cagcgcaccg cgggtgaccg caggccgagt ttcaccaccg   5400
tgcacggcgc ggacgccacc gagatccggg cgagtgagct gaccctggac aagttcatcg   5460
acgccgaaac gctccgggcc gcaccgggtc tgcccaaggt caccaccgag ccacggacgg   5520
tgttgctctc gggcgccaac ggctggctgg gccggttcct cacgttgcag tggctggaac   5580
gcctggcacc tgtcggcggc accctcatca cgatcgtgcg gggccgcgac gacgccgcgg   5640
cccgcgcacg gctgacccag gcctacgaca ccgatcccga gttgtcccgc cgcttcgccg   5700
agctggccga ccgccacctg cgggtggtcg ccggtgacat cggcgacccg aatctgggcc   5760
tcacacccga gatctggcac cggctcgccg ccgaggtcga cctggtggtg catccggcag   5820
cgctggtcaa ccacgtgctc ccctaccggc agctgttcgg ccccaacgtc gtgggcacgg   5880
ccgaggtgat caagctggcc ctcaccgaac ggatcaagcc cgtcacgtac ctgtccaccg   5940
tgtcggtggc catggggatc cccgacttcg aggaggacgg cgacatccgg accgtgagcc   6000
cggtgcgccc gctcgacggc ggatacgcca acggctacgg caacagcaag tgggccggcg   6060
aggtgctgct gcgggaggcc cacgatctgt gcgggctgcc cgtggcgacg ttccgctcgg   6120
acatgatcct ggcgcatccg cgctaccgcg gtcaggtcaa cgtgccagac atgttcacgc   6180
gactcctgtt gagcctcttg atcaccgcg tcgcgccgcg gtcgttctac atcggagacg   6240
gtgagcgccc gcgggcgcac tacccccggcc tgacggtcga tttcgtggcc gaggcggtca   6300
```

```
cgacgctcgg cgcgcagcag cgcgagggat acgtgtccta cgacgtgatg aacccgcacg   6360
acgacgggat ctccctggat gtgttcgtgg actggctgat ccgggcgggc catccgatcg   6420
accgggtcga cgactacgac gactgggtgc gtcggttcga gaccgcgttg accgcgcttc   6480
ccgagaagcg ccgcgcacag accgtactgc cgctgctgca cgcgttccgc gctccgcagg   6540
caccgttgcg cggcgcaccc gaacccacgg aggtgttcca cgccgcggtg cgcaccgcga   6600
aggtgggccc gggagacatc ccgcacctcg acgaggcgct gatcgacaag tacatacgcg   6660
atctgcgtga gttcggtctg atctgaggta ccaggaggtt tttacatgga ccgtaaaagc   6720
aagcgtccgg acatgctggt tgattccttt ggtctggaaa gcaccgtgca ggacggtctg   6780
gttttccgtc agtctttctc cattcgtagc tatgagattg gtactgatcg taccgcctct   6840
atcgaaaccc tgatgaatca cctgcaagaa acctctctga accattgtaa gtctactggc   6900
atcctgctgg acggtttcgg tcgtaccctg agatgtgcaa acgcgacct gatttgggta   6960 gtgatcaaaa tgcagatcaa agttaaccgt tatccggcat ggggtgatac cgttgaaatc   7020
aacacccgct tttctcgtct gggcaaaatc ggtatgggcc gtgactggct gatctctgac   7080
tgtaacactg gtgaaattct ggttcgtgct actagcgcat acgcgatgat gaaccagaaa   7140
acccgtcgcc tgagcaagct gccgtacgag gtccaccagg agattgttcc gctgtttgta   7200
gacagcccag tgattgagga ttctgacctg aaagtgcata aattcaaagt gaagaccggt   7260
gacagcatcc aaaaaggcct gacccaggt tggaacgatc tggacgttaa ccagcacgtt   7320
tccaacgtga gtatatcgg ttggattctg gagagcatgc cgaccgaggt cctggaaacc   7380
caggagctgt gttccctggc gctggagtac cgccgtgagt gcggccgtga cagcgtgctg   7440
gagtctgtga ccgctatgga cccaagcaaa gttggtgttc gtagccagta ccagcacctg   7500
ctgcgtctgg aagacggtac tgctatcgtg aacggtgcaa ctgaatggcg tcctaaaaac   7560
gcgggtgcaa acggtgctat cagcaccggt aaaacctcta acggtaactc cgtgagctaa   7620
aagcttgttg ctgcatgcag gaggttttta caatgaaaac gacccacacc agcttaccat   7680
ttgccggcca cacgttacat ttcgtcgaat ttgatccggc gaacttttgt gaacaagacc   7740
tgttgtggct gccgcattat gcccagctgc agcacgcagg ccgtaagcgt aaaactgaac   7800
atctggccgg tcgcattgcg gcagtgtatg ccctgcgcga gtacggctac aaatgcgtgc   7860
cggccattgg tgaactgcgt caaccggttt ggccggcaga gtttacggt tccatctccc   7920 actgcggtac taccgcgttg gcggttgtgt ctcgccagcc gatcggtatt gatattgaag   7980
agatattctc tgtccagacg gcacgcgagc tgacggacaa catcattacc ccggcagagc   8040
acgagcgtct ggcggactgt ggtctggcgt tcagcctggc gctgacctg gcattcagcg   8100 caaaagagag cgcgttcaag gcttccgaga tccaaaccga tgcgggcttc ctggattatc   8160
aaatcatcag ctggaacaag caacaggtta tcattcaccg tgagaatgag atgtttgccg   8220
tccattggca gattaaagag aaaatcgtta tcaccctgtg ccagcacgac tgagaattcg   8280
gttttccgtc ctgtcttgat tttcaagcaa acaatgcctc cgatttctaa tcggaggcat   8340
ttgtttttgt ttattgcaaa acaaaaaaat attgttacaa attttttcag gctattaagc   8400
ctaccgtcat aaataatttg ccatttacta gttttttaatt aaccagaacc ttgaccgaac   8460
gcagcggtgg taacggcgca gtggcggttt tcatggcttg ttatgactgt ttttttgggg   8520
tacagtctat gcctcgggca tccaagcagc aagcgcgtta cgccgtgggt cgatgtttga   8580
tgttatggag cagcaacgat gttacgcagc agggcagtcg ccctaaaaca aagttaaaca   8640
```

```
tcatgaggga agcggtgatc gccgaagtat cgactcaact atcagaggta gttggcgtca    8700
tcgagcgcca tctcgaaccg acgttgctgg ccgtacattt gtacggctcc gcagtggatg    8760
gcggcctgaa gccacacagt gatattgatt tgctggttac ggtgaccgta aggcttgatg    8820
aaacaacgcg gcgagctttg atcaacgacc ttttggaaac ttcggcttcc cctggagaga    8880
gcgagattct ccgcgctgta gaagtcacca ttgttgtgca cgacgacatc attccgtggc    8940
gttatccagc taagcgcgaa ctgcaatttg gagaatggca gcgcaatgac attcttgcag    9000
gtatcttcga gccagccacg atcgacattg atctggctat cttgctgaca aaagcaagag    9060
aacatagcgt tgccttggta ggtccagcgg cggaggaact cttttgatccg gttcctgaac    9120
aggatctatt tgaggcgcta atgaaacct taacgctatg gaactcgccg cccgactggg    9180
ctggcgatga gcgaaatgta gtgcttacgt tgtcccgcat ttggtacagc gcagtaaccg    9240
gcaaaatcgc gccgaaggat gtcgctgccg actgggcaat ggagcgcctg ccggcccagt    9300
atcagcccgt catacttgaa gctagacagg cttatcttgg acaagaagaa gatcgcttgg    9360
cctcgcgcgc agatcagttg gaagaatttg tccactacgt gaaaggcgag atcaccaagg    9420
tagtcggcaa ataatgtcta acaattcgtt caagccgacg ccgcttcgcg gcgcggctta    9480
actcaagcgt tagatgcact aagcacataa ttgctcacag ccaaactatc aggtcaagtc    9540
tgcttttatt attttaagc gtgcataata agcctcacac aaattgggag atatatcatg    9600
aggcgcgcca cgagaaagag ttatgacaaa ttaaattct gactcttaga ttatttccag    9660
agaggctgat tttcccaatc tttgggaaag cctaagtttt tagattctat ttctggatac    9720
atctcaaaag ttctttttaa atgctgtgca aaattatgct ctggtttaat tctgtctaag    9780
agatactgaa tacaacataa gccagtgaaa attttacggc tgtttctttg attaatatcc    9840
tccaatactt ctctagagag ccatttttcct tttaacctat caggcaattt aggtgattct    9900
cctagctgta tattccagag ccttgaatga tgagcgcaaa tatttctaat atgcgacaaa    9960
gaccgtaacc aagatataaa aaacttgtta ggtaattgga aatgagtatg tattttttgt    10020
cgtgtcttag atggtaataa atttgtgtac attctagata actgcccaaa ggcgattatc    10080
tccaaagcca tatgacgg cggtagtaga ggatttgtgt acttgtttcg ataatgcccg      10140
ataaattctt ctacttttttt agattggcaa tattgagtaa tcgaatcgat taattcttga    10200
tgcttcccag tgtcataaaa taaactttta ttcagatacc aatgaggatc ataatcatgg    10260
gagtagtgat aaatcatttg agttctgact gctacttcta tcgactccgt agcattaaaa    10320
ataagcattc tcaaggattt atcaaacttg tatagatttg gccggcccgt caaaagggcg    10380
acaccccata attagcccgg gcgaaaggcc cagtcttttcg actgagcctt tcgttttatt    10440
tgatgcctgg cagttcccta ctctcgcatg gggagtcccc acactaccat cggcgctacg    10500
gcgtttcact tctgagttcg gcatggggtc aggtgggacc accgcgctac tgccgccagg    10560
caaacaaggg gtgttatgag ccatattcag gtataaatgg gctcgcgata atgttcagaa    10620
ttggttaatt ggttgtaaca ctgacccca tttgtttatt tttctaaata cattcaaata    10680
tgtatccgct catgagacaa taaccctgat aaatgcttca ataatattga aaaggaaga    10740
atatgagtat tcaacatttc cgtgtcgccc ttattccctt ttttgcggca ttttgccttc    10800
ctgttttgc tcacccagaa acgctggtga agtaaaaga tgctgaagat cagttgggtg    10860
cacgagtggg ttacatcgaa ctggatctca acagcggtaa gatccttgag agttttcgcc    10920
ccgaagaacg ttttccaatg atgagcactt ttaaagttct gctatgtggc gcggtattat    10980
cccgtattga cgccgggcaa gagcaactcg gtcgccgcat acactattct cagaatgact    11040
```

-continued

```
tggttgagta ctcaccagtc acagaaaagc atcttacgga tggcatgaca gtaagagaat    11100
tatgcagtgc tgccataacc atgagtgata acactgcggc caacttactt ctgacaacga    11160
tcggaggacc gaaggagcta accgcttttt tgcacaacat gggggatcat gtaactcgcc    11220
ttgatcgttg ggaaccggag ctgaatgaag ccataccaaa cgacgagcgt gacaccacga    11280
tgcctgtagc gatggcaaca acgttgcgca aactattaac tggcgaacta cttactctag    11340
cttcccggca acaattaata gactggatgg aggcggataa agttgcagga ccacttctgc    11400
gctcggccct tccggctggc tggtttattg ctgataaatc cggagccggt gagcgtggtt    11460
ctcgcggtat catcgcagcg ctggggccag atggtaagcc ctcccgtatc gtagttatct    11520
acacgacggg gagtcaggca actatggatg aacgaaatag acagatcgct gagataggtg    11580
cctcactgat taagcattgg t                                              11601
```

<210> SEQ ID NO 9
<211> LENGTH: 1173
<212> TYPE: PRT
<213> ORGANISM: Mycobacterium smegmatis

<400> SEQUENCE: 9

```
Met Thr Ser Asp Val His Asp Ala Thr Asp Gly Val Thr Glu Thr Ala
1               5                   10                  15

Leu Asp Asp Glu Gln Ser Thr Arg Arg Ile Ala Glu Leu Tyr Ala Thr
            20                  25                  30

Asp Pro Glu Phe Ala Ala Ala Pro Leu Pro Ala Val Val Asp Ala
        35                  40                  45

Ala His Lys Pro Gly Leu Arg Leu Ala Glu Ile Leu Gln Thr Leu Phe
    50                  55                  60

Thr Gly Tyr Gly Asp Arg Pro Ala Leu Gly Tyr Arg Ala Arg Glu Leu
65                  70                  75                  80

Ala Thr Asp Glu Gly Gly Arg Thr Val Thr Arg Leu Leu Pro Arg Phe
                85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
        115                 120                 125

Val Ala Thr Ile Gly Phe Ala Ser Pro Asp Tyr Leu Thr Leu Asp Leu
    130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175

Leu Thr Val Ser Ala Glu Tyr Leu Asp Leu Ala Val Glu Ser Val Arg
            180                 185                 190

Asp Val Asn Ser Val Ser Gln Leu Val Val Phe Asp His His Pro Glu
        195                 200                 205

Val Asp Asp His Arg Asp Ala Leu Ala Arg Ala Arg Glu Gln Leu Ala
    210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255

Leu Ala Met Ile Leu Tyr Thr Ser Gly Ser Thr Gly Ala Pro Lys Gly
            260                 265                 270
```

```
Ala Met Tyr Thr Glu Ala Met Val Ala Arg Leu Trp Thr Met Ser Phe
            275                 280                 285

Ile Thr Gly Asp Pro Thr Pro Val Ile Asn Val Asn Phe Met Pro Leu
    290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
            340                 345                 350

Ala Asp Met Leu Tyr Gln His His Leu Ala Thr Val Asp Arg Leu Val
        355                 360                 365

Thr Gln Gly Ala Asp Glu Leu Thr Ala Glu Lys Gln Ala Gly Ala Glu
    370                 375                 380

Leu Arg Glu Gln Val Leu Gly Arg Val Ile Thr Gly Phe Val Ser
385                 390                 395                 400

Thr Ala Pro Leu Ala Ala Glu Met Arg Ala Phe Leu Asp Ile Thr Leu
                405                 410                 415

Gly Ala His Ile Val Asp Gly Tyr Gly Leu Thr Glu Thr Gly Ala Val
            420                 425                 430

Thr Arg Asp Gly Val Ile Val Arg Pro Pro Val Ile Asp Tyr Lys Leu
        435                 440                 445

Ile Asp Val Pro Glu Leu Gly Tyr Phe Ser Thr Asp Lys Pro Tyr Pro
    450                 455                 460

Arg Gly Glu Leu Leu Val Arg Ser Gln Thr Leu Thr Pro Gly Tyr Tyr
465                 470                 475                 480

Lys Arg Pro Glu Val Thr Ala Ser Val Phe Asp Arg Asp Gly Tyr Tyr
                485                 490                 495

His Thr Gly Asp Val Met Ala Glu Thr Ala Pro Asp His Leu Val Tyr
            500                 505                 510

Val Asp Arg Arg Asn Asn Val Leu Lys Leu Ala Gln Gly Glu Phe Val
        515                 520                 525

Ala Val Ala Asn Leu Glu Ala Val Phe Ser Gly Ala Ala Leu Val Arg
    530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
                565                 570                 575

Lys Ala Ala Leu Ala Asp Ser Leu Gln Arg Thr Ala Arg Asp Ala Glu
            580                 585                 590

Leu Gln Ser Tyr Glu Val Pro Ala Asp Phe Ile Val Glu Thr Glu Pro
        595                 600                 605

Phe Ser Ala Ala Asn Gly Leu Leu Ser Gly Val Gly Lys Leu Leu Arg
    610                 615                 620

Pro Asn Leu Lys Asp Arg Tyr Gly Gln Arg Leu Glu Gln Met Tyr Ala
625                 630                 635                 640

Asp Ile Ala Ala Thr Gln Ala Asn Gln Leu Arg Glu Leu Arg Arg Ala
                645                 650                 655

Ala Ala Thr Gln Pro Val Ile Asp Thr Leu Thr Gln Ala Ala Ala Thr
            660                 665                 670

Ile Leu Gly Thr Gly Ser Glu Val Ala Ser Asp Ala His Phe Thr Asp
        675                 680                 685
```

-continued

```
Leu Gly Gly Asp Ser Leu Ser Ala Leu Thr Leu Ser Asn Leu Leu Ser
            690             695             700

Asp Phe Gly Phe Glu Val Pro Val Gly Thr Ile Val Asn Pro Ala
705             710             715             720

Thr Asn Leu Ala Gln Leu Ala Gln His Ile Glu Ala Gln Arg Thr Ala
                725             730             735

Gly Asp Arg Arg Pro Ser Phe Thr Thr Val His Gly Ala Asp Ala Thr
            740             745             750

Glu Ile Arg Ala Ser Glu Leu Thr Leu Asp Lys Phe Ile Asp Ala Glu
                755             760             765

Thr Leu Arg Ala Ala Pro Gly Leu Pro Lys Val Thr Thr Glu Pro Arg
770             775             780

Thr Val Leu Leu Ser Gly Ala Asn Gly Trp Leu Gly Arg Phe Leu Thr
785             790             795             800

Leu Gln Trp Leu Glu Arg Leu Ala Pro Val Gly Gly Thr Leu Ile Thr
                805             810             815

Ile Val Arg Gly Arg Asp Asp Ala Ala Ala Arg Ala Arg Leu Thr Gln
            820             825             830

Ala Tyr Asp Thr Asp Pro Glu Leu Ser Arg Arg Phe Ala Glu Leu Ala
                835             840             845

Asp Arg His Leu Arg Val Val Ala Gly Asp Ile Gly Asp Pro Asn Leu
850             855             860

Gly Leu Thr Pro Glu Ile Trp His Arg Leu Ala Ala Glu Val Asp Leu
865             870             875             880

Val Val His Pro Ala Ala Leu Val Asn His Val Leu Pro Tyr Arg Gln
                885             890             895

Leu Phe Gly Pro Asn Val Val Gly Thr Ala Glu Val Ile Lys Leu Ala
            900             905             910

Leu Thr Glu Arg Ile Lys Pro Val Thr Tyr Leu Ser Thr Val Ser Val
        915             920             925

Ala Met Gly Ile Pro Asp Phe Glu Glu Asp Gly Asp Ile Arg Thr Val
    930             935             940

Ser Pro Val Arg Pro Leu Asp Gly Gly Tyr Ala Asn Gly Tyr Gly Asn
945             950             955             960

Ser Lys Trp Ala Gly Glu Val Leu Leu Arg Glu Ala His Asp Leu Cys
            965             970             975

Gly Leu Pro Val Ala Thr Phe Arg Ser Asp Met Ile Leu Ala His Pro
            980             985             990

Arg Tyr Arg Gly Gln Val Asn Val Pro Asp Met Phe Thr Arg Leu Leu
        995             1000            1005

Leu Ser Leu Leu Ile Thr Gly Val Ala Pro Arg Ser Phe Tyr Ile
    1010            1015            1020

Gly Asp Gly Glu Arg Pro Arg Ala His Tyr Pro Gly Leu Thr Val
    1025            1030            1035

Asp Phe Val Ala Glu Ala Val Thr Thr Leu Gly Ala Gln Gln Arg
    1040            1045            1050

Glu Gly Tyr Val Ser Tyr Asp Val Met Asn Pro His Asp Asp Gly
    1055            1060            1065

Ile Ser Leu Asp Val Phe Val Asp Trp Leu Ile Arg Ala Gly His
    1070            1075            1080

Pro Ile Asp Arg Val Asp Asp Tyr Asp Asp Trp Val Arg Arg Phe
    1085            1090            1095

Glu Thr Ala Leu Thr Ala Leu Pro Glu Lys Arg Arg Ala Gln Thr
```

```
                    1100                1105                1110
Val Leu Pro Leu Leu His Ala Phe Arg Ala Pro Gln Ala Pro Leu
        1115                1120                1125

Arg Gly Ala Pro Glu Pro Thr Glu Val Phe His Ala Ala Val Arg
    1130                1135                1140

Thr Ala Lys Val Gly Pro Gly Asp Ile Pro His Leu Asp Glu Ala
1145                1150                1155

Leu Ile Asp Lys Tyr Ile Arg Asp Leu Arg Glu Phe Gly Leu Ile
    1160                1165                1170

<210> SEQ ID NO 10
<211> LENGTH: 206
<212> TYPE: PRT
<213> ORGANISM: Escherichia coli

<400> SEQUENCE: 10

Met Lys Thr Thr His Thr Ser Leu Pro Phe Ala Gly His Thr Leu His
1               5                   10                  15

Phe Val Glu Phe Asp Pro Ala Asn Phe Cys Glu Gln Asp Leu Leu Trp
            20                  25                  30

Leu Pro His Tyr Ala Gln Leu Gln His Ala Gly Arg Lys Arg Lys Thr
        35                  40                  45

Glu His Leu Ala Gly Arg Ile Ala Ala Val Tyr Ala Leu Arg Glu Tyr
    50                  55                  60

Gly Tyr Lys Cys Val Pro Ala Ile Gly Glu Leu Arg Gln Pro Val Trp
65                  70                  75                  80

Pro Ala Glu Val Tyr Gly Ser Ile Ser His Cys Gly Thr Thr Ala Leu
                85                  90                  95

Ala Val Val Ser Arg Gln Pro Ile Gly Ile Asp Ile Glu Glu Ile Phe
            100                 105                 110

Ser Val Gln Thr Ala Arg Glu Leu Thr Asp Asn Ile Ile Thr Pro Ala
        115                 120                 125

Glu His Glu Arg Leu Ala Asp Cys Gly Leu Ala Phe Ser Leu Ala Leu
    130                 135                 140

Thr Leu Ala Phe Ser Ala Lys Glu Ser Ala Phe Lys Ala Ser Glu Ile
145                 150                 155                 160

Gln Thr Asp Ala Gly Phe Leu Asp Tyr Gln Ile Ile Ser Trp Asn Lys
                165                 170                 175

Gln Gln Val Ile Ile His Arg Glu Asn Glu Met Phe Ala Val His Trp
            180                 185                 190

Gln Ile Lys Glu Lys Ile Val Ile Thr Leu Cys Gln His Asp
        195                 200                 205

<210> SEQ ID NO 11
<211> LENGTH: 295
<212> TYPE: PRT
<213> ORGANISM: Acinetobacter sp.

<400> SEQUENCE: 11

Met Asn Ala Lys Leu Lys Lys Leu Phe Gln Gln Lys Val Asp Gly Lys
1               5                   10                  15

Thr Ile Ile Val Thr Gly Ala Ser Ser Gly Ile Gly Leu Thr Val Ser
            20                  25                  30

Lys Tyr Leu Ala Gln Ala Gly Ala His Val Leu Leu Leu Ala Arg Thr
        35                  40                  45

Lys Glu Lys Leu Asp Glu Val Lys Ala Glu Ile Glu Ala Glu Gly Gly
```

```
            50                  55                  60
Lys Ala Thr Val Phe Pro Cys Asp Leu Asn Asp Met Glu Ser Ile Asp
 65                  70                  75                  80

Ala Val Ser Lys Glu Ile Leu Ala Ala Val Asp His Ile Asp Ile Leu
                 85                  90                  95

Val Asn Asn Ala Gly Arg Ser Ile Arg Arg Ala Val His Glu Ser Val
            100                 105                 110

Asp Arg Phe His Asp Phe Glu Arg Thr Met Gln Leu Asn Tyr Phe Gly
            115                 120                 125

Ala Val Arg Leu Val Leu Asn Val Leu Pro His Met Met Gln Arg Lys
        130                 135                 140

Asp Gly Gln Ile Ile Asn Ile Ser Ser Ile Gly Val Leu Ala Asn Ala
145                 150                 155                 160

Thr Arg Phe Ser Ala Tyr Val Ala Ser Lys Ala Ala Leu Asp Ala Phe
                165                 170                 175

Ser Arg Cys Leu Ser Ala Glu Val His Ser His Lys Ile Ala Ile Thr
            180                 185                 190

Ser Ile Tyr Met Pro Leu Val Arg Thr Pro Met Ile Ala Pro Thr Lys
        195                 200                 205

Ile Tyr Lys Tyr Val Pro Thr Leu Ser Pro Glu Glu Ala Ala Asp Leu
210                 215                 220

Ile Ala Tyr Ala Ile Val Lys Arg Pro Lys Lys Ile Ala Thr Asn Leu
225                 230                 235                 240

Gly Arg Leu Ala Ser Ile Thr Tyr Ala Ile Ala Pro Asp Ile Asn Asn
                245                 250                 255

Ile Leu Met Ser Ile Gly Phe Asn Leu Phe Pro Ser Ser Thr Ala Ser
            260                 265                 270

Val Gly Glu Gln Glu Lys Leu Asn Leu Ile Gln Arg Ala Tyr Ala Arg
        275                 280                 285

Leu Phe Pro Gly Glu His Trp
        290                 295

<210> SEQ ID NO 12
<211> LENGTH: 561
<212> TYPE: PRT
<213> ORGANISM: Escherichia coli

<400> SEQUENCE: 12

Met Lys Lys Val Trp Leu Asn Arg Tyr Pro Ala Asp Val Pro Thr Glu
 1               5                  10                  15

Ile Asn Pro Asp Arg Tyr Gln Ser Leu Val Asp Met Phe Glu Gln Ser
                20                  25                  30

Val Ala Arg Tyr Ala Asp Gln Pro Ala Phe Val Asn Met Gly Glu Val
            35                  40                  45

Met Thr Phe Arg Lys Leu Glu Glu Arg Ser Arg Ala Phe Ala Ala Tyr
        50                  55                  60

Leu Gln Gln Gly Leu Gly Leu Lys Lys Gly Asp Arg Val Ala Leu Met
 65                  70                  75                  80

Met Pro Asn Leu Leu Gln Tyr Pro Val Ala Leu Phe Gly Ile Leu Arg
                85                  90                  95

Ala Gly Met Ile Val Val Asn Val Asn Pro Leu Tyr Thr Pro Arg Glu
            100                 105                 110

Leu Glu His Gln Leu Asn Asp Ser Gly Ala Ser Ala Ile Val Ile Val
        115                 120                 125
```

```
Ser Asn Phe Ala His Thr Leu Glu Lys Val Val Asp Lys Thr Ala Val
130                 135                 140

Gln His Val Ile Leu Thr Arg Met Gly Asp Gln Leu Ser Thr Ala Lys
145                 150                 155                 160

Gly Thr Val Val Asn Phe Val Val Lys Tyr Ile Lys Arg Leu Val Pro
                165                 170                 175

Lys Tyr His Leu Pro Asp Ala Ile Ser Phe Arg Ser Ala Leu His Asn
            180                 185                 190

Gly Tyr Arg Met Gln Tyr Val Lys Pro Glu Leu Val Pro Glu Asp Leu
        195                 200                 205

Ala Phe Leu Gln Tyr Thr Gly Gly Thr Thr Gly Val Ala Lys Gly Ala
210                 215                 220

Met Leu Thr His Arg Asn Met Leu Ala Asn Leu Glu Gln Val Asn Ala
225                 230                 235                 240

Thr Tyr Gly Pro Leu Leu His Pro Gly Lys Glu Leu Val Val Thr Ala
                245                 250                 255

Leu Pro Leu Tyr His Ile Phe Ala Leu Thr Ile Asn Cys Leu Leu Phe
            260                 265                 270

Ile Glu Leu Gly Gly Gln Asn Leu Leu Ile Thr Asn Pro Arg Asp Ile
        275                 280                 285

Pro Gly Leu Val Lys Glu Leu Ala Lys Tyr Pro Phe Thr Ala Ile Thr
290                 295                 300

Gly Val Asn Thr Leu Phe Asn Ala Leu Leu Asn Asn Lys Glu Phe Gln
305                 310                 315                 320

Gln Leu Asp Phe Ser Ser Leu His Leu Ser Ala Gly Gly Met Pro
                325                 330                 335

Val Gln Gln Val Val Ala Glu Arg Trp Val Lys Leu Thr Gly Gln Tyr
            340                 345                 350

Leu Leu Glu Gly Tyr Gly Leu Thr Glu Cys Ala Pro Leu Val Ser Val
        355                 360                 365

Asn Pro Tyr Asp Ile Asp Tyr His Ser Gly Ser Ile Gly Leu Pro Val
370                 375                 380

Pro Ser Thr Glu Ala Lys Leu Val Asp Asp Asp Asn Glu Val Pro
385                 390                 395                 400

Pro Gly Gln Pro Gly Glu Leu Cys Val Lys Gly Pro Gln Val Met Leu
                405                 410                 415

Gly Tyr Trp Gln Arg Pro Asp Ala Thr Asp Glu Ile Ile Lys Asn Gly
            420                 425                 430

Trp Leu His Thr Gly Asp Ile Ala Val Met Asp Glu Glu Gly Phe Leu
        435                 440                 445

Arg Ile Val Asp Arg Lys Lys Asp Met Ile Leu Val Ser Gly Phe Asn
450                 455                 460

Val Tyr Pro Asn Glu Ile Glu Asp Val Val Met Gln His Pro Gly Val
465                 470                 475                 480

Gln Glu Val Ala Ala Val Gly Val Pro Ser Gly Ser Gly Glu Ala
                485                 490                 495

Val Lys Ile Phe Val Val Lys Lys Asp Pro Ser Leu Thr Glu Glu Ser
            500                 505                 510

Leu Val Thr Phe Cys Arg Arg Gln Leu Thr Gly Tyr Lys Val Pro Lys
        515                 520                 525

Leu Val Glu Phe Arg Asp Glu Leu Pro Lys Ser Asn Val Gly Lys Ile
530                 535                 540

Leu Arg Arg Glu Leu Arg Asp Glu Ala Arg Gly Lys Val Asp Asn Lys
```

```
545                 550                 555                 560
Ala

<210> SEQ ID NO 13
<211> LENGTH: 382
<212> TYPE: PRT
<213> ORGANISM: Umbellularia californica

<400> SEQUENCE: 13

Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Lys Leu Pro Gln Leu Leu
                85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
        115                 120                 125

Val Met Asn His Met Gln Glu Ala Thr Leu Asn His Ala Lys Ser Val
130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
            180                 185                 190

Gly Asn Asn Gly Met Arg Arg Asp Phe Leu Val Arg Asp Cys Lys Thr
        195                 200                 205

Gly Glu Ile Leu Thr Arg Cys Thr Ser Leu Ser Val Leu Met Asn Thr
    210                 215                 220

Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
            260                 265                 270

Leu Thr Pro Arg Trp Asn Asp Leu Asp Val Asn Gln His Val Asn Asn
        275                 280                 285

Leu Lys Tyr Val Ala Trp Val Phe Glu Thr Val Pro Asp Ser Ile Phe
    290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335

Ser Glu Ala Gly Leu Val Cys Asp His Leu Leu Gln Leu Glu Gly Gly
            340                 345                 350

Ser Glu Val Leu Arg Ala Arg Thr Glu Trp Arg Pro Lys Leu Thr Asp
```

<210> SEQ ID NO 14
<211> LENGTH: 299
<212> TYPE: PRT
<213> ORGANISM: Umbellularia californica

<400> SEQUENCE: 14

Met Glu Trp Lys Pro Lys Pro Lys Leu Pro Gln Leu Leu Asp Asp His
1               5                   10                  15

Phe Gly Leu His Gly Leu Val Phe Arg Arg Thr Phe Ala Ile Arg Ser
            20                  25                  30

Tyr Glu Val Gly Pro Asp Arg Ser Thr Ser Ile Leu Ala Val Met Asn
        35                  40                  45

His Met Gln Glu Ala Thr Leu Asn His Ala Lys Ser Val Gly Ile Leu
    50                  55                  60

Gly Asp Gly Phe Gly Thr Thr Leu Glu Met Ser Lys Arg Asp Leu Met
65                  70                  75                  80

Trp Val Val Arg Arg Thr His Val Ala Val Glu Arg Tyr Pro Thr Trp
                85                  90                  95

Gly Asp Thr Val Glu Val Glu Cys Trp Ile Gly Ala Ser Gly Asn Asn
            100                 105                 110

Gly Met Arg Arg Asp Phe Leu Val Arg Asp Cys Lys Thr Gly Glu Ile
        115                 120                 125

Leu Thr Arg Cys Thr Ser Leu Ser Val Leu Met Asn Thr Arg Thr Arg
    130                 135                 140

Arg Leu Ser Thr Ile Pro Asp Glu Val Arg Gly Glu Ile Gly Pro Ala
145                 150                 155                 160

Phe Ile Asp Asn Val Ala Val Lys Asp Asp Glu Ile Lys Lys Leu Gln
                165                 170                 175

Lys Leu Asn Asp Ser Thr Ala Asp Tyr Ile Gln Gly Gly Leu Thr Pro
            180                 185                 190

Arg Trp Asn Asp Leu Asp Val Asn Gln His Val Asn Asn Leu Lys Tyr
        195                 200                 205

Val Ala Trp Val Phe Glu Thr Val Pro Asp Ser Ile Phe Glu Ser His
    210                 215                 220

His Ile Ser Ser Phe Thr Leu Glu Tyr Arg Arg Glu Cys Thr Arg Asp
225                 230                 235                 240

Ser Val Leu Arg Ser Leu Thr Thr Val Ser Gly Gly Ser Ser Glu Ala
                245                 250                 255

Gly Leu Val Cys Asp His Leu Leu Gln Leu Glu Gly Gly Ser Glu Val
            260                 265                 270

Leu Arg Ala Arg Thr Glu Trp Arg Pro Lys Leu Thr Asp Ser Phe Arg
        275                 280                 285

Gly Ile Ser Val Ile Pro Ala Glu Pro Arg Val
    290                 295

<210> SEQ ID NO 15
<211> LENGTH: 415
<212> TYPE: PRT
<213> ORGANISM: Cuphea hookeriana

<400> SEQUENCE: 15

Met Val Ala Ala Ala Ala Ser Ser Ala Phe Phe Pro Val Pro Ala Pro

```
1               5                   10                  15
Gly Ala Ser Pro Lys Pro Gly Lys Phe Gly Asn Trp Pro Ser Ser Leu
                20                  25                  30

Ser Pro Ser Phe Lys Pro Lys Ser Ile Pro Asn Gly Gly Phe Gln Val
                35                  40                  45

Lys Ala Asn Asp Ser Ala His Pro Lys Ala Asn Gly Ser Ala Val Ser
                50                  55                  60

Leu Lys Ser Gly Ser Leu Asn Thr Gln Glu Asp Thr Ser Ser Ser Pro
65                  70                  75                  80

Pro Pro Arg Thr Phe Leu His Gln Leu Pro Asp Trp Ser Arg Leu Leu
                85                  90                  95

Thr Ala Ile Thr Thr Val Phe Val Lys Ser Lys Arg Pro Asp Met His
                100                 105                 110

Asp Arg Lys Ser Lys Arg Pro Asp Met Leu Val Asp Ser Phe Gly Leu
                115                 120                 125

Glu Ser Thr Val Gln Asp Gly Leu Val Phe Arg Gln Ser Phe Ser Ile
            130                 135                 140

Arg Ser Tyr Glu Ile Gly Thr Asp Arg Thr Ala Ser Ile Glu Thr Leu
145                 150                 155                 160

Met Asn His Leu Gln Glu Thr Ser Leu Asn His Cys Lys Ser Thr Gly
                165                 170                 175

Ile Leu Leu Asp Gly Phe Gly Arg Thr Leu Glu Met Cys Lys Arg Asp
                180                 185                 190

Leu Ile Trp Val Val Ile Lys Met Gln Ile Lys Val Asn Arg Tyr Pro
                195                 200                 205

Ala Trp Gly Asp Thr Val Glu Ile Asn Thr Arg Phe Ser Arg Leu Gly
                210                 215                 220

Lys Ile Gly Met Gly Arg Asp Trp Leu Ile Ser Asp Cys Asn Thr Gly
225                 230                 235                 240

Glu Ile Leu Val Arg Ala Thr Ser Ala Tyr Ala Met Met Asn Gln Lys
                245                 250                 255

Thr Arg Arg Leu Ser Lys Leu Pro Tyr Glu Val His Gln Glu Ile Val
                260                 265                 270

Pro Leu Phe Val Asp Ser Pro Val Ile Glu Asp Ser Asp Leu Lys Val
                275                 280                 285

His Lys Phe Lys Val Lys Thr Gly Asp Ser Ile Gln Lys Gly Leu Thr
                290                 295                 300

Pro Gly Trp Asn Asp Leu Asp Val Asn Gln His Val Ser Asn Val Lys
305                 310                 315                 320

Tyr Ile Gly Trp Ile Leu Glu Ser Met Pro Thr Glu Val Leu Glu Thr
                325                 330                 335

Gln Glu Leu Cys Ser Leu Ala Leu Glu Tyr Arg Arg Glu Cys Gly Arg
                340                 345                 350

Asp Ser Val Leu Glu Ser Val Thr Ala Met Asp Pro Ser Lys Val Gly
                355                 360                 365

Val Arg Ser Gln Tyr Gln His Leu Leu Arg Leu Glu Asp Gly Thr Ala
                370                 375                 380

Ile Val Asn Gly Ala Thr Glu Trp Arg Pro Lys Asn Ala Gly Ala Asn
385                 390                 395                 400

Gly Ala Ile Ser Thr Gly Lys Thr Ser Asn Gly Asn Ser Val Ser
                405                 410                 415

<210> SEQ ID NO 16
```

```
<211> LENGTH: 304
<212> TYPE: PRT
<213> ORGANISM: Cuphea hookeriana

<400> SEQUENCE: 16

Met Asp Arg Lys Ser Lys Arg Pro Asp Met Leu Val Asp Ser Phe Gly
1               5                   10                  15

Leu Glu Ser Thr Val Gln Asp Gly Leu Val Phe Arg Gln Ser Phe Ser
            20                  25                  30

Ile Arg Ser Tyr Glu Ile Gly Thr Asp Arg Thr Ala Ser Ile Glu Thr
        35                  40                  45

Leu Met Asn His Leu Gln Glu Thr Ser Leu Asn His Cys Lys Ser Thr
50                  55                  60

Gly Ile Leu Leu Asp Gly Phe Gly Arg Thr Leu Glu Met Cys Lys Arg
65                  70                  75                  80

Asp Leu Ile Trp Val Val Ile Lys Met Gln Ile Lys Val Asn Arg Tyr
                85                  90                  95

Pro Ala Trp Gly Asp Thr Val Glu Ile Asn Thr Arg Phe Ser Arg Leu
            100                 105                 110

Gly Lys Ile Gly Met Gly Arg Asp Trp Leu Ile Ser Asp Cys Asn Thr
        115                 120                 125

Gly Glu Ile Leu Val Arg Ala Thr Ser Ala Tyr Ala Met Met Asn Gln
130                 135                 140

Lys Thr Arg Arg Leu Ser Lys Leu Pro Tyr Glu Val His Gln Glu Ile
145                 150                 155                 160

Val Pro Leu Phe Val Asp Ser Pro Val Ile Glu Asp Ser Asp Leu Lys
                165                 170                 175

Val His Lys Phe Lys Val Lys Thr Gly Asp Ser Ile Gln Lys Gly Leu
            180                 185                 190

Thr Pro Gly Trp Asn Asp Leu Asp Val Asn Gln His Val Ser Asn Val
        195                 200                 205

Lys Tyr Ile Gly Trp Ile Leu Glu Ser Met Pro Thr Glu Val Leu Glu
210                 215                 220

Thr Gln Glu Leu Cys Ser Leu Ala Leu Glu Tyr Arg Arg Glu Cys Gly
225                 230                 235                 240

Arg Asp Ser Val Leu Glu Ser Val Thr Ala Met Asp Pro Ser Lys Val
                245                 250                 255

Gly Val Arg Ser Gln Tyr Gln His Leu Leu Arg Leu Glu Asp Gly Thr
            260                 265                 270

Ala Ile Val Asn Gly Ala Thr Glu Trp Arg Pro Lys Asn Ala Gly Ala
        275                 280                 285

Asn Gly Ala Ile Ser Thr Gly Lys Thr Ser Asn Gly Asn Ser Val Ser
        290                 295                 300

<210> SEQ ID NO 17
<211> LENGTH: 548
<212> TYPE: PRT
<213> ORGANISM: Lactococcus lactis

<400> SEQUENCE: 17

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45
```

-continued

```
Glu Leu Asn Ala Ser Tyr Met Ala Asp Gly Tyr Ala Arg Thr Lys Lys
 50                  55                  60

Ala Ala Ala Phe Leu Thr Thr Phe Gly Val Gly Glu Leu Ser Ala Val
 65                  70                  75                  80

Asn Gly Leu Ala Gly Ser Tyr Ala Glu Asn Leu Pro Val Val Glu Ile
                 85                  90                  95

Val Gly Ser Pro Thr Ser Lys Val Gln Asn Glu Gly Lys Phe Val His
                100                 105                 110

His Thr Leu Ala Asp Gly Asp Phe Lys His Phe Met Lys Met His Glu
                115                 120                 125

Pro Val Thr Ala Ala Arg Thr Leu Leu Thr Ala Glu Asn Ala Thr Val
130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Lys Ala Glu Lys Pro
                165                 170                 175

Ser Leu Pro Leu Lys Lys Glu Asn Pro Thr Ser Asn Thr Ser Asp Gln
                180                 185                 190

Glu Ile Leu Asn Lys Ile Gln Glu Ser Leu Lys Asn Ala Lys Lys Pro
                195                 200                 205

Ile Val Ile Thr Gly His Glu Ile Ile Ser Phe Gly Leu Glu Asn Thr
                210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Thr Leu Pro Ser Phe Leu Gly Ile
                245                 250                 255

Tyr Asn Gly Lys Leu Ser Glu Pro Asn Leu Lys Glu Phe Val Glu Ser
                260                 265                 270

Ala Asp Phe Ile Leu Met Leu Gly Val Lys Leu Thr Asp Ser Ser Thr
                275                 280                 285

Gly Ala Phe Thr His His Leu Asn Glu Asn Lys Met Ile Ser Leu Asn
                290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Gly Ile Glu Tyr Lys
                325                 330                 335

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
                355                 360                 365

Ser Asn Glu Thr Ile Val Ala Glu Gln Gly Thr Ser Phe Phe Gly Ala
                370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
                420                 425                 430

Gln Leu Thr Val Gln Glu Leu Gly Leu Ala Ile Arg Glu Lys Ile Asn
                435                 440                 445

Pro Ile Cys Phe Ile Ile Asn Asn Asp Gly Tyr Thr Val Glu Arg Glu
                450                 455                 460
```

```
Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495

Lys Ile Val Arg Thr Glu Asn Glu Phe Val Ser Val Met Lys Glu Ala
                500                 505                 510

Gln Ala Asp Pro Asn Arg Met Tyr Trp Ile Glu Leu Val Leu Ala Lys
            515                 520                 525

Glu Asp Ala Pro Lys Val Leu Lys Lys Met Gly Lys Leu Phe Ala Glu
        530                 535                 540

Gln Asn Lys Ser
545

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 18

His His His His His His
1               5
```